United States Patent [19]

Buell et al.

[11] Patent Number: 5,591,152
[45] Date of Patent: * Jan. 7, 1997

[54] ABSORBENT ARTICLE WITH DYNAMIC ELASTIC WAIST FEATURE HAVING A PREDISPOSED RESILIENT FLEXURAL HINGE

[75] Inventors: Kenneth B. Buell, Cincinnati; Sandra H. Clear, Maineville; Danielia T. Falcone, Cincinnati, all of Ohio

[73] Assignee: The Procter & Gamble Company, Cincinnati, Ohio

[*] Notice: The term of this patent shall not extend beyond the expiration date of Pat. No. 5,151,092.

[21] Appl. No.: 466,535

[22] Filed: Jun. 6, 1995

Related U.S. Application Data

[62] Division of Ser. No. 78,538, Jun. 17, 1993, Pat. No. 5,499,978, which is a continuation of Ser. No. 914,958, Jul. 16, 1992, Pat. No. 5,221,274, which is a continuation of Ser. No. 750,775, Aug. 22, 1991, Pat. No. 5,151,092, which is a continuation-in-part of Ser. No. 715,152, Jun. 13, 1991, abandoned.

[51] Int. Cl.$^6$ .............................. A61F 13/15; A61F 13/20
[52] U.S. Cl. .......................................... 604/385.2; 604/373
[58] Field of Search ..................................... 604/358, 367, 604/373, 385.1, 385.2

[56] References Cited

U.S. PATENT DOCUMENTS

| | | |
|---|---|---|
| 4,036,233 | 7/1977 | Kozak . |
| 4,209,016 | 6/1980 | Schaar . |
| 4,381,781 | 5/1983 | Sciaraffa et al. .................... 604/373 |
| 4,515,595 | 5/1985 | Klevit et al. ...................... 604/385.2 |
| 4,731,066 | 3/1988 | Korpman . |
| 4,743,241 | 5/1988 | Igaue et al. . |
| 4,747,846 | 5/1988 | Boland et al. . |
| 4,771,483 | 9/1988 | Hooreman et al. . |
| 4,834,741 | 5/1989 | Sabee . |
| 4,847,134 | 7/1989 | Fahrenkrug et al. . |
| 4,857,067 | 8/1989 | Wood et al. . |
| 4,904,249 | 2/1990 | Miller et al. . |
| 4,940,464 | 7/1990 | Van Gompel et al. . |
| 5,151,092 | 9/1992 | Buell et al. ........................ 604/385.2 |
| 5,334,446 | 8/1994 | Quantrille et al. .................. 428/284 |
| 5,370,634 | 12/1994 | Ando et al. ....................... 604/385.2 |
| 5,464,401 | 11/1995 | Hasse et al. ........................ 604/358 |

*Primary Examiner*—John G. Weiss
*Assistant Examiner*—P. Zuttarelli
*Attorney, Agent, or Firm*—Steven W. Miller; E. Kelly Linman; Jacobus C. Rasser

[57] ABSTRACT

Absorbent article such as disposable diapers, incontinent briefs, diaper holders and the like, that have a unique elastic waist feature that improves the dynamic fit of the elasticized waistband as well as the containment characteristics of the absorbent article. The elastic waist feature preferably comprises an interconnecting panel zone, a first flexural hinge zone joining the interconnecting panel zone with the containment assembly, an elasticized waistband, and a second flexural hinge zone joining the elasticized waistband with the interconnecting panel zone. The elasticized waistband comprises a shaping panel zone; a waistline panel zone; and a predisposed, resilient, waistband flexural hinge zone joining the shaping panel zone and the waistline panel zone. The waistband flexural hinge zone is predisposed to allow the panel zones to flexurally bend about a defined axis or zone and is resilient to provide a restoring force/moment that returns the panel zones to their preceeding in-use configuration, especially when the elasticized waistband has been pretensioned by a closure system. The closure system dynamically creates/maintains lateral tension through the elasticized waistband thereby allowing the elasticized waistband to more dynamically expand and contract with the motions of the wearer. The absorbent article additionally preferably comprises a pair of elasticized side panels disposed in the second waist region. The elasticized side panels preferably comprise a "zero strain" stretch laminate and an extension panel. The present invention also relates to alternative waist features comprising "an expansive tummy panel" elasticized waistband.

12 Claims, 15 Drawing Sheets

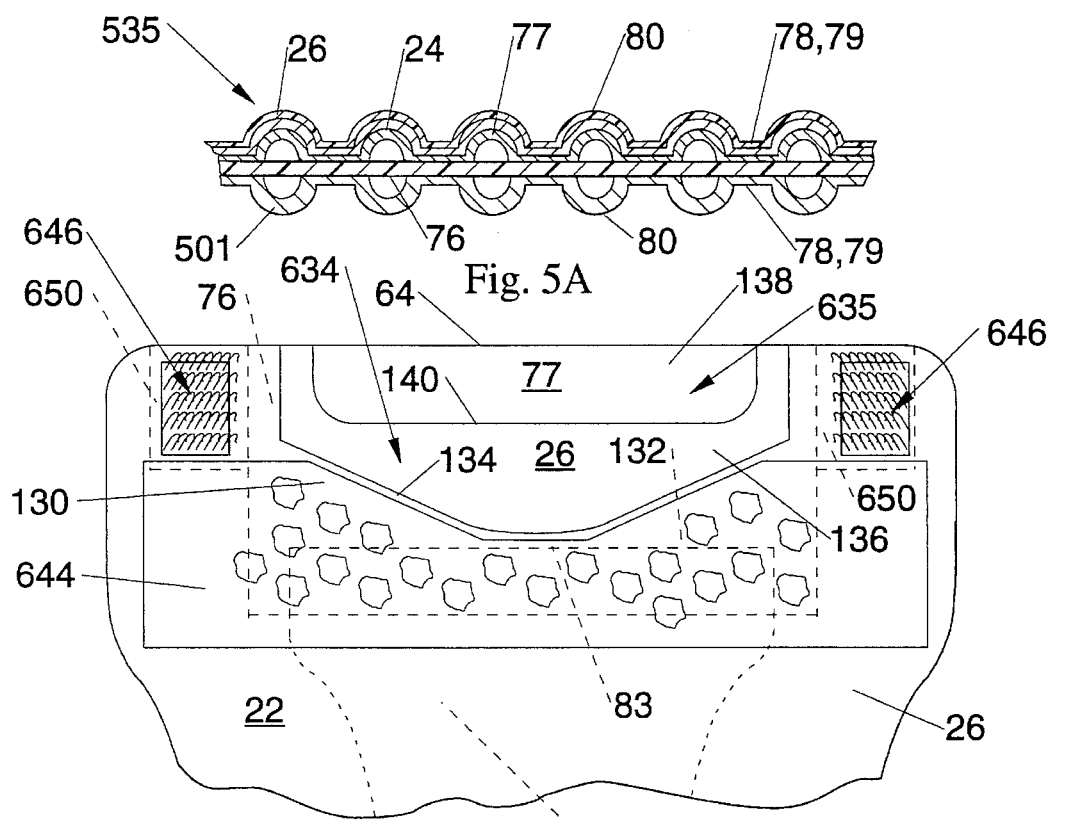
Fig. 5A
Fig. 6
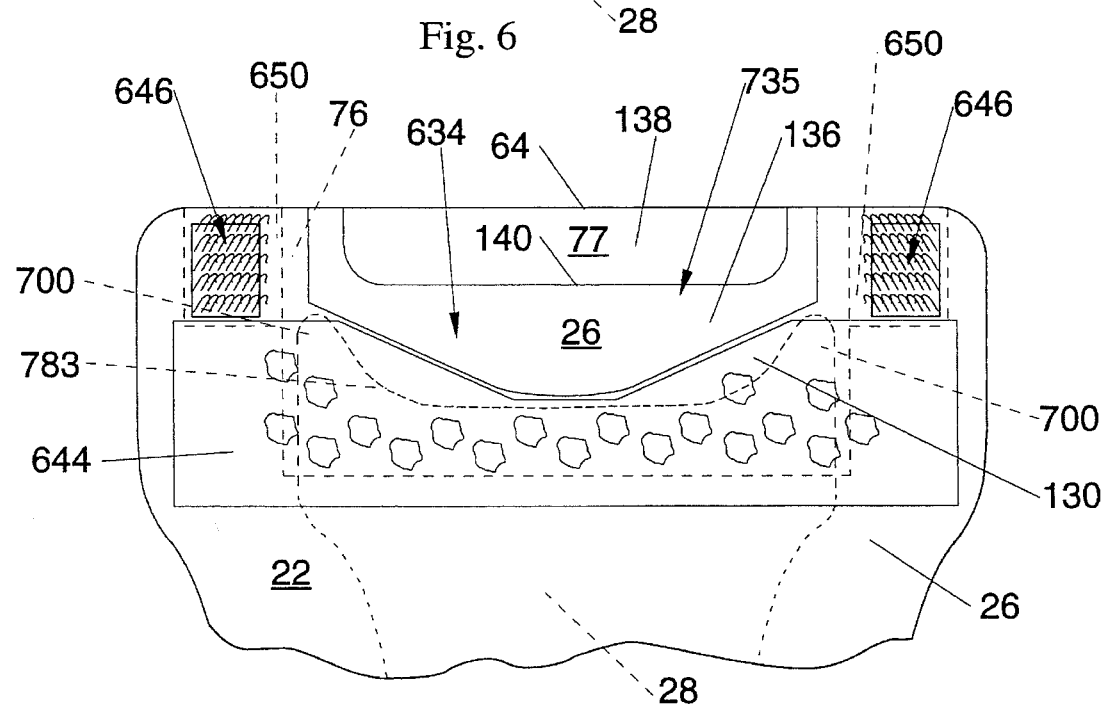
Fig. 7

ABSORBENT ARTICLE WITH DYNAMIC ELASTIC WAIST FEATURE HAVING A PREDISPOSED RESILIENT FLEXURAL HINGE

This is a division of application Ser. No. 08/078,538, filed on Jun. 17, 1993; now U.S. Pat. No. 5,499,978 which is a continuation of application Ser. No. 07/914,958, filed on Jul. 16, 1992, now U.S. Pat. No. 5,221,274; which is a continuation of application Ser. No. 07/750,775, filed on Aug. 22, 1991, now U.S. Pat. No. 5,151,092; which is a continuation-in-part of application Ser. No. 07/715,152, filed on Jun. 13, 1991, now abandoned.

FIELD OF THE INVENTION

The present invention relates to absorbent articles such as diapers, incontinent briefs, diaper holders, and the like, and more particularly, to absorbent articles having elastic waist features providing dynamic fit about the wearer as well as improved containment characteristics of the absorbent article.

BACKGROUND OF THE INVENTION

Infants and other incontinent individuals wear absorbent articles such as diapers to receive and contain urine and other body exudates. Absorbent articles function both to contain the discharged materials and to isolate these materials from the body of the wearer and from the wearer's garments and bed clothing. Disposable absorbent articles having many different basic designs are known to the art. For example, U.S. Pat. No. Re. 26,152, entitled "Disposable Diaper" issued to Duncan and Baker on Jan. 31, 1967, describes a disposable diaper which has achieved wide acceptance and commercial success. U.S. Pat. No. 3,860,003, entitled "Contractable Side Portions For Disposable Diaper", issued to Buell on Jan. 14, 1975, describes an elasticized leg cuff disposable diaper which has achieved wide acceptance and commercial success.

However, absorbent articles have a tendency to sag or gap away from and to slide/slip down on the body of the wearer during wear. This sagging/gapping and sliding/slipping is caused by the relative motions of the wearer as the wearer breathes, moves and changes positions, by the downward forces generated when the absorbent article is loaded with body exudates, and by the deformation of the materials of the absorbent article itself when subjected to such wearer's motions. This sagging/gapping and sliding/slipping of the absorbent article can lead to premature leakage and poor fit of the absorbent article about the wearer in the waist regions and the leg regions of the absorbent article.

In order to more snugly fit absorbent articles about the waist of the wearer, certain commercially available absorbent articles have been provided with elastic waist features. An example of a disposable diaper with an elastic waist feature which has achieved wide acceptance and commercial success is disclosed in U.S. Pat. No. 4,515,595 issued to Kievit and Osterhage on May 7, 1985. Elastic waist features will typically comprise an elasticized waistband consisting of an elastic member contractibly affixed between the topsheet and the backsheet. The elasticized waistband is, thus, designed to expand and contract with the wearer's motions and to maintain the fit of the absorbent article about the waist of the wearer during use (i.e., provide sustained dynamic fit).

However, it has been found that absorbent articles having elastic waist features also have a tendency to sag/gap and slide/slip during use. Further, the elastic waist feature has a tendency to rollover or roll-in at the front of the diaper resulting in a lack of fit about the waist of the wearer.

Thus, it would be advantageous to provide an absorbent article having an elastic waist feature that provides better fit, reduced leakage, and wearer comfort. It would further be advantageous to provide an absorbent article which has reduced sagging, gapping, rollover, or roll-in at the waist of the diaper as well as reduced overall sliding/slipping of the absorbent article or the absorbent core on the wearer during use.

Therefore, it is an object of the present invention to provide an absorbent article having sustained dynamic fit about the waist of the wearer during use.

It is a further object of the present invention to provide an absorbent article having a unique elastic waist feature that provides sustained dynamic fit and improved resistance to leakage during use.

It is a still further object of the present invention to provide an absorbent article having a unique elastic waist feature which reduces sagging, gapping, rollover or roll-in at the front of the diaper as well as overall sliding/slipping of the absorbent article or the absorbent core during use.

It is an another object of the present invention to provide a unique elastic waist feature having an elasticized waistband that provides such sustained dynamic fit by providing a predisposed, resilient, waistband flexural hinge zone which allows relative flexural bending between zones of the elasticized waistband and provides a restoring force/moment to resiliently return the zones to essentially their preceding in-use configuration.

It is a further object of the present invention to provide a closure system that maintains/creates lateral tension through at least a portion of the unique elastic waist feature to enhance the sustained dynamic fit.

These and other objects of the present invention will be more readily apparent when considered in reference to the following description and when taken in conjunction with the accompanying drawings.

SUMMARY OF THE INVENTION

The present invention provides absorbent articles such as disposable diapers, incontinent briefs, diaper holders and the like, that have a unique elastic waist feature that improves the dynamic fit of the elasticized waistband as well as the containment characteristics of the absorbent article. Such absorbent articles comprise a containment assembly preferably comprising a liquid pervious topsheet, a liquid impervious backsheet, and an absorbent core positioned between the topsheet and the backsheet; an elastic waist feature; and a closure system for creating/maintaining lateral tension through at least a portion of the elastic waist feature.

The elastic waist feature preferably comprises an interconnecting panel zone, a first flexural hinge zone joining the interconnecting panel zone with the containment assembly, an elasticized waistband, and a second flexural hinge zone joining the elasticized waistband with the interconnecting panel zone. The elasticized waistband comprises a shaping panel zone; a waistline panel zone; and a predisposed, resilient, waistband flexural hinge zone joining the shaping panel zone and the waistline panel zone. The interconnecting panel zone provides a flexible link between the elasticized waistband and the containment assembly to allow rotations and translations of the elasticized waistband so that the elasticized waistband may move in functional contacting position and conform with the waist of the wearer. The elasticized waistband is designed to elastically expand and contract and to dynamically fit the wearer's waist. The waistband flexural hinge zone is predisposed to allow the panel zones to flexurally bend about a defined axes or zone and is resilient to provide a restoring force/moment that returns the panel zones to their preceding in-use configuration, especially when the elasticized waistband has been pretensioned by the closure system. Thus, the elastic waist feature moves with and conforms to the waist of the wearer as the wearer sits, stands or moves. The elasticized waistband preferably comprises a portion of the topsheet, a portion of the backsheet that is preferably prestrained, an elastomeric member, and a resilient member that enhances the resiliency for the waistband flexural hinge zone.

The absorbent article is also preferably provided with a closure system (tensioning means) for dynamically creating/maintaining lateral tension through the elasticized waistband. The lateral tension dynamically created and maintained by the closure system "activates" the stretch of the elasticized waistband thereby allowing it to more dynamically expand and contract with the motions of the wearer. The closure system preferably comprises a dual tension fastening system. The dual tension fastening system comprises a primary fastening system for forming a side closure and a waist closure system for forming a waist closure. The primary fastening system maintains the first waist region and the second waist region in an overlapping configuration such that lateral tensions are maintained around the circumference of the diaper to maintain the diaper on the wearer. The primary fastening system comprises a securement member, preferably a tape tab and a first fastening component, and a landing member preferably comprising a second fastening component to provide a variable positioning side closure. The waist closure system forms a waist closure that anchors a portion of the end edge of the absorbent article and that dynamically maintains/creates lateral tensions through the elasticized waistband so as to improve the fit and containment characteristics of the diaper by reducing gapping, sagging, and rollover of the elasticized waistband. The waist closure system comprises at least one, preferably a pair of, first attachment component(s) longitudinally aligned with the elasticized waistband and at least one second attachment component. Each attachment component comprises a fastening means that engages a complementary fastening means for providing a variable positioning, passively activated, waist closure. The first attachment component(s) preferably comprise a hook fastening material while the second attachment component preferably comprises a loop fastening material.

In an especially preferred embodiment of the present invention, the absorbent article additionally comprises a pair of elasticized side panels disposed in the second waist region. The elasticized side panels provide an elastically extensible feature that provides a more comfortable and contouring fit by initially conformably fitting the diaper to the wearer and by sustaining this fit. The elasticized side panels further develop and maintain wearing forces (tensions) that enhance the tensions developed and maintained by both the primary fastening system and the waist closure system. The elasticized side panels especially assist in pretensioning the elasticized waistband and further provide more effective application of the diaper. While each elasticized side panel may be constructed in a number of configurations, the elasticized side panel preferably comprises a "zero strain" stretch laminate. The elasticized side panel also preferably has an extension panel adjacent the leg of the wearer so that tensional forces through the side panel are not concentrated so as to prevent the indentation, rubbing, or chafing of the wearer's skin during use.

The present invention also relates to alternative elastic waist features comprising an "expansive tummy panel" elasticized waistband. In these embodiments the elasticized waistband is capable of expanding well beyond the dimensions of the absorbent article set by the primary fastening system (beyond the planar state of the diaper itself) so as to accommodate wearers, especially large infants, with large expansile waists so as to reduce the sagging/slipping of the absorbent article. The extension forces of the elasticized waistband are lower than the extension forces of the elasticized side panels so as to accomodate such expansion. In a preferred embodiment of this elastic waist feature, the elasticized waistband is formed from a stretch laminate. The stretch laminate is comprised of an elastomeric member and a portion of the topsheet and the backsheet which all have been mechanically stretched. In a preferred embodiment, the waistline panel zone is formed by removing a portion of the backsheet (windowing). The shape of the elasticized waistband also provides differential extensibility in the lateral direction.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings in which like designations are used to designate substantially identical elements, and in which:

FIG. 5A is a fragmentary sectional view of a further alternative disposable diaper embodiment of the present invention showing a further alternative construction of the elasticized waistband;

FIG. 6 is a fragmentary plan view of another alternative disposable diaper embodiment of the present invention showing an elastic waist feature of an "expansive tummy panel" having differential extensibility in the lateral direction and a "windowed" elastic waist feature;

FIG. 7 is a fragmentary plan view of an alternative embodiment of the elastic waist feature shown in FIG. 6;

DETAILED DESCRIPTION OF THE INVENTION

As used herein, the term "absorbent article" refers to devices which absorb and contain body exudates, and, more specifically, refers to devices which are placed against or in proximity to the body of the wearer to absorb and contain the various exudates discharged from the body. The term "disposable" is used herein to describe absorbent articles which are not intended to be laundered or otherwise restored or reused as an absorbent article (i.e., they are intended to be discarded after a single use and, preferably, to be recycled, composted or otherwise disposed of in an environmentally compatible manner). A "unitary" absorbent article refers to absorbent articles which are formed of separate parts united together to form a coordinated entity so that they do not require separate manipulative parts like m separate holder and liner. A preferred embodiment of an absorbent article of the present invention is the unitary disposable absorbent article, diaper 20, shown in FIG. 1. As used herein, the term "diaper" refers to an absorbent article generally worn by infants and incontinent persons that is worn about the lower torso of the wearer. It should be understood, however, that the present invention is also applicable to other absorbent articles such as incontinent briefs, incontinent undergarments, diaper holders and liners, feminine hygiene garments, and the like.

Figure 1:
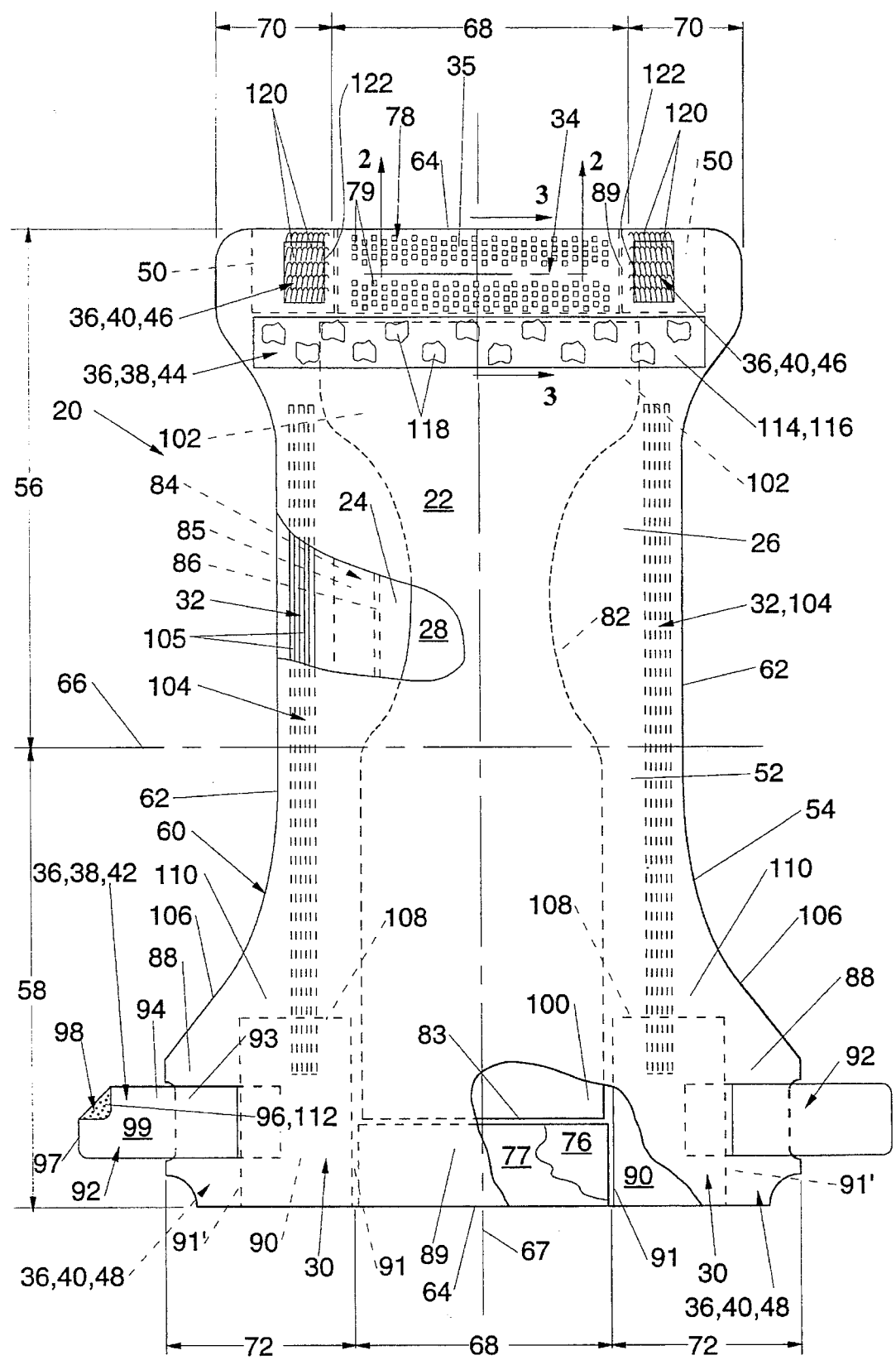
FIG. 1 is a plan view of a disposable diaper embodiment of the present invention having portions cut-away to reveal underlying structure, the outer surface of the diaper facing the viewer.

FIG. 1 is a plan view of the diaper 20 of the present invention in its flat-out, uncontracted state (i.e., with elastic induced contraction pulled out except in the side panels wherein the elastic is left in its relaxed condition) with portions of the structure being cut-away to more clearly show the construction of the diaper 20 and with the portion of the diaper 20 which faces away from the wearer, the outer surface 52, facing the viewer. As shown in FIG. 1, the diaper 20 comprises a containment assembly 22 preferably comprising a liquid pervious topsheet 24, a liquid impervious backsheet 26 joined with the topsheet 24, and an absorbent core 28 positioned between the topsheet 24 and the backsheet 26; elasticized side panels 30; elasticized leg cuffs 32; an elastic waist feature 34; and a closure system comprising a dual tension fastening system generally multiply designated as 36. The dual tension fastening system 36 preferably comprises a primary fastening system 38 and a waist closure system 40. The primary fastening system 38 preferably comprises a pair of securement members 42 and a landing member 44. The waist closure system 40 is shown in FIG. 1 to preferably comprise a pair of first attachment components 46 and a second attachment component 48. The diaper 20 also preferably comprises a positioning patch 50 located subjacent each first attachment component 46.

The diaper 20 is shown in FIG. 1 to have an outer surface 52 (facing the viewer in FIG. 1), an inner surface 54 opposed to the outer surface 52, a first waist region 56, a second waist region 58 opposed to the first waist region 56, and a periphery 60 which is defined by the outer edges of the diaper 20 in which the longitudinal edges are designated 62 and the end edges are designated 64. (While the skilled artisan will recognize that a diaper is usually described in terms of having a pair of waist regions and a crotch region between the waist regions; in this application, for simplicity of terminology, the diaper 20 is described as having only waist regions, each of the waist regions including a portion of the diaper which would typically be designated as part of the crotch region). The inner surface 54 of the diaper 20 comprises that portion of the diaper 20 which is positioned adjacent to the wearer's body during use (i.e., the inner surface 54 generally is formed by at least a portion of the topsheet 24 and other components joined to the topsheet 24). The outer surface 52 comprises that portion of the diaper 20 which is positioned away from the wearer's body (i.e., the outer surface 52 generally is formed by at least a portion of the backsheet 26 and other components joined to the backsheet 26). The first waist region 56 and the second waist region 58 extend, respectively, from the end edges 64 of the periphery 60 to the lateral centerline 66 of the diaper 20. The waist regions each comprise a central region 68 and a pair of side panels which typically comprise the outer lateral portions of the waist regions. The side panels positioned in the first waist region 56 are designated 70 while the side panels in the second waist region 58 are designated 72. (In the discussion that follows, unless otherwise noted, the diaper 20 will comprise a pair of side panels in each waist region. While it is not necessary that the pairs of side panels or each side panel be identical, they are preferably mirror images one of the other.) In a preferred embodiment of the present invention, the side panels 72 positioned in the second waist region 58 are elastically extensible in the lateral direction (i.e., elasticized side panels 30). (The lateral direction (x direction or width) is defined as the direction parallel to the lateral centerline 66 of the diaper 20; the longitudinal direction (y direction or length) being defined as the direction parallel to the longitudinal centerline 67; and the axial direction (Z direction or thickness) being defined as the direction extending through the thickness of the diaper 20.)

FIG. 1 shows a preferred embodiment of the diaper 20 which the topsheet 24 and the backsheet 26 have length and width dimensions generally larger than those of the absorbent core 28. The topsheet 24 and the backsheet 26 extend beyond the edges of the absorbent core 28 to thereby form the periphery 60 of the diaper 20. The periphery 60 defines the outer perimeter or, in other words, the edges of the diaper 20. The periphery 60 comprises the longitudinal edges 62 and the end edges 64.

Figure 2:
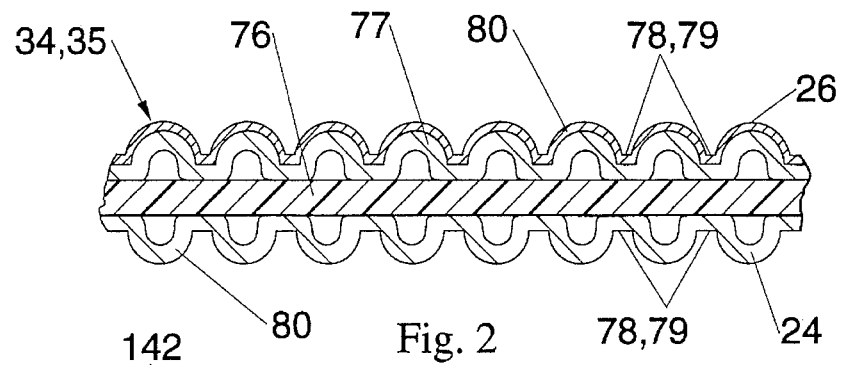
FIG. 2 is a fragmentary sectional view of the disposable diaper shown in FIG. 1 taken along section line 2—2 of FIG. 1.

FIG. 2 is a cross-sectional view of the diaper 20 taken along section line 2—2 of FIG. 1 in the first waist region 56. FIG. 2 shows the construction of the elasticized waistband 35 of the elastic waist feature 34. The elasticized waistband 35 shown in FIG. 2 in its contracted or relaxed condition. The elasticized waistband 35 preferably comprises a portion of the topsheet 24, a portion of the backsheet 26 that has preferably been mechanically stretched, and a bi-laminate material comprising an elastomeric member 76 positioned between the topsheet 24 and the backsheet 26 and a resilient member 77 positioned between the backsheet 26 and the elastomeric member 76. The elasticized waistband 35 is also provided with regions of securement 78 wherein the backsheet 26 and the topsheet 24 are joined to the bi-laminate material of the elastomeric member 76 and the resilient member 77. Since the topsheet 24 and the backsheet 26 are gathered when the bi-laminate material is in its relaxed condition, regions of differential securement are provided which form pleats 80.

Figure 3:
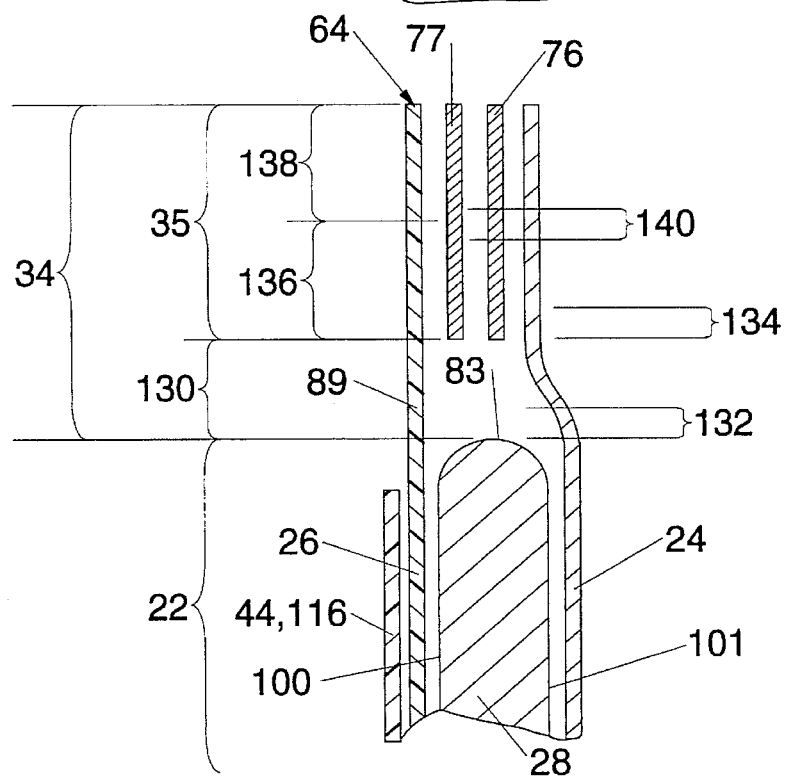
FIG. 3 is a fragmentary sectional view of the disposable diaper shown in FIG. 1 taken along section line 3—3 of FIG. 1.

FIG. 3 is a fragmentary cross-sectional view of the diaper 20 taken along line 3—3 of FIG. 1 and depicts a preferred elastic waist feature construction in the first waist region The absorbent core 28 is generally shown in FIG. 3 and shows the waist edge 83 of the absorbent core 28. The topsheet 24 and the backsheet 26 encase the absorbent core 28 and extend longitudinally outwardly beyond the waist edge 83 of the absorbent core 28 to form a waist flap 89 and the end edge 64. The elastic waist feature 34 extends longitudinally outwardly from the waist edge 83 of the absorbent core 28 in at least the central region 68 and forms at least a portion of the end edge 64. The elastic waist feature 34 comprises an interconnecting panel zone 130, a first flexural hinge zone 132 joining the interconnecting panel zone 130 with the containment assembly 22 adjacent the waist edge 83 of the absorbent core 28, an elasticized waistband 35, and second flexural hinge zone 134 joining the elasticized waistband 35 with the interconnecting panel zone 130. As shown in FIG. 3, the elasticized waistband 35 comprises a shaping panel zone 136; a waistline panel zone 138; and a predisposed, resilient, waistband flexural hinge zone 140 joining the shaping panel zone 136 and the waistline panel zone 138. As shown in FIG. 3, the interconnecting panel zone 130 comprises a portion of the topsheet 24 and the backsheet 26 while the elasticized waistband comprises a portion of the topsheet 24 and the backsheet 26 and the bi-laminate material of the elastomeric member 76 and the resilient member 77.

Figure 2A:
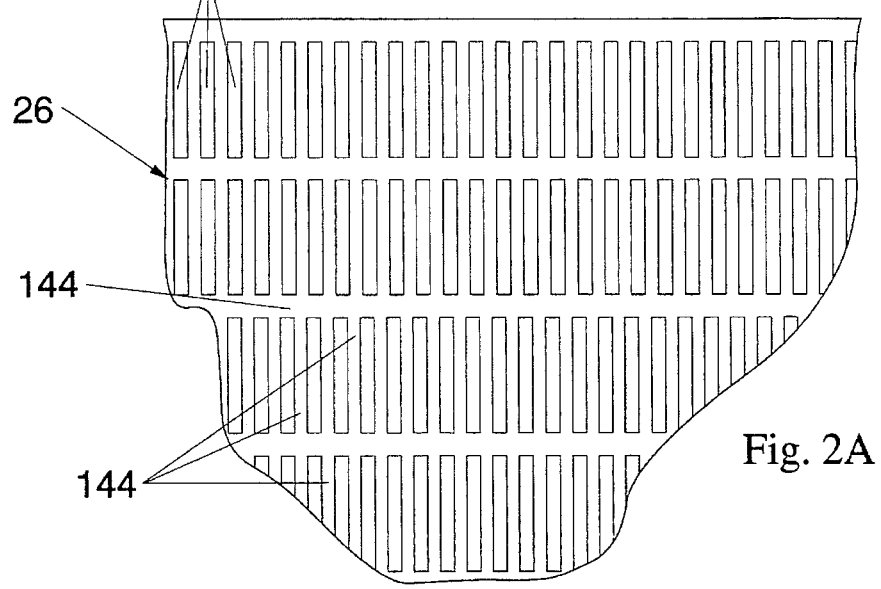
FIG. 2A is a plan view of the prestrained backsheet portion of the disposable diaper showing the pattern of the mechanical stretching.
Figure 2B:
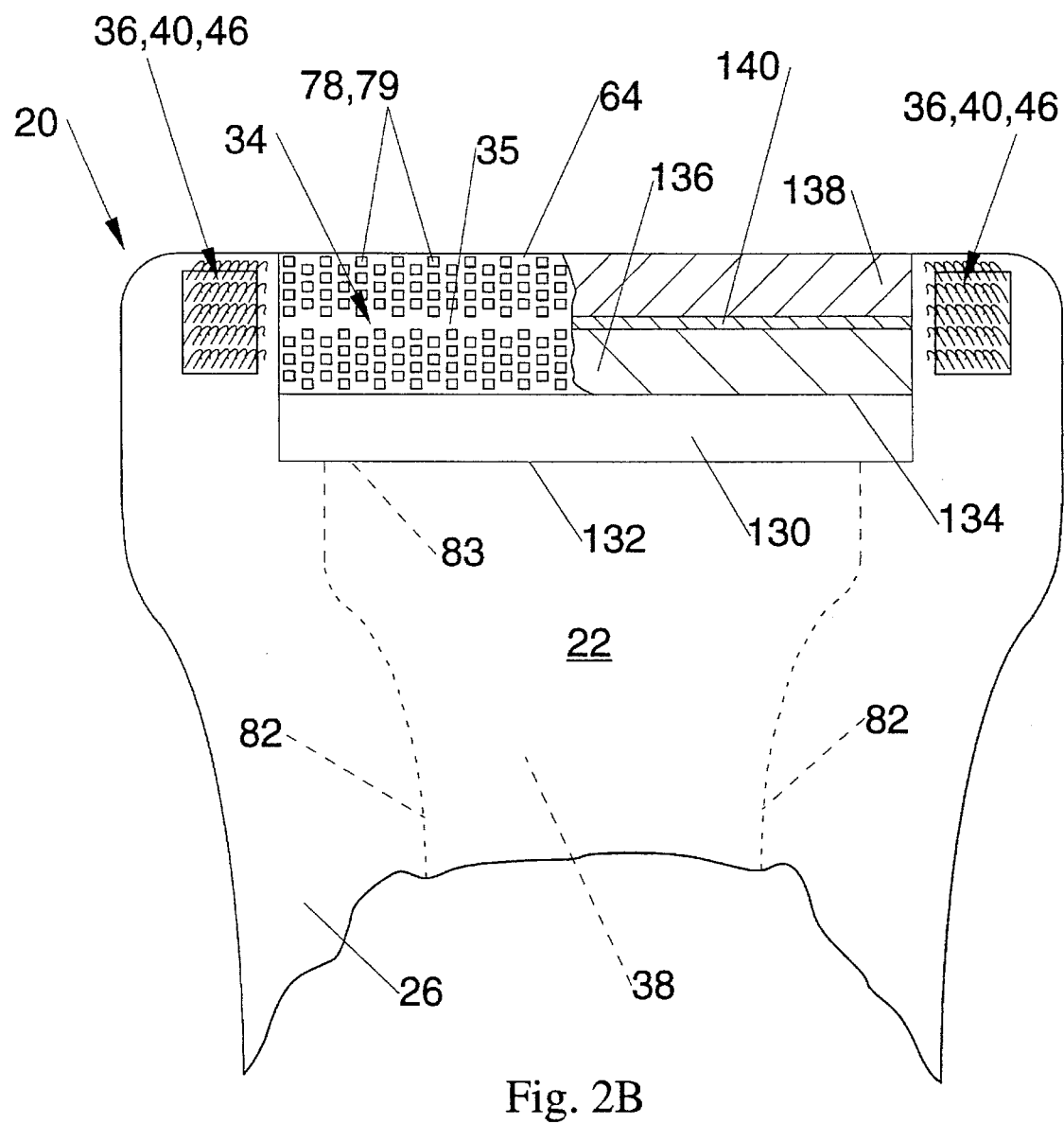
FIG. 2B is a simplified, fragmentary, enlarged plan view of the disposable diaper of the present invention in the first waist region showing the elements of the elastic waist feature.

FIG. 2B is a simplified, fragmentary, enlarged plan view of the disposable diaper 20 in the first waist region 56 showing generally the various zones and elements of the elastic waist feature 34. The absorbent core 28 is generally shown and has the waist edge 83 and the side edges 82. The panel zones of the elastic waist feature 34 are generally represented by the shaded areas. The panel zones comprise the interconnecting panel zone 130 and the elasticized waistband 35 comprising the shaping panel zone 136 and the waistline panel zone 138. The flexural hinge zones are generally depicted by lines even though they may comprise regions or zones which have some significant width so as to exhibit bending/flexure deformation. The flexural hinge zones comprise the first flexural hinge zone 132, the second flexural hinge zone 134, and the waistband flexural hinge zone 140. The closure system is shown as comprising a pair of first attachment components 46 longitudinally aligned with the elasticized waistband 35 so as to maintain/create lateral tension through the elasticized waistband 35. The first attachment component 46 preferably comprises a separate patch of material, preferably a hook fastening material, joined to the backsheet 26.

The containment assembly 22 of the diaper 20 is shown in FIG. 1 as comprising the main body (chassis) of the diaper 20. The containment assembly 22 comprises at least an absorbent core 28 and preferably an outer covering layer comprising the topsheet 24 and the backsheet 26. When the absorbent article comprises a separate holder and a liner, the containment assembly 22 generally comprises the holder and the liner (i.e., the containment assembly 22 comprises one or more layers of material to define the holder while the liner comprises an absorbent composite such as a topsheet, a backsheet, and an absorbent core.) For unitary absorbent articles, the containment assembly 22 comprises the main structure of the diaper with other features added to form the composite diaper structure. Thus, the containment assembly 22 for the diaper 20 generally comprises the topsheet 24, the backsheet 26, and the absorbent core 28.

The absorbent core 28 may be any absorbent means which is generally compressible, conformable, non-irritating to the wearer's skin, and capable of absorbing and retaining liquids such as urine and other certain body exudates. As shown in FIG. 1, the absorbent core 28 has a garment surface 100, a body surface 101, side edges 82, and waist edges 83.

The absorbent core 28 may be manufactured in a wide variety of sizes and shapes (e.g., rectangular, hourglass, "T"-shaped, asymmetric, etc.) and from a wide variety of liquid-absorbent materials commonly used in disposable diapers and other absorbent articles such as comminuted wood pulp which is generally referred to as airfelt. Examples of other suitable absorbent materials include creped cellulose wadding, meltblown polymers including coform, cross-linked cellulosic fibers, tissue including tissue wraps and tissue laminates, absorbent foams, absorbent sponges, superabsorbent polymers, absorbent gelling materials, or any equivalent material or combinations of materials. The configuration and construction of the absorbent core may also be varied (e.g., the absorbent core may have varying caliper zones, hydrophilic gradient, a superabsorbent gradient, or lower average density and lower average basis weight acquisition zones; or may comprise one or more layers or structures). The total absorbent capacity of the absorbent core 28 should, however, be compatible with the design loading and the intended use of the diaper 20. Further, the size and absorbent capacity of the absorbent core 28 may be varied to accommodate wearers ranging from infants through adults.

A preferred embodiment of the diaper 20 has an asymmetric, modified T-shaped, absorbent core 28 having ears 102 in the first waist region 56 but a generally rectangular shape in the second waist region 58. This configuration allows wider elasticized side panels 30 in the second waist region 58. An exemplary absorbent structure for use as the absorbent core 28 of the present invention that has achieved wide acceptance and commercial success is described in U.S. Pat. No. 4,610,678 entitled "High-Density Absorbent Structures" issued to Weisman and Goldman on Sep. 9, 1986. U.S. Pat. No. 4,673,402 entitled "Absorbent Articles With Dual-Layered Cores" issued to Weisman, Houghton, and Gellert on Jun. 16, 1987; and U.S. Pat. No. 4,888,231 entitled "Absorbent Core Having A Dusting Layer" issued to Angstadt on Dec. 19, 1989; also describe absorbent structures that are useful in the present invention. The absorbent core 28 is preferably the commercially successful absorbent member described in U.S. Pat. No. 4,834,735, entitled "High Density Absorbent Members Having Lower Density and Lower Basis Weight Acquisition Zones", issued to Alemany and Berg on May 30, 1989. Each of these references are incorporated herein by reference.

The backsheet 26 is positioned adjacent the garment surface 100 of the absorbent core 28 and is preferably joined thereto by attachment means (not shown) such as those well known in the art. For example, the backsheet 26 may be secured to the absorbent core 28 by a uniform continuous layer of adhesive, a patterned layer of adhesive, or an array of separate lines, spirals, or spots of adhesive. Adhesives which have been found to be satisfactory are manufactured by Century Adhesives, Inc. of Columbus, Ohio and marketed as Century 5227; and by H. B. Fuller Company of St. Paul, Minn. and marketed as HL-1258. The attachment means will preferably comprise an open pattern network of filaments of adhesive as is disclosed in U.S. Pat. No. 4,573,986 entitled "Disposable Waste-Containment Garment", which issued to Minetola and Tucker on Mar. 4, 1986, and which is incorporated herein by reference. An exemplary attachment means of an open pattern network of filaments comprises several lines of adhesive filaments swirled into a spiral pattern such as is illustrated by the apparatus and methods shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Each of these patents are incorporated herein by reference. Alternatively, the attachment means may comprise heat bonds, pressure bonds, ultrasonic bonds, dynamic mechanical bonds, or any other suitable attachment means or combinations of these attachment means as are known in the art.

The backsheet 26 is impervious to liquids (e.g., urine) and is preferably manufactured from a thin plastic film, although other flexible liquid impervious materials may also be used. As used herein, the term "flexible" refers to materials which are compliant and will readily conform to the general shape and contours of the human body. The backsheet 26 prevents the exudates absorbed and contained in the absorbent core 28 from wetting articles which contact the diaper 20 such as bedsheets and undergarments. The backsheet 26 may thus comprise a woven or nonwoven material, polymeric films such as thermoplastic films of polyethylene or polypropylene, or composite materials such as a film-coated nonwoven material. Preferably, the backsheet is a thermoplastic film having a thickness of from about 0.012 mm (0.5 mil) to about 0.051 mm (2.0 mils).

In a preferred embodiment of the present invention, at least a portion of the backsheet 26 is subjected to mechanical stretching in order to provide both a "zero strain" stretch laminate that forms the elasticized side panels 30 and to prestrain the portion of the backsheet coinciding with the elastic waist feature. Thus, the backsheet 26 is preferably elongatable, most preferably drawable, but not necessarily elastomeric, so that the backsheet 26 will, upon mechanical stretching, be at least to a degree permanently elongated such that it will not fully return to its original undistorted configuration. In preferred embodiments, the backsheet can be subjected to mechanical stretching without undue rupturing or tearing. Thus, it is preferred that the backsheet 26 have an ultimate elongation to break of at least about 400% to about 700% in the cross-machine direction as measured using a method consistent with ASTM D-638. Thus, preferred polymeric films for use as the backsheet contain a high content of linear low density polyethylene. Particularly preferred materials for the backsheet include blends comprised of about 45–90% linear low density polyethylene and about 10–55% polypropylene. Exemplary films for use as the backsheet of the present invention are manufactured by Tredegar Industries, Inc. of Terre Haute, Ind. under the designation RR8220 blend for blown films and RR5475 blend for cast films. The backsheet 26 is preferably embossed (typically, to a caliper of about 0.127 mm (5.5 mils)) and/or matte finished to provide a more clothlike appearance. Further, the backsheet 26 may permit vapors to escape from the absorbent core 28 (i.e., breathable) while still preventing exudates from passing through the backsheet 26.

The size of the backsheet 26 is dictated by the size of the absorbent core 28 and the exact diaper design selected. In a preferred embodiment, the backsheet 26 has a modified hourglass shape extending beyond the absorbent core 28 a minimum distance of at least about 1.3 cm to about 2.5 cm (about 0.5 to about 1.0 inch) around the entire diaper periphery 60. Preferably, the backsheet 26 is much wider than the absorbent core 28 in the second waist region 58 so that the side panels 72 in the second waist region 58 are generally wider in the lateral direction than the side panels 70 in the first waist region 56.

The topsheet 24 is positioned adjacent the body surface 101 of the absorbent core 28 and is preferably joined thereto and to the backsheet 26 by attachment means (not shown) such as those well known in the art. Suitable attachment means are described with respect to joining the backsheet 26 to the absorbent core 28. As used herein, the term "Joined" encompasses configurations whereby an element is directly secured to the other element by affixing the element directly to the other element, and configurations whereby the element is indirectly secured to the other element by affixing the element to intermediate member(s) which in turn are affixed to the other element. In a preferred embodiment of the present invention, the topsheet 24 and the backsheet 26 are joined directly to each other in the diaper periphery 60 and are indirectly joined together by directly joining them to the absorbent core 28 by the attachment means (not shown).

The topsheet 24 is compliant, soft feeling, and non-irritating to the wearer's skin. Further, the topsheet 24 is liquid pervious permitting liquids (e.g., urine) to readily penetrate through its thickness. A suitable topsheet may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. Preferably, the topsheet 24 is made of a hydrophobic material to isolate the wearer's skin from liquids contained in the absorbent core 28.

In a preferred embodiment of the present invention, at least a portion of the topsheet 24 is subjected to mechanical stretching in order to provide a "zero strain" stretch laminate that forms the elasticized side panels 30. Thus, the topsheet 24 is preferably elongatable, most preferably drawable, but not necessarily elastomeric, so that the topsheet 24 will, upon mechanical stretching, be at least to a degree permanently elongated such that it will not fully return to its original configuration. In preferred embodiments, the topsheet 24 can be subjected to mechanical stretching without undue rupturing or tearing of the topsheet. Thus, it is preferred that the topsheet 24 have a low cross-machine direction (lateral direction) yield strength.

There are a number of manufacturing techniques which may be used to manufacture the topsheet 24. For example, the topsheet 24 may be a nonwoven web of fibers. When the topsheet comprises a nonwoven web, the web may be spunbonded, carded, wet-laid, meltblown, hydroentangled, combinations of the above, or the like. A preferred topsheet is carded and thermally bonded by means well known to those skilled in the fabrics art. A preferred topsheet comprises staple length polypropylene fibers having a denter of about 2.2. As used herein, the term "staple length fibers" refers to those fibers having a length of at least about 15.9 mm (0.625 inches). Preferably, the topsheet has a basis weight from about 18 to about 25 grams per square meter. A suitable topsheet is manufactured by Veratec, Inc., a Division of International Paper Company, of Walpole, Mass. under the designation P-8.

The diaper 20 preferably further comprises elasticized leg cuffs 32 for providing improved containment of liquids and other body exudates. Each elasticized leg cuff 32 may comprise several different embodiments for reducing the leakage of body exudates in the leg regions. (The leg cuff can be and is sometimes also referred to as leg bands, side flaps, barrier cuffs, or elastic cuffs.) U.S. Pat. No. 3,860,003 entitled "Contractable Side Portions For a Disposable Diaper" issued to Buell on Jan. 14, 1975, describes a disposable diaper which provides a contractible leg opening having a side flap and one or more elastic members to provide an elasticized leg cuff (gasketing cuff). U.S. Pat. No. 4,909,803 entitled "Disposable Absorbent Article Having Elasticized Flaps" issued to Aziz and Blaney on Mar. 20, 1990, describes a disposable diaper having "stand-up" elasticized flaps (barrier cuffs) to improve the containment of the leg regions. U.S. Pat. No. 4,695,278 entitled "Absorbent Article Having Dual Cuffs" issued to Lawson on Sep. 22, 1987, describes a disposable diaper having dual cuffs including a gasketing cuff and a barrier cuff. U.S. Pat. No. 4,704,115 entitled "Disposable Waist Containment Garment" issued to Buell on Nov. 3, 1987, discloses a disposable diaper or incontinent garment having side-edge-leakage-guard gutters configured to contain free liquids within the garment. Each of these patents are incorporated herein by reference. While each elasticized leg cuff 32 may be configured so as to be similar to any of the leg bands, side flaps, barrier cuffs, or elastic cuffs described above, it is preferred that each elasticized leg cuff 32 comprise at least an inner barrier cuff 84 comprising a barrier flap 85 and a spacing elastic member 86 such as described in the above-referenced U.S. Pat. No. 4,909,803. In a preferred embodiment, the elasticized leg cuff 32 additionally comprises an elastic gasketing cuff 104 with one or more elastic strands 105, positioned outboard of the barrier cuff 84 such as described in the above-referenced U.S. Pat. No. 4,695,278.

The diaper 20 further comprises an elastic waist feature 34 that provides improved fit and containment. The elastic waist feature 34 at least extends longitudinally outwardly from at least one of the waist edges 83 of the absorbent core 28 in at least the central region 68 and generally forms at least a portion of the end edge 64 of the diaper 20. Thus, the elastic waist feature 34 comprises that portion of the diaper at least extending from the waist edge 83 of the absorbent core 28 to the end edge 64 of the diaper 20 and is intended to be placed adjacent the wearer's waist. Disposable diapers are generally constructed so as to have two elastic waist features, one positioned in the first waist region and one positioned in the second waist region. While a disposable diaper of the present invention can be constructed with a single elastic waist feature encircling the wearer, the discussion regarding the elastic waist feature will focus on diapers having a pair of elastic waist features, at least one, and preferably both, being constructed according to the present invention. Further, while the elastic waist feature or any of its constituent elements can comprise a separate element affixed to the containment assembly 22 of the diaper 20, the elastic waist feature 34 will be described with respect to a preferred embodiment in which the elastic waist feature 34 is constructed as an extension of other elements of the diaper such as the backsheet 26 or the topsheet 24, preferably both the backsheet 26 and the topsheet 24.

While the elastic waist feature 34 need only comprise an elasticized waistband and a flexural hinge zone joining the elasticized waistband with the containment assembly; as shown in FIG. 3, the elastic waist feature 34 preferably comprises several additional zones. In particular, the elastic waist feature 34 comprises an interconnecting panel zone 130, a first flexural hinge zone 132 joining the interconnecting panel zone 130 with the containment assembly 22 adjacent the waist edge 83 of the absorbent core 28, an elasticized waistband 35, and a second flexural hinge zone 134 joining the elasticized waistband 35 with the interconnecting panel zone 130. The interconnecting panel zone 130 preferably provides a flexible link between the elasticized waistband 35 and the containment assembly 22. The elasticized waistband 35 provides a member that maintains a defined area coverage, contacts the wearer's waist, and is elastically extensible in at least the lateral direction so as to dynamically fit against the waist of the wearer and to dynamically conform to the waist of the wearer so as to provide improved fit. As shown in FIG. 3, the elasticized waistband 35 comprises a shaping panel zone 136; a waistline panel zone 138; and a predisposed, resilient, waistband flexural hinge zone 140 joining the shaping panel zone 136 and the waistline panel zone 138. As used herein, the term "zone" is used to denote an area or element of the elastic waist feature 34. While a zone of the elastic waist feature 34 may be a distinct area or element; typically, a zone of the elastic waist feature will overlap somewhat with an adjacent zone(s). (For illustration purposes, the zones are delineated with brackets in FIG. 3.)

The interconnecting panel zone 130 provides a link between the elasticized waistband 35 and the containment assembly 22 to allow rotations and translations of the elasticized waistband 35 so that the elasticized waistband may move in functional contacting position and conform with the waist of the wearer. The interconnecting panel zone 130 is preferably flexible so that the interconnecting panel zone is free to deform randomly throughout its length and width so as to allow the elasticized waistband 35 to maintain contact with the waist of the wearer and to allow the absorbent core 28 to position itself during wear. While the interconnecting panel zone 130 may have a significant edge compression stiffness; in a preferred embodiment, the interconnecting panel zone is flexible such that the edge compression stiffness of the interconnecting panel zone is preferably substantially less than the edge compression stiffness of both the shaping panel zone 136 and the waistline panel zone 138. It is preferred that the interconnecting panel zone 130 have an edge compression stiffness less than about 50 grams$_f$, more preferably less than about 25 grams$_f$. Typically, the edge compression stiffness of the interconnecting panel zone (comprising a portion of the topsheet 24 and a portion of the backsheet 26 joined together) is less than about 10 grams$_f$. Further, while the interconnecting panel zone 130 may be elastically extensible in the longitudinal direction, the lateral direction, or in any other direction, the interconnecting panel zone is preferably longitudinally nonextensible to provide a fixed dimension length between the elasticized waistband 35 and the containment assembly 22. The length of the interconnecting panel zone 130 is preferably at least about 4.75 mm (about 3/16 inch), more preferably between about 6.25 mm (about 1/4 inch) and about 12.5 mm (about 1/2 inch) for medium-sized diapers.

The interconnecting panel zone 130 may be constructed from a separate material flexurally joined to the containment assembly 22 and/or the elasticized waistband 35, or as an extension of other elements of the diaper 20. In a preferred embodiment as shown in FIG. 3, the interconnecting panel zone 130 comprises a portion of both the topsheet 24 and the backsheet 26 extending beyond the waist edge 83 of the absorbent core 28. The backsheet 26 and the topsheet 24 are preferably joined to each other (joined together) by an attachment means (not shown) in the interconnecting panel zone 130 so that they perform as a unit rather than independently of each other. The attachment means for securing the topsheet 24 and the backsheet 26 to each other preferably comprises an open pattern network of adhesive deposited in a spiral or looping pattern, although other attachment means as described hereinbefore may also be used.

The interconnecting panel zone 130 is flexurally joined with the containment assembly 22 and the shaping panel zone 136 by flexural hinge zones (first flexural hinge zone 132 and second flexural hinge zone 134, respectively) so that the elasticized waistband 35 may translate and/or rotate in the axial direction (Z-direction). As used herein, the term "flexurally joined" means a joint between panel zones or a panel zone and the containment assembly adapted to allow relative flexural bending between the panel zones. (As discussed hereinafter, this flexural bending is not necessarily such that the panel zones will return to their previous configuration when the forces causing the flexural bending are removed (i.e., they are not necessarily resilient).

A flexural hinge zone can be constructed in various ways. The flexural hinge zone may comprise a zone of structural discontinuity between panel zones. The cross-sectional configuration of the panel zones may be varied to allow flexural bending between the panel zones. For example, the materials making up the panel zones can be scored, compressed, embossed, creased, folded, bonded, reduced, cut, notched, slit, or eliminated to form an axis or axes of flexural bending. Typically, these methods will concentrate stresses/tensions to m particular line or axes through which flexural bending can occur. A line of reduced extension or a line of restraint may also be formed between zones to form a hinge zone. As an alternative, the flexural hinge zone may comprise a zone of material discontinuity between the panel zones. For example, the materials making up the panel zones may have a relative different modulus of bending or elasticity to provide an area or zone of different flexural resistance (differential bending stiffness between the zones) which allows flexural bending between the panel zones.

As shown in FIG. 3, the second flexural hinge zone 134 joining the elasticized waistband 35 (shaping panel zone 136) with the interconnecting panel zone 130 is formed at the zone where there is a structural discontinuity due to the elimination of the elastomeric member 76 and the resilient member 77 from the interconnecting panel zone 130. Thus, the second flexural hinge zone 134 is created adjacent the bottom edge of the elastomeric member 76 and the resilient member 77. The first flexural hinge zone 132 joining the interconnecting panel zone 130 with the containment assembly 22 is formed at the zone where there is a structural discontinuity due to the absence of the absorbent core 28 from the interconnecting panel zone 130.

The elasticized waistband 35 is that portion or zone of the diaper 20 which is intended to elastically expand and contract and to dynamically fit the wearer's waist. While the elasticized waistband 35 can comprise a separate element flexurally joined with the interconnecting panel zone 130, the elasticized waistband 35 is preferably formed as an extension of the topsheet 24 or the backsheet 26, and, most preferably, the topsheet 24 and the backsheet 26. The elasticized waistband 35 is preferably that portion of the elastic waist feature 34 extending from the second flexural hinge zone 134 to, preferably but not necessarily, the end edge 64 of the diaper 20. In a preferred embodiment shown in FIG. 3, the elasticized waistband 35 comprises a shaping panel zone 136; a waistline panel zone 138; and a predisposed, resilient, waistband flexural hinge zone 140 joining the shaping panel zone 136 and the waistline panel zone 138.

The shaping panel zone 136 is the portion of the elasticized waistband 35 that is positioned between the waistband flexural hinge zone 140 and the second flexural hinge zone 134. The shaping panel zone 136 thus will typically define the "lower segment" of the elasticized waistband 35. The shaping panel zone 136 is elastically extensible in at least the lateral direction to allow dynamic expansion and contraction of the elasticized waistband during use. The shaping panel zone 136, as later discussed, also preferably has a relatively significant edge compression stiffness so that the shaping panel zone 136 will not rope, deform, or compact in use and so that the shaping panel zone 136 will maintain its shape to resist compression and buckling of the elasticized waistband during use.

The waistline panel zone 138 is the portion of the elasticized waistband 35 that is positioned toward the end edge of the diaper from the waistband flexural hinge zone 140. The waistline panel zone 138 thus will generally define the "upper segment" of the elasticized waistband 35. The waistline panel zone 138 will preferably form at least a portion of the end edge of the diaper 20. The waistline panel zone 138 is designed to snugly fit against the waist of the wearer and to dynamically move, expand, and contract with the waist of the wearer. The waistline panel zone 138 is elastically extensible in at least the lateral direction.

The edge compression stiffness of the shaping panel zone 136 and the waistline panel zone 138 determines the resistance generally of the elasticized waistband 35 to compression deformation and bending in each zone. In a preferred embodiment of the present invention, the shaping panel zone 136 has a substantial, predetermined, edge compression stiffness to allow the shaping panel zone to resist compression and bending forces applied to it and to maintain the shape of the elasticized waistband when applied to the wearer. Also, the shaping panel zone 136 preferably has an edge compression stiffness greater than or equal to the edge compression stiffness of the waistline panel zone 138. In a preferred embodiment of the present invention, since the shaping panel zone 136 and the waistline panel zone 138 are constructed of the same materials, the edge compression stiffness of the shaping panel zone 136 is about equal to the edge compression stiffness of the waistline panel zone 138. It has been found that the shaping panel zone 136 preferably has an edge compression stiffness greater than about 100 grams$_f$, more preferably greater than about 115 grams$_f$, most preferably greater than about 130 grams$_f$. Typically, in preferred embodiments of the present invention, the edge compression stiffness of the shaping panel zone 136 is between about 130 and about 110 grams$_f$. The edge compression stiffness of a panel zone of the elastic waist feature 34 can be determined using the method as hereinafter described.

The waistline panel zone 138 is resiliently/flexurally joined with the shaping panel zone 136 by the waistband flexural hinge zone 140. As used herein, the term "resiliently/flexurally joined" means a joint between panel zones or a panel zone and the containment assembly adapted to allow relative flexural bending between the panel zones when forces are applied that provides a restoring force/moment to resiliently return the panel zones to essentially their preceding configuration when the forces are removed. This restoring force/moment is important in the functioning of the elasticized waistband 35 so that the shaping panel zone 136 and the waistline panel zone 138 will assume their preceding in-use (pretensioned) configuration so that the elasticized waistband dynamically follows the waist of the wearer with little slipping relative to the wearer during the entire time of wearing, and does not allow the elasticized waistband to disfunctionally crumple or foldover in a manner that alters its intended functionality during use.

The waistband flexural hinge zone 140 is resilient to allow flexural bending between the shaping panel zone 136 and the waistline panel zone 138 when forces generated by the waist of the wearer during use are applied and to return the shaping panel zone 136 and the waistline panel zone 138 to essentially their preceding in-use (pretensioned) configuration when these forces are removed by providing a restoring force/moment. In a preferred embodiment shown in FIGS. 1–3, the waistband flexural hinge zone 140 is constructed to be resilient by providing a resilient member 77 in the elasticized waistband 35. It has been found that in order to provide the necessary resiliency for the waistband flexural hinge zone and to overcome the normal forces encountered during wear of the diaper so as to reduce rollover or roll-in, the waistband flexural hinge zone 140 should have a bending flexure restoring force greater than about 20 grams$_f$, more preferably greater than about 25 grams$_f$, and most preferably greater than about 30 grams$_f$. In preferred embodiments of the present invention, the waistband flexural hinge zone will have a bending flexure restoring force between about 30 grams$_f$ and about 50 grams$_f$. A method for measuring the bending flexure restoring force of a flexural hinge zone, particularly the waistband flexural hinge zone, is hereinafter described.

The waistband flexural hinge zone 140 is also "predisposed" so that the waistline panel zone 138 and the shaping panel zone 136 will flexurally bend at a defined zone or axes in the elasticized waistband 35 for each given application of force to the elasticized waistband 35. This predisposition of the waistband flexural hinge zone 140 also allows the elasticized waistband to flexurally deflect and follow the waist of the wearer without creasing or destroying the flexural rigidity of the materials making up the elasticized waistband. Thus, a "predisposed" waistband flexural hinge zone will reduce the tendency for the elasticized waistband to bend or fold at random zones or axes during use. The "predisposed" waistband flexural hinge zone is defined by the manufacturer of the diaper to ensure flexural bending deflection at the defined hinge zone. The formation of the waistband flexural hinge zone 140 itself typically predisposes the axes or zone of flexural bending within the elasticized waistband 35. As previously discussed, a flexural hinge zone may comprise a zone of structural discontinuity or a zone of material discontinuity. These zones of discontinuity will define the axis of flexural bending. As an example, the waistband flexural hinge zone 140 may comprise an axes or line created by embossing, creasing, or folding the elasticized waistband along a defined line. For instance, the elasticized waistband could be prefolded by the manufacturer inside of the packaging for the article to preshape or preform a waistband flexural hinge zone in the elasticized waistband. A line of reduced extension (or the reverse of a line being extensible and the surrounding areas being nonextensible) may be provided to form the waistband flexural hinge zone by providing spaced apart bands or lines of glue, thread, or other materials that provide a structural discontinuity between them in order to predispose the waistband flexural hinge zone. A change in the lamination or bonding pattern or technique may also form the waistband flexural hinge zone. Any of the other ways of creating a flexural hinge zone previously discussed herein may also be used to form the waistband flexural hinge zone.

In a preferred embodiment as shown in FIGS. 1 and 2B, the waistband flexural hinge zone 140 is formed by a structural discontinuity between the shaping panel zone 136 and the waistline panel zone 138. As shown in FIG. 28, the materials forming the elasticized waistband 35 are secured to each other at transverse regions of securement 78 preferably comprising a pattern of discrete, spaced, securement zones 79, most preferably the securement zones comprising dynamic mechanical bonds. Due to the combined effect of the bonding pattern and the formation of pleats in the waistband, the elasticized waistband 35 will tend to more readily flexurally bend along the region in the pattern where there are fewer bonds. Thus, the pattern for the dynamic mechanical bonds, as shown in FIG. 28, is designed as longitudinally staggered but overlapping rows such that a lateral line moved longitudinally along the elasticized waistband will encounter the bonds except at the desired location of the waistband flexural hinge zone. Thus, the waistband flexural hinge zone 140 preferably comprises (is formed by) a discontinuity in the pattern of the spacing of the securement zones 79.

The elasticized waistband 35 may be constructed in a number of different configurations including those described herein with regard to forming an elasticized side panel. In a preferred embodiment as shown in FIG. 2, the elasticized waistband 35 preferably is constructed from four materials laminated together. The elasticized waistband 35 preferably comprises a portion of the topsheet 24; a portion of the backsheet 26, this portion of the backsheet being preferably "mechanically prestrained"; an elastomeric member 76; and a resilient member 77. The elastomeric member 76 and the resilient member 77 are preferably joined together, preferably by dynamic mechanical bonds, to form an elastic laminate prior to being combined with the topsheet 24 and the backsheet 26. This bi-laminate is preferably positioned between the topsheet 24 and the backsheet 26 with the resilient member 77 disposed toward the backsheet 26 and the elastomeric member 76 disposed toward the topsheet 24. Thus, the elastomeric member 76 is preferably positioned between the topsheet 24 and the prestrained backsheet 26 with the resilient member 77 preferably being positioned between the prestrained backsheet 26 and the elastomeric member 76.

The elastomeric member 76 is operatively associated with the elasticized waistband 35, preferably between the topsheet 24 and the backsheet 26, so that the elastomeric member 76 allows the elasticized waistband 35 to be elastically extensible in the lateral direction (i.e., laterally elastically extensible), and so that it can contractively return to its substantially unrestrained configuration. The elastomeric member 76 can be operatively associated in the elasticized waistband 35 in a number of different ways. As an example, the elastomeric member may be operatively associated in an elastically contractible condition so that the elastomeric member gathers or contracts the elasticized waistband. (A more detailed description of the manner in which elastomeric materials may be secured in an absorbent article in an elastically contractible condition can be found in U.S. Pat. No. 3,860,003 issued to Buell on Jan. 14, 1975, and in U.S. Pat. No. 4,081,301 issued to Buell on Mar. 28, 1978; both patents being incorporated herein by reference.) For example, the elastomeric members 76 can be contractibly affixed in the elasticized waistband 35 by laterally extending the elastomeric member 76, affixing the elastomeric member 76 to either or both the topsheet 24 and the backsheet 26, and allowing the elastomeric member 76 to assume its relaxed or contracted orientation.

Alternatively, the elastomeric member 76 can be operatively associated in the elasticized waistband 35 by securing the elastomeric member 76 to the topsheet 24, the backsheet 26, or both while the elastomeric member 76 is in a substantially untensioned condition, at least a portion of the laminate containing the elastomeric member 76 then being subjected to mechanical stretching sufficient to permanently elongate the topsheet 24 and the backsheet 26 components of the laminate, and then the composite or elastomeric laminate is returned to its substantially untensioned condition. The elasticized waistband 35 is thus formed into a "zero strain" stretch laminate. (As discussed hereinafter, the elastomeric laminate may alternatively be operatively associated in a tensioned condition and subjected to mechanical stretching to form a mechanically stretched, pretensioned, stretch laminate.)

In an especially preferred embodiment as shown in FIG. 2, the elastomeric member 76 can be operatively associated in an uncontracted state and then treated to contract. In this embodiment, the elastomeric member 76 can be formed from materials which contract unidirectionally and become elastic following specific treatment such as heating. Examples of such materials are disclosed in U.S. Pat. No. 3,819,401 issued to Massengale, et al. on Jun. 25, 1974 and in U.S. Pat. No. 3,912,565 issued to Koch, et al. on Oct. 14, 1975. A more detailed description of a manner for using a heat-shrinkable elastomeric member is described in U.S. Pat. No. 4,515,595 issued to Kievit and Osterhage on May 7, 1985; this patent being incorporated herein by reference. Typically, the topsheet 24, the backsheet 26, the elastomeric member 76, and any other components are secured together while in an uncontracted condition. The laminate is then heated (as with heated air) and the elastomeric member 76 is allowed to return to its relaxed or contracted orientation.

The elastomeric members useful in the present invention may take on a number of different sizes, shapes, configurations, and materials. For example, the elasticized waistband may be formed from one or a plurality of elastomeric members operatively associated between the topsheet and the backsheet; the elastomeric member may have varying widths and lengths; or the elastomeric member may comprise relatively narrow strands of elastomeric material or a larger area patch of elastomeric material. One elastomeric material which has been found to be suitable for use as the elastomeric member is an elastomeric foam such as the polyurethane foam such as is available from Bridgestone of Yokahama, Japan and designated Bridgestone SG Polyurethane Foam. Other suitable elastomeric materials for use as the elastomeric member include "live" synthetic or natural rubber, elastomeric films (including heat-shrinkable elastomeric films), formed elastomeric scrim, or the like. In an especially preferred embodiment as is shown in FIG. 2, the elastomeric member 76 comprises a heat-shrinkable elastomeric film such as marketed by Exxon Chemical Company of Florham Park, N.J.

The resilient member 77 is a layer or layers that provides enhanced shape recovery and bending stiffness to the elasticized waistband 35. The resilient member 77 provides compression/buckling resistance in the longitudinal direction (machine direction) so that the waistband flexural hinge zone 140 will be resilient so as to provide a restoring force/moment. The resilient member 77 also has a relatively high caliper to provide a Z-direction bulk so as to somewhat fill the pleats 80 or rugosities of the elasticized waistband 35 so as to optimize its resiliency. The resilient member 77 is also preferably hydrophobic to prevent wicking of liquids out of the elasticized waistband 35. In an especially preferred embodiment, the resilient member 77 comprises a nonwoven material in which the fibers are oriented in the machine direction (longitudinal direction of the diaper) to reduce cross machine direction (lateral) gather resistance so that the heat shrinkable elastomeric member can readily contract and to enhance the compression resistance about a defined axes of bending, the waistband flexural hinge zone 140.

While the resilient member 77 is preferably positioned between the elastomeric member 76 and the backsheet 26 as shown in FIG. 3, the resilient member 77 may alternatively be positioned between the topsheet 24 and the elastomeric member 76, on the outside of the backsheet 26, on the outside of the topsheet 24, or in a number of other configurations. The resilient member 77 is preferably positioned between the backsheet 26 and the elastomeric member 76 to provide greater compression/buckling resistance on the backsheet side of the elasticized waistband 35 since it will fill the rugosities or pleats 80 in the longitudinal axis between the bond sites, for providing bending resistance about the lateral axis of the elasticized waistband, and to optimize and reduce wicking in the laminate material forming the elasticized waistband.

The resilient member 77 may take on a number of different sizes, shapes, configurations, and materials. For example, the resilient member may be formed from one or a plurality of resilient members; the resilient member may have varying widths, lengths, thickness, and shapes. The resilient member 77 preferably comprises a separate piece of material positioned in the elasticized waistband. Alternatively, the resilient member may comprise a portion of any or all of the materials making up the elasticized waistband 35, including the elastomeric member 76, the topsheet 24, or the backsheet 26. In a particular alternative embodiment, the resilient member 77 comprises the same piece as the elastomeric member 76, the elastomeric member 76 comprising a relatively thick elastomeric foam.

Suitable materials for use as the resilient member 17 of the elasticized waistband 35 of the present invention include woven webs; nonwoven webs; foams; laminate materials including film laminates of nonwoven laminates of two or more nonwoven layers; scrims; corrugated materials that provide stiffness in at least one direction; and any combination of the above materials or other materials as Are known in the art.

Particularly preferred materials for the resilient member 77 comprise nonwoven webs that are hydrophobic and that have a drapability (as measured using ASTM B1388-64) of at least about 4 cm in the cross machine direction and At least about 12 cm in the machine direction. An exemplary material comprises a hydrophobic, nonwoven carded web having a basis weight in the range of from about 20–45 grams per square yard. The fibers are oriented in the machine direction to provide enhanced buckling/compression resistance in this direction. The nonwoven web 1s comprised of 3 denter bicomponent fibers of polyester core material and copolyolefin sheathing material, such fibers being available from Hoecht as CELBOND stable fibers; or of a polypropylene core material and polyethylene sheathing material, such fibers being available from Danaklon or Hercules. After carding the nonwoven web to orient the fibers in the machine direction, the nonwoven web is put through an air-thru bonding process to provide bulk (loft or thickness) to the resilient member to enhance its resiliency. (Examples of high loft nonwoven webs of bicomponent thermoplastic resin fibers that are air-thru bonded are disclosed in U.S. Pat. No. 4,883,707 issued to Newkirk on Nov. 28, 1989, and incorporated herein by reference.) Exemplary air-thru bonded nonwoven carded webs of bicomponent thermoplastic fibers are available from FiberWeb North America of Greenville, N.C. or from Veratec Corporation of Walpole, Mass.

In a preferred embodiment of the present invention as shown in FIG. 2A, the portion of the backsheet 26 forming the elasticized waistband 35 has been "prestrained" or "mechanically prestrained" (i.e., subjected to some degree of localized pattern mechanical stretching to permanently elongate those portions of the backsheet forming the elasticized waistband 35). A prestrained backsheet improves not only the extension of the elastomeric member 76 but also the heat-shrink contraction of the preferred elastomeric members 76. In a preferred embodiment as shown in FIG. 2A, the prestrained backsheet assumes a pattern of ribs 142 (strained portions) and unstrained gaps 144 between each rib 142 and between each row of ribs. This pattern is determined by the method and apparatus used to prestrain the backsheet. In this preferred embodiment, the ribs are 0.25 inch (about 6 long, 0.030 inch (about 0.75 mm) wide, have a depth of 0.125 inch (about 3 mm), with a spacing between each rib (gap) of 0.100 inch (about 2.5 mm). The area of the backsheet that is prestrained is preferably about 5.5 inches (about 140 mm) wide by about 1 inch (about 25 mm) in length.

The backsheet 26 of the present invention can be prestrained by directing the backsheet through an Incremental mechanical stretching system similar to the operation described herein with respect to the formation of the "zero strain" stretch laminate elasticized side panels 30, prior to combining the backsheet into the finished diaper product. The corrugated or grooved segments contained on the rolls are Interrupted to bring about the pattern of ribs in the machine direction and the cross-machine direction. The registration of the web of the backsheet is such that the portion of the backsheet to be prestrained substantially coincides with the corrugated or grooved segments contained on the uppermost corrugated rolls as the backsheet passes between the segments of the uppermost corrugated rolls and the corrugated or grooved lowermost corrugated rolls. The backsheet can alternatively be prestrained by using deep embossing techniques as are known in the art.

In a preferred method for making the diapers of the present invention, after the backsheet web has been prestrained, and after the backsheet web has been removed from the corrugated combining rolls, a continuous spray glue is applied to the backsheet web. The elastic laminate comprising the resilient member and the heat-shrinkable elastomeric member 1s dynamically mechanically bonded with the topsheet. The resulting topsheet/elastomeric member/resilient member laminate is then applied to the prestrained backsheet web of the diaper and dynamically mechanically bonded together to form the elasticized waistband 35. This diaper web is then passed to a heat shrink apparatus to contract the heat shrinkable elastomeric member.

The elasticized waistband 35 further comprises transverse regions of securement 78 shown in a generalized representation in FIG. 1 and in FIG. 2. A more detailed description of the transverse regions of securement and alternative configurations for them are found in U.S. Pat. No. 4,515,595 issued to Kievit and Osterhage on May 7, 1985, and which patent is incorporated herein by reference. The transverse regions of securement 78 extend essentially across the full width of the elasticized waistband 35, particularly the elastomeric member 76. The term "essentially across" is used in this context to indicate that the transverse regions of securement need not extend absolutely across the entire width of the elastomeric member 76 so long as they extend sufficiently far across the width to provide the function discussed hereinafter. As illustrated, the transverse regions of securement 78 are shown to be disposed at essentially a right angle to the lateral centerline 66 and to the lateral extent of the elasticized waistband 35. This is the preferred orientation. One can, however, depart from true transversity without departing from the scope and spirit of the invention.

In FIGS. 1 and 2B, the transverse regions of securement 78 are shown as discrete, spaced, securement zones 79 effectively attaching the webs of material forming the elasticized waistband 35 (the topsheet 24, the backsheet 26, the resilient member 77, and the elastomeric member 76 in a preferred embodiment) together. While the shape of the discrete securement zones may vary, the discrete securement zones 79 are preferably circular, elliptical, oval, rectangular, or square shaped. The discrete securement zones 79 are preferably regularly spaced in a pattern (as shown in FIG. 2B) (except where the waistband flexural hinge zone 140 is formed), although they can be nonuniformly spaced. The precise means for providing the securement zones 79 can be readily selected by those skilled in the art. Examples of such attachment means include adhesive attachment, heat sealing, solvent sealing, autogeneous bonding, dynamic mechanical bonding, ultrasonic welding, and the like. Preferably, the transverse regions of securement 78 comprise oval (rounded rectangular) shaped discrete securement zones 79, preferably dynamic mechanical bonds, such as described in U.S. Pat. No. 4,919,738 entitled "Dynamic Mechanical Bonding Method And Apparatus" which issued to Ball, Goulait & Zorb on Apr. 24, 1990, and which patent is incorporated herein by reference, disposed in rows and columns with one column missing or irregularly spaced to form the waistband flexural hinge zone 140. The securement zones 79 are preferably from about 2.0 mm (about 0.078 in) by about 1.3 mm (about 0.52 in) and are preferably spaced from about 7.0 mm (0.275 in) to about 8.9 mm (0.375 in) from center to center in the transverse direction and from about 1.9 mm (0.375 in) to about 3.8 mm (0.15 in) from center to center in the longitudinal direction. (One row of bond sites are eliminated in each column such that there is a longitudinal gap of about 1.0 mm (about 0.040 in) to about 3.8 mm (0.150 in) from center to center to form the waistband flexural hinge zone 140.) In the most preferred embodiment, the securement zones 79 are spaced about 8.3 mm (0.325 in) from center to center in the transverse direction and about 2.8 mm (0.112 in) from center to center in the longitudinal direction with an offset gap spacing of about 0.71 mm (0.028 in) from center to center between adjacent rows in the longitudinal direction.

As illustrated in FIG. 2, the discrete securement zones 79 on either side of the elastomeric member 76 are in register (i.e., they are coextensive). This is a preferred orientation, but the discrete securement zones 79 of the topsheet 24 to the elastic laminate material can be offset from the adjacent discrete securement zones 79 of the backsheet 26 to the elastic laminate material.

In an alternative embodiment, the elasticized waistband in the second waist region 58 (or the first waist region 56 if elasticized side panels are disposed therein) and the elasticized side panels 30 can be formed by securing a single piece of elastomeric material to the diaper 20 in both the side panels 72 and the central region 68 of the second waist region 58. Thus, the elasticized waistband 35 and the elasticized side panels 30 can be formed from the same piece of material to form a unitary structure. An example of such an elasticized waistband/side panel configuration is disclosed in the hereinbefore referenced U.S. Pat. No. 4,887,067 issued to Wood, et al. on Aug. 15, 1989, and which patent is incorporated herein by reference.

In a further alternative embodiment of the present invention, the elasticized waistband 35 may have differential extensibility along the longitudinal axis when stretched in the lateral direction. The differential extensibility of the elasticized waistband 35 allows portions to laterally expand to a greater degree than other portions along the longitudinal axis. This differential extensibility of the elasticized waistband provides an abdominally compliant elasticized waistband, "expansive tummy panel", that allows the elasticized waistband to differentially shape, expand and move with the stomach of the wearer as the wearer moves, sits, and stands. Differential extensibility along the longitudinal axis when stretched in the lateral direction of the elasticized waistband can be achieved in a number of ways such as is discussed with respect to the elasticized side panels 30. As shown in FIG. 6, a preferred differential extensibility elasticized waistband has a pentagonal shape.

The diaper 20 is also preferably provided with a closure system (tensioning means) for dynamically creating/maintaining lateral tension through the elasticized waistband 35. The lateral tension dynamically created and maintained by the closure system "activates" the stretch of the elasticized waistband 35 thereby allowing it to more dynamically expand and contract with the motions of the wearer. Gapping of the elasticized waistband is also reduced by the activated stretch since it is held in tension to snugly fit against the wearer's waist both when the diaper is initially fitted to the wearer and during use. Further, rollover of the elasticized waistband is reduced by the tension created/maintained by the closure system. Thus, the closure system improves the fit and containment characteristics of the diaper.

While the closure system may take on a number of configurations such as adhesive tape tabs, mechanical closure tape tabs, fixed position fasteners, or any other means for tensioning the elasticized waistband as are known in the art; as shown in FIG. 1, the closure system preferably comprises a waist closure system 40 comprising at least one, typically a pair of, first attachment components 46 and at least one second attachment component 48. More preferably, the closure system additionally comprises a primary fastening system 38 such that the diaper 20 has a dual tension fastening system 36. Preferred embodiments of a diaper having a dual tension fastening system are described in commonly assigned, co-pending, U.S. patent application, P&G Case 4412, Well et al., "Absorbent Article With Fastening System Providing Dynamic Elasticized Waistband Fit", filed concurrently herewith; the specification and drawings of which are incorporated herein by reference.

The dual tension fastening system 36 forms both a side closure and a waist closure. The dual tension fastening system 36 thus comprises a primary fastening system 38 for providing the side closure and a waist closure system 40 for providing the waist closure. The primary fastening system 38 maintains the first waist region 56 and the second waist region 58 in an overlapping configuration such that lateral tensions are maintained around the circumference of the diaper to maintain the diaper on the wearer. The waist closure system 40 forms a waist closure that dynamically maintains/creates lateral tensions through the elasticized waistband 35 so as to improve the fit and containment characteristics of the diaper 20 by reducing gapping, sagging, and rollover of the elasticized waistband 35.

As shown in FIG. 1, the primary fastening system 38 comprises a securement member 42 disposed adjacent each longitudinal edge 62 in the second waist region 58, and at least one landing member 44 disposed in the first waist region 56 so as to form a portion of the outer surface 52. Each securement member 42 preferably comprises a tape tab 92 and a first fastening component 112. The landing member 44 preferably comprises a complementary second fastening component 114 engageable with the first fastening component 112 of the securement member 42. An exemplary primary fastening system wherein the first and second fastening components each comprise mechanical closure elements comprising hook and loop fastening materials is disclosed in U.S. Pat. No. 4,869,724 entitled "Mechanical Fastening Systems With Adhesive Tape Disposal Means For Disposable Absorbent Articles" issued to Scripps on Sep. 26, 1989. Primary fastening systems utilizing mechanical closure elements are also disclosed in U.S. Pat. No. 4,846,815 entitled "Disposable Diaper Having An Improved Fastening Device" issued to Scripps on Jul. 11, 1989; and U.S. Pat. No. 4,894,060 entitled "Disposable Diaper With Improved Hook Fastener Portion" issued to Westegard on Jan. 16, 1990. A primary fastening system having combination adhesive/mechanical closure elements is described in U.S. Pat. No. 4,946,527 entitled "Pressure-Sensitive Adhesive Fastener And Method of Making Same" issued to Battrell on Aug. 7, 1990. Each of these patents are incorporated herein by reference. In a preferred embodiment of the present invention as is shown in FIG. 1, the primary fastening system 38 comprises an adhesive tape tab fastening system comprising a tape tab 92 having an adhesive attachment layer 96 and a landing member 44 comprising a reinforcing strip 116 joined to the backsheet 26. Examples of such adhesive tape tab fastening systems are disclosed in U.S. Pat. No. 3,848,594 entitled "Tape Fastening System for Disposable Diaper" issued to Buell on Nov. 19, 1974; and the adhesive tape tabs, reinforcing strip, and indicia means disclosed in U.S. Pat. No. B1 4,662,875 entitled "Absorbent Article" issued to Hirotsu and Robertson on May 5, 1987. Each of these patents are incorporated herein by reference.

Each securement member 42 of the primary fastening system 38 is intended to provide a fastening means for engaging the landing member 44 so as to provide a secure, preferably a variable positioning, side closure for the diaper 20. Thus, the securement member 42 comprises at least one fastening component. Each securement member 42 also preferably comprises a means for positioning the fastening component adjacent the landing member 44 so as to achieve an optimum fitting side closure. Thus, the securement member 42 may comprise any of the well known configurations and means for achieving a side closure on a diaper such as (i) a patch or strip of a fastening component disposed to form a portion of the inner surface of the diaper or (ii) a tape tab having a fastening component positioned thereon.

As shown in FIG. 1, each securement member 42 preferably comprises a tape tab 92. Any of the well known configurations and constructions of a tape tab may be used in the present invention. For example, an exemplary tape tab is described in detail in the hereinbefore referenced U.S. Pat. No. 3,848,594 issued to Buell on Nov. 19, 1974, and which patent is incorporated herein by reference. A particularly preferred tape tab 92 has a fastening surface 98 and a backing surface 99. The fastening surface 98 is that surface of the tape tab 92 designed to engage the landing member 44 of the present invention. Thus, the fastening surface 98 of the tape tab 92 is generally oriented to face the inner surface 54 of the diaper 20. The backing surface 99 is that surface opposed to the fastening surface 98 and generally faces the outer surface 52 of the diaper 20. The backing surface 99 is thus generally exposed during wear of the diaper 20.

The preferred tape tab 92 is one which is joined to the backsheet 26 of the diaper 20 to create a fixed portion 93 (i.e., that end of the tape tab 92 joined to the diaper 20 during manufacture). The tape tab 92 has another element which is the tab portion 94 (i.e., that end of the tape tab 92 that extends outwardly beyond the longitudinal edge 62 of the diaper 20 and that is grasped by the diaperer in securing the diaper on the wearer). The distal edge 97 of the tape tab 92 preferably has rounded corners to eliminate the possibility of harsh corner edges contacting the wearer's skin so as to prevent stomach red marking. The preferred tape tab 92 of the present invention also comprises a release portion 95 joined to the topsheet 24 of the diaper 20. The release portion 95 allows the tab portion 94 to be inwardly folded during manufacture to protect the adhesive attachment layer 96 from contamination or delamination prior to use. The release portion 95 extends inwardly from the longitudinal edge 62 of the diaper 20 preferably up to and juxtaposed over a portion of the elastic side panel member 90 so that the load carried by the tape tab 92 is transferred into the elastic side panel member 90 resulting in more effective distribution of the loads (wearing stresses). The tab portion 94 is also preferably shorter in the lateral direction (width) than the release portion 95 so that it is easier for the diaperer to initially grasp the tab portion 94.

The fastening component of the securement member 42 forms the closure between the securement member 42 and the complementary fastening component of the landing member 44. Thus, the fastening component provides a means for engaging the complementary fastening component of the landing member 44 to maintain the first waist region 56 and the second waist region 58 in an overlapping configuration to provide a secure side closure for the diaper 20. Further, it is preferred that a diaper fit a range of different size wearers and that the fastening system be simple and easy to use. Therefore, the fastening components should allow for variable positioning of the zone of closure so that the diaper may fit a range of sizes while also being simple to fasten with minimal effort. The fastening components thus comprise any of the well known attachment means for achieving an adjustable positioning secure closure as defined hereinafter. Examples of such adjustable positioning attachment means include an adhesive attachment layer such as a pressure-sensitive adhesive as are known in the art, a mechanical closure element such as a hook fastening material or a loop fastening material, any cohesive materials as are known in the art, or a combination of an adhesive/mechanical closure element, as hereinafter described with respect to the waist closure system 40.

The fastening component is disposed on the securement member 42 such that it may be a separate member joined to and associated with the securement member 42 or a unitary member with the securement member 42. For example, the topsheet 24 or the backsheet 26 may be manufactured from a material that mechanically engages the landing member 44 (the topsheet 24 or the backsheet being a unitary fastening component). Alternatively, a discrete patch or strip of material may be joined to the securement member 42 (a separate fastening component). Preferably, the first fastening component 112 is a separate material, such as an adhesive attachment layer or a mechanical closure element, positioned on and joined to the tape tab 92. The first fastening component 112 preferably comprises an adhesive attachment layer coated on the tab portion 94 to form the fastening surface In addition, the first fastening component 112 may be positioned anywhere on the securement member 42. For example, the first fastening component 112 may be positioned in the side panels 72 of the second waist region $8 adjacent the longitudinal edges 62. (Exemplary examples of this construction are shown in U.S. Pat. No. 4,610,682 issued to Kopp on Sep. 9, 1986; and in U.S. Pat. No. 3,141,161 issued to Ferris on Jul. 21, 1964; each of which are incorporated herein by reference.) When the securement member 42 comprises a tape tab 92, the first fastening component 112 is preferably positioned either on all of or at least a portion of the fastening surface 98 of the tab portion 94. The first fastening component 112 may comprise a combination adhesive/mechanical closure element having an adhesive attachment layer and a mechanical closure element disposed on another area of the tab portion 94 on the fastening surface 98 and adjacent the distal edge 97 of the tape tab 92. An exemplary embodiment of this configuration is disclosed in the hereinbefore referenced U.S. Pat. No. 4,869,724 entitled "Mechanical Fastening Systems With Adhesive Tape Disposal Means For Disposable Absorbent Article" issued to Scripps on Sep. 26, 1989, which is incorporated herein by reference.

The landing member 44 of the primary fastening system 38 provides a means for securing itself to the securement member 42 to provide a side closure and to maintain the first waist region 56 and the second waist region 58 in an overlapping configuration. The landing member 44 may be disposed anywhere on the diaper 20 so long as it can engage the securement member 42 so as to provide the side closure and, preferably a variable positioning side closure. For example, the landing member 44 may be disposed so as to form a portion of the outer surface 52 in the first waist region 56, so as to form a portion of the inner surface 54 in the second waist region 58, or on any other portion or element of the diaper 20 which is disposed to engage the securement member 42. Because the landing member 44 determines the approximate location of where the securement member 42 should be placed for optimum fit, the landing member 44 is preferably positioned so as to achieve variable positioning of the side closure so that the diaper may fit a range of sizes, so that an overlap between the first waist region 56 and the second waist region 58 is achieved, and so that when the side closure is formed the attachment components of the waist closure system 40 engage each other such that the formation of the side closure also passively forms the waist closure. The landing member 44 is preferably centered about the longitudinal centerline 67 in the first waist region 56 and extends laterally outwardly to almost the longitudinal edges 62, The landing member 44 may either be a discrete, separate element or elements joined to the diaper 20 or a unitary piece of material with an element of the diaper 20. The landing member 44 may thus comprise, for example, the topsheet 24 or the backsheet 26. While the landing member 44 can assume varying sizes and shapes, it preferably comprises one or more patches of material joined to the backsheet 26 in the first waist region 56 that allows for maximum fit adjustment of diaper 20 to the wearer. In a preferred embodiment of the diaper 20 as illustrated in FIG. 1, the landing member 44 has an elongate, rectangular-shape and is secured to the backsheet 26 in the central region 68 of the first waist region 56 by an adhesive attachment means (not shown) as have been previously discussed. The landing member 44 comprises a fastening component (second fastening component 114) engageable with the fastening component of the securement member 42 (first fastening component 112). Thus, the fastening component of the landing member 44 (second fastening component 114) may be manufactured from a wide range of materials and configurations capable of securely engaging the fastening component of the securement member 42 (first fastening component 112).

When the first fastening component 112 of the securement member 42 comprises an adhesive attachment layer 96, the second fastening component 114 of the landing member 44 preferably comprises a reinforcing strip 116 and/or the backsheet 26. When the first fastening component 112 of the securement member 42 comprises a mechanical closure element, the second fastening component 114 also comprises a mechanical closure element. Thus, when the first fastening component 112 comprises a hook fastening material, the second fastening component 114 preferably comprises a loop fastening material.

In a preferred embodiment of the present invention as shown in FIG. 1, the landing member 44 preferably comprises a reinforcing strip 116 releasably engageable with the adhesive attachment layer 96 of the tape tabs 92. The reinforcing strip 116 may comprise any of a number of configurations and materials secured to the backsheet 26 of the diaper 20. The reinforcing strip 116 is preferably a separate member secured to the backsheet 26 to form a portion of the outer surface 52 of the diaper 20. A preferred reinforcing strip 116 comprises a sheet of biaxially oriented polypropylene film.

The reinforcing strip 116 is also preferably provided with indicia means 118 for aiding the diaperer in fitting the diaper to a wearer to obtain optimal waist fit and leg opening fit. The indicia means 118 may be any type of lines, patterns, ornamental designs, symbols, script, color codes, or other markings which have the capability, either inherently or with additional denotation, to aid an individual fitting the diaper to the wearer to promptly locate the desired affixation points for a particular tape tab fastener. Such indicia means 118 are more fully described in U.S. Pat. No. B1 4,662,875 entitled "Absorbent Article" which issued to Hirotsu and Robertson on May 5, 1987 and which is incorporated herein by reference. Indicia means of the present invention are preferably a combination of different geometric shapes, colors, and objects such as SESAME STREET or DISNEY characters.

The dual tension fastening system 36 additionally comprises a waist closure system 40 for providing a waist closure adjacent the end edge 64 of the diaper 20. The waist closure anchors a portion of the span of the end edge 64. Further, when the diaper 20 comprises an elasticized waistband 35, the waist closure dynamically creates/maintains lateral tensions through the elasticized waistband 35.

The waist closure anchors a portion of the span of the end edge 64 of the diaper 20, preferably a portion of the extensible span of the elasticized waistband 35. (i.e., The first and second attachment components of the waist closure system 40 act to anchor the positional relationship of the elasticized waistband 35 with the elasticized side panels 30.) The term "anchor" is used herein to mean that the attachment components provide an adjustable positioning fastener that achieves a closure with sufficient shear resistance so that there is little or no shear slippage or movement between the attachment components once the closure is achieved. The positional relationship of the elasticized waistband 35 with the elasticized side panels 30 (i.e., the geometric relationship between the anchor zones of the first attachment components 46) establishes a defined waist circumferential dimension adjacent the end edge 64 of the diaper 20 which is distinct (longitudinally spaced) from the circumferential dimension established by the side closure formed by the primary fastening system 38. This distinct, defined waist circumferential dimension creates/maintains the required fit dimension(s) at the upper extremities (adjacent the end edge 64) of the diaper 20. Thus, the waist closure system 40 of the present invention can also be beneficial for use on diapers not employing an elasticized waistband (e.g., a waistshield or a nonextensible waist feature) so as to maintain a nonextensible fit at the end edge 64 (upper edge) of the diaper 20. The anchoring also provides a means for transferring shear forces (tensions) between the elasticized waistband 35 and the elasticized side panels 30 so as to enhance the initial pretension created within the elasticized waistband 35.

The waist closure also creates/maintains lateral tension(s) through the elasticized waistband 35. The waist closure contributes some portion of an initial pretension (lateral tension) within the elasticized waistband 35 that allows the elasticized waistband 35 to snugly fit against the wearer's waist when initially fitted. The elasticized waistband 35 maintains, during use, some portion of the pretension created within it by the waist closure. Since the elasticized waistband maintains some portion of the pretension created within it, the elasticized waistband can repeatedly elastically expand or contract with the motions of the wearer so as to snugly sustain the fit of the diaper against the wearer's waist throughout use. In particular, during wearing conditions, the elasticized waistband, in order to follow the movements of the wearer's waist, may have to contract to its untensioned state (i.e., the pretension goes to zero); however, because the attachment components remain engaged, the pretension will be reestablished within the elasticized waistband with further movement and activity by the wearer. (This is in contrast to most conventional elasticized waistbands that are not pretensioned such as to not be able to further contract to dynamically fit the wearer.) This initial pretensioning and maintenance of the tension thus results in reduced gapping and better sustained fit of the elasticized waistband. Further, the lateral tension(s) created/maintained by the waist closure provide restoring forces within the elasticized waistband that reduce or counteract the incidence of waistband "rollover".

Thus, the waist closure system 40 provides a closure about the waist of the wearer to improve the initial and dynamic fit and containment characteristics of the diaper in the waist regions.

As shown in FIG. 1, the waist closure system 40 comprises at least one, preferably a pair of, first attachment component(s) 46 and at least one second attachment component 48. As shown in FIG. 1, the first attachment component(s) 46 are longitudinally aligned with the elasticized waistband 35 so that the lateral tensions dynamically created/maintained by the waist closure system 40 extends in and through the elasticized waistband 35 during use. Further, the attachment components of the waist closure system 40 are longitudinally spaced from the securement members 42 and the landing member 44 of the primary fastening system 38 to provide a distinct, defined waist circumferential dimension for the diaper and two distinct zones of lateral tension(s). The zone of tension created by the primary fastening system 38 secures the garment on the wearer while the zone of tension dynamically created/maintained by the waist closure system 40 dynamically maintains the upper waist closure during wear.

At least two anchor zones 122 are created by the attachment components when the waist closure is formed. These two anchor zones 122 are laterally spaced from each other with all or at least a portion of the elasticized waistband 35 positioned between the anchor zones 122. The lateral spacing of these anchor zones can be achieved in a number of different ways. For example, the lateral spacing between the anchor zones 122 can be fixed by providing the waist closure system 40 with a pair of first attachment components 46 laterally spaced from each other and a second attachment component(s) 48 that allows adjustable positioning with the first attachment components 46 (e.g., the second attachment component(s) is relatively wide). In this embodiment, since the lateral spacing of the first attachment components 46 is fixed, the lateral spacing of the first attachment components 46 determines and sets the lateral spacing of the anchor zones. In an alternative embodiment, the waist closure system 40 may comprise a pair of second attachment components 48 laterally spaced from each other and a first attachment component(s) 46 that allows adjustable positioning with the second attachment components 48 (e.g., the first attachment component 46 is relatively wide). In this embodiment, the lateral spacing of the anchor zones is determined by the size of the waist of the wearer and the overall dimension/shape of the diaper since the location of where the second attachment components 48 engage the first attachment component(s) 46 depends upon the overlap of the side panels in the second waist region 58 with the side panels in the first waist region 56.

The preferred lateral spacing of the anchor zones 122 is designed to allow passive activation of the waist closure when the side closure is formed, and to assure the maintenance of normal forces applied to the waist of the wearer to decrease the tendency of the elasticized waistband 35 to nonrecoverably rollover while providing an effective amount of stretch in the elasticized waistband that improves the fit and containment of the diaper in the waist. In order to maintain normal forces within the elasticized waistband that provide for recovery of the waistband and minimize flipping out of the tensioned waistband (i.e., nonrecoverable rollover), the lateral spacing of the anchor zones would desirably be kept to a minimum. However, in order to provide a maximum amount of stretch in the elasticized waistband, the lateral spacing of the anchor zones would be desirably chosen to be at a maximum. Therefore, the lateral spacing of the anchor zones is thus chosen so as to balance the need for maintaining the normal forces with the need for providing an effective amount of stretch in the elasticized waistband.

In the diaper embodiment shown in FIG. 1 that is designed to fit medium-size (5.4 kg to about 10.8 kg) babies, the lateral spacing between the anchor zones 122 (between the first attachment components 46) is at least about 25 mm. More preferably, the lateral spacing is at least about 50 mm. In the embodiment shown in FIG. 1, the lateral spacing of the first attachment components 46 is most preferably between about 100 mm and about 200 mm. The lateral spacing of the anchor zones 122 is determined by measuring the distance from the innermost line of securement (i.e., that line closest to the longitudinal centerline 67) of one anchor zone to the innermost line of securement of the other anchor zone with the elasticized waistband in its contracted state. Thus, in the embodiment illustrated in FIG. 1, the lateral spacing is determined by measuring the distance from the innermost edge of one of the first attachment components 46 to the innermost edge of the other first attachment component 46.

Each attachment component comprises a fastening means that engages a complementary fastening means for providing a variable positioning, passively activated, waist closure. As used herein, the term "variable positioning" closure refers to a fastening system wherein at least one of the positions of the components can widely vary so as to allow the user to form a closure at a number of different locations. Thus, for example, one of the components may have a fixed location on the diaper (e.g., the lateral spacing between the first attachment components 46 is fixed so as to provide for the pretensioning of the elasticized waistband 35 and the passive activation of the waist closure) while the other component allows for variable locations of attachment to the fixed component. This is in contrast to a "fixed" positioning closure which requires both of the mating elements to be fixed in position such that the components must be joined at a specific location each time the closure is formed (e.g., snaps and buckles). The waist closure system 40 also provides a passively activated waist closure. By "passively activated", it is meant that a functional waist closure is achieved with little or no additional effort by the diaperer after a suitable initial body/leg fit (side closure) is achieved using the primary fastening system 38. Passive activation of the waist closure system 40 requires the attachment components to not only engage each other so as to provide a secure anchor with little or no additional effort but also to be positioned on the diaper in an arrangement that creates/maintains the lateral tensions within the elasticized waistband 35.

As shown in FIG. 1, the attachment components preferably comprise mechanical closure elements. As used herein, the term "mechanical closure elements" describes fastening means which mechanically engage each other for providing a variable-position closure. Thus, the mechanical closure elements may comprise any of the well known means for achieving a variable-position closure by mechanical engagement such as VELCRO or other hook and loop fastening materials.

When the first attachment component 46 comprises a mechanical closure element, the second attachment component 48 may comprise "identical" complementary mechanical closure elements or "distinct" complementary mechanical closure elements. As used herein, the term "identical" complementary mechanical closure elements is used to define mechanical fastening systems wherein the engaging elements of the first component and the second component comprise the same configuration or structure that are interlocking. Examples of such systems are described in U.S. Pat. No. 4,322,875 entitled "Two Strip Materials Used For Forming Fasteners" issued to Brown, et al. on Apr. 16, 1982. The term "distinct" complementary mechanical closure elements is used herein to define mechanical fastening systems wherein the first component is different from the second component but is engageable therewith such as a hook fastening material and a loop fastening material. For example, if the second attachment component 48 comprises a loop fastening material then the first attachment component 46 will comprise a hook fastening material and vice versa.

As used herein, the term "hook fastening material" is used to designate a material having engaging elements. Thus, the hook fastening material may also be referred to as a male fastener. It should also be understood that the use of the term "hook" should be non-limiting in the sense that the engaging elements may comprise any shapes as are known in the art so long as they are adapted to engage a complementary mechanical closure element such as a loop fastening material or another hook fastening material.

The hook fastening material is preferably intended to mechanically engage fibrous elements of a loop fastening material so as to provide a secure closure. Thus, a hook fastening material according to the present invention may be manufactured from a wide range of materials. Suitable materials include nylon, polyester, polypropylene, or any combination of these materials, or other materials as are known in the art. A suitable hook fastening material comprises a number of shaped engaging elements projecting from a backing such as the commercially available material designated "Scotchmate" brand No. FJ3402 available from Minnesota Mining and Manufacturing Company, St. Paul, Minn. Alternatively, the engaging elements may have any shape such as hooks, "T's", mushrooms, or any other shape as are well known in the art. An exemplary hook fastening material is described in U.S. Pat. No. 4,846,815 entitled "Disposable Diaper Having An Improved Fastening Device" issued to Scripps on Jul. 11, 1989, and which patent is incorporated herein by reference.

An especially preferred hook fastening material, as shown in FIG. 1, comprises an array of prongs 120 formed of thermoplastic material. Hot melt adhesive thermoplastics, in particular polyester and polyamide hot melt adhesives, are particularly well suited for forming the prongs of the hook fastening material. The prongs 120 are preferably manufactured using a modified gravure printing process by printing the thermoplastic material in its molten state onto a substrate in discrete units, severing the material in a manner that allows stretching of a portion of the thermoplastic material prior to severance, and allowing the stretched molten material to "freeze" resulting in prongs. This preferred hook fastening material and methods and apparatus for making such a hook fastening material are more fully detailed in European Patent Application 0 381 087; The Procter & Gamble Company; published Aug. 8, 1990, which application is incorporated herein by reference.

A loop fastening material provides a plurality of fibrous elements that engage the engaging elements of a hook fastening material. The loop fastening material may be manufactured from a wide range of materials to provide fibrous elements, preferably loops. Such suitable materials include nylon, polyester, polypropylene, any combination of these materials, or other materials as are known in the art. A suitable loop fastening material comprises a number of fiber loops projecting from a backing such as the commercially available material designated "Scotchmate" brand nylon woven loop No. SJ3401 available from Minnesota Mining and Manufacturing Company, St. Paul, Minn. Another commercially available loop fastening material comprises a tricot knit fabric having a plurality of nylon filament loops projecting from a backing of nylon such as the commercially available material designated "Guilford No. 16110" available from Guilford Hills of Greensboro, N.C. An exemplary inexpensive loop fastening material and a method of making such a loop fastening material are described in European Patent Application 0 289 198; The Procter & Gamble Company, published Nov. 2, 1988, which application is incorporated herein by reference. A suitable loop fastening material may also be a woven or nonwoven fabric or any other type of fibrous material or loop material which are well known in the art. Examples of nonwoven materials suitable for use as a loop fastening material herein are discussed with respect to the materials useful as the topsheet 24 of the diaper 20. In a preferred embodiment, the loop fastening material is formed by the nonwoven material of the topsheet 24.

The attachment components may alternatively comprise an adhesive attachment layer (a layer of adhesive material). Adhesives useful in the present invention are preferably pressure-sensitive adhesives formulated to adhere to a surface at ambient temperature by applying only light pressure. Particularly preferred adhesives for use herein as the adhesive attachment layer are hot melt pressure-sensitive adhesives is are known in the art. An exemplary hot-melt pressure-sensitive adhesive is a Kraton based adhesive with tactfiers and other additives such as marketed by Findley Adhesives, Inc. of Elm Grove, Wis. under the tradename Findley 990 or H-2085.

The attachment components may further comprise a combination adhesive/mechanical closure element. For example, the attachment components may comprise a combination fastener such as hook fastening material and an adhesive attachment layer juxtaposed with the hook fastening material or a mechanical closure element such as a hook fastening material having a layer of adhesive coated over a portion of the hook fastening material. An exemplary fastener having a combination mechanical/adhesive system is the pressure-sensitive adhesive fastener having a textured fastening surface such as is disclosed in U.S. Pat. No. 4,946,527 issued to Battrell on Aug. 7, 1990, which patent is incorporated herein by reference.

The attachment components may alternatively further comprise any other cohesive material or materials that are known in the art for providing a variable positioning fastener capable of being passively activated. For example, a cohesive strip or material can be foams, rubbers such as crepe or latex rubbers, other adhesives, or a high static vinyl material. A separable fastener of a high static vinyl material is more fully described in U.S. Pat. No. 4,979,613 issued to McLaughlin & Kleinsmith on Dec. 25, 1990, which patent is incorporated herein by reference.

The attachment components may comprise a separate element joined to the diaper 20 or may be a unitary element with one of the other components of the diaper. For example, the topsheet may be manufactured from a material (e.g., a nonwoven web), that is capable of mechanically engaging the other attachment component (e.g., a hook fastening material). Further, the backsheet 26 can be formed from a web having a textured pattern with a layer of adhesive coated over a portion of the backsheet surface to form a combination mechanical/adhesive fastener (attachment component) such as is shown in the hereinbefore referenced U.S. Pat. No. 4,946,527 to Battrell. In each of these cases, the attachment component is unitary with another component of the diaper. Alternatively, the attachment component may comprise a discrete strip or patch joined to the diaper. In a preferred embodiment shown in FIG. 1, each first attachment component 46 comprises a discrete separate patch of a hook fastening material joined to the backsheet 26 so as to form a portion of the outer surface 52 while the second attachment component 48 is a unitary element comprising a portion of the topsheet 24 in the second waist region 58.

In a particularly preferred embodiment of a medium sized diaper, such as the diaper 20 shown in FIG. 1, the waist closure system 40 preferably comprises a pair of first attachment components 46. Each first attachment component 46 comprises an about 12 mm wide (i.e., generally perpendicular to the longitudinal centerline 67) by about 19 mm patch of a hook fastening material. The first attachment components 46 are preferably positioned so as to have a lateral spacing of about 171 mm. Each first attachment component 46 is also spaced longitudinally from the end edge 64. If the longitudinal spacing of the first attachment component (measured from the end edge of the diaper to the closest edge of the first attachment component) is too small, the first attachment component may be too high on the diaper and be in a position to contact the wearer's skin; if the longitudinal spacing is too great, the first attachment component may be so low as to allow some rollover of the elasticized waistband. The first attachment components are preferably spaced from about 3 mm (⅛ inch) to about 15 mm (⅝ inch) from the end edge of the diaper, preferably about 6 mm (¼ inch). The hook fastening material used for the first attachment components 46 preferably comprises an array of thermoplastic prongs 120 formed on a backing; the prongs 120 of each hook fastening material most preferably being oriented with the engaging means facing inward toward the longitudinal centerline 67 of the diaper 20. The waist closure system 40 also comprises a single second attachment component 48 comprising a loop fastening material formed by a portion of the nonwoven material of the topsheet 24.

The diaper 20 additionally comprises a positioning patch 50 located subjacent the first attachment component 46. The positioning patch 50 raises the first attachment component 46 in the Z direction (thickness) to allow the first attachment component 46 to come in better contact with the second attachment component 48 and allow the waist closure system to more easily be closed (with less effort). Thus, the waist closure system 40 is more effectively passively activated. The positioning patch 50 also provides a zone of increased flexural stiffness that reduces the tendency of the flexible ear flaps 88 to fold over onto the first attachment component(s) 46 thereby occluding the hooks from being secured during diaper application. Thus, the positioning patch 50 can comprise any element that provides a Z direction build up to the first attachment components 46. As shown in FIG. 1, the positioning patches 50 each comprise a rectangular-shaped piece of material positioned subjacent the first attachment component 46. While the positioning patches 50 may be positioned directly subjacent the first attachment components 46, the positioning patches 50 are preferably positioned between the topsheet 24 and the backsheet 26. In order to provide a flexurally stiff circumference about the waist of the wearer, the lateral edges of the positioning patches can be abutted to or slightly overlapped with the side edges 75 of the elastic waistband member 76. The positioning patches 50 preferably comprise a 38 mm wide by 32 mm long patch of elastomeric foam. More preferably, during manufacture of the diaper, the positioning patches 50 are formed of the same material as the elastic side panel member 90 with the elastic side panel member 90 of one diaper and the positioning patch 50 of the adjacent diaper being formed from the same segment of material that is then cut after the diaper is completed. Thus, the positioning patch 50 extends from the end edge 64 of the diaper 20 inward toward the center of the diaper 20.

In a preferred embodiment, the diaper also comprises elasticized side panels 30 disposed in the second waist region 58. (As used herein, the term "disposed" is used to mean that an element(s) of the diaper is formed (joined and positioned) in a particular place or position as a unitary structure with other elements of the diaper or as a separate element joined to another element of the diaper.) The elasticized side panels 30 provide an elastically extensible feature that provides a more comfortable and contouring fit by initially conformably fitting the diaper to the wearer and sustaining this fit throughout the time of wear well past when the diaper has been loaded with exudates since the elasticized side panels allow the sides of the diaper to expand and contract. Further, the elasticized side panels 30 develop and maintain wearing forces (tensions) that enhance the tensions developed and maintained by both the primary fastening system 38 and the waist closure system 40 to maintain the diaper 20 on the wearer and enhance the waist fit. The elasticized side panels 30 especially assist in initially pretensioning the elasticized waistband 35 since the diaperer typically stretches the elasticized side panels 30 when applying the diaper 20 on the wearer so that when the elasticized side panels 30 contract, tension is transmitted from the elasticized side panels 30 through the waist closure system 40 into the elasticized waistband 34. The elasticized side panels 30 further provide more effective application of the diaper 20 since even if the diaperer pulls one elasticized side panel 30 farther than the other during application (asymmetrically), the diaper 20 will "self-adjust" during wear. While the diaper 20 of the present invention preferably has the elasticized side panels 30 disposed in the second waist region 58; alternatively, the diaper 20 may be provided with elasticized side panels 30 disposed in the first waist region 56 or in both the first waist region 56 and the second waist region 58.

While the elasticized side panels 30 may be constructed in a number of configurations, an example of a diaper with elasticized side panels positioned in the ears (ear flaps) of the diaper is disclosed in U.S. Pat. No. 4,857,067, entitled "Disposable Diaper Having Shirred Ears" issued to Wood, et al. on Aug. 15, 1989, which patent is incorporated herein by reference. The elasticized side panels 30 may alternatively be formed in a number of other configurations. For example, U.S. Pat. No. 4,381,781 issued to Sciaraffa, et al. on May 3, 1983, discloses a diaper having an elasticized waist in which an elastic member is positioned in an opening in both the topsheet and the backsheet of the diaper such that the stretch of the elastic member will not be constrained by the nonelastic materials. While the Sciaffra et al. patent teaches the criticality of removing both the topsheet and the backsheet portions of the diaper in those areas coinciding with the elastic member, the present inventors have learned that satisfactory elastic performance can also be obtained when only one or when none of the coinciding portions of the topsheet and the backsheet are removed, especially when the portions of the diaper web containing the elastic member are subjected to an incremental mechanical stretching operation of the type described hereinafter. A further embodiment of a diaper showing elasticized side panels is shown in U.S. Pat.

No. 4,938,753 issued to Van Gompel, et al. on Jul. 3, 1990. This patent discloses a pant-like garment provided with stretchable side panels formed by attaching discrete stretchable members to the side edges of the main body of the garment. Thus, the elasticized side panels 30 of the present invention may comprise a separate elastically extensible material or laminate joined to the diaper. As shown in FIG. 1, each elasticized side panel 30 preferably comprises an ear flap 88 and an elastic side panel member 90 operatively associated therewith.

As shown in FIG. 1, each ear flap 88 comprises that portion of the side panel 72 that extends laterally outwardly from and along the side edge 82 of the absorbent core 28 to the longitudinal edge 62 of the diaper 20. The ear flap 88 generally extends longitudinally from the end edge 64 of the diaper 20 to the portion of the longitudinal edge 62 of the diaper 20 that forms the leg opening (this segment of the longitudinal edge 62 being designated as leg edge 106). In a preferred embodiment of the present invention, each ear flap 88 in the second waist region 58 is formed by the portions of the topsheet 24 and the backsheet 26 that extend beyond the side edge 82 of the absorbent core 28.

In a preferred embodiment of the present invention, the elastic side panel members 90 are operatively associated with the diaper 20 in the ear flaps 88, preferably between the topsheet 24 and the backsheet 26, so that the elastic side panel members 90 allow the elasticized side panels 30 to be elastically extensible in the lateral direction (laterally elastically extensible). As used herein, the term "elastically extensible" means a segment or portion of the diaper that will elongate in at least one direction (preferably the lateral direction for the side panels and the waistbands) when tensional forces (typically lateral tensional forces for the side panels and the waistbands) are applied, and will return to about its previous size and configuration when the tensional forces are removed. Generally, elastomeric materials useful in the present invention will contractively return to at least about 75% of their original configuration within about 5 seconds or less upon stretch and immediate release thereof (i.e., a "snappy" elastic).

The elastic side panel members 90 can be operatively associated in the ear flaps 88 in a number of different ways. For example, the elastic side panel member 90 may be operatively associated in an elastically contractible condition so that the elastic side panel member 90 gathers or contracts the ear flap 88. (A more detailed description of a manner in which elastomeric materials may be secured in an elastically contractible condition can be found in U.S. Pat. No. 3,860,003 issued to Buell on Jan. 14, 1975, and in U.S. Pat. No. 4,081,301 issued to Buell on Mar. 28, 1978; both patents being incorporated herein by reference.) For example, the elastic side panel members 90 can be contractibly affixed in the ear map 88 by laterally extending the elastic side panel member 90, joining the elastic side panel member 90 to either or both the topsheet 24 and the backsheet 26, and allowing the elastic side panel member 90 to assume its relaxed or contracted orientation.

Alternatively, the elastic side panel member 90 can be operatively associated in an uncontracted state and then treated to contract. For example, the elastic side panel member 90 can be formed from materials which contract unidirectionally and become elastic following specific treatment such as heating. Examples of such materials are disclosed in U.S. Pat. No. 3,819,401 issued to Massengale, et al. on Jun. 25, 1974 and in U.S. Pat. No. 3,912,565 issued to Koch, et al. on Oct. 14, 1975. A more detailed description of a manner for using a heat-shrinkable elastic member is described in U.S. Pat. No. 4,515,595 issued to Kievit and Osterhage on May 7, 1985; this patent being incorporated herein by reference. Typically, the topsheet, the backsheet, the elastic side panel member, and any other components are secured together while in an uncontracted condition. The laminate is then heated (as with heated air) and the elastic side panel member is allowed to return to its relaxed or contracted orientation.

In an especially preferred embodiment, the elastic side panel member 90 is operatively associated in the ear flap 88 by joining the elastic side panel member 90 to the topsheet 24, the backsheet 26, or both while the elastic side panel member 90 is in a substantially untensioned condition. At least a portion of the resultant composite elastomeric laminate containing the elastic side panel member 90 is then subjected to mechanical stretching sufficient to permanently elongate the topsheet and the backsheet components (nonelastic components) of the laminate. The composite elastomeric laminate is then allowed to return to its substantially untensioned condition. The elasticized side panel is thus formed into a "zero strain" stretch laminate. (Alternatively, the elastic side panel member could be operatively associated in a tensioned condition and then subjected to mechanical stretching; although this is not as preferred as a "zero strain" stretch laminate.) As used herein, the term "zero strain" stretch laminate refers to a laminate comprised of it least two plies of material which are secured to one another along at least a portion of their coextensive surfaces while in a substantially untensioned ("zero strain") condition; one of the plies comprising a material which is stretchable and elastomeric (i.e., it will return substantially to its untensioned dimensions after an applied tensile force has been released) and a second ply which is elongatable (but not necessarily elastomeric) so that upon stretching the second ply will be, at least to a degree, permanently elongated so that upon release of the applied tensile forces, it will not fully return to its original undeformed configuration. The resulting "zero strain" stretch laminate is thereby rendered elastically extensible, at least up to the point of initial stretching, in the direction of initial stretching. Examples of such "zero strain" stretch laminates are disclosed in U.S. Pat. No. 2,075,189 issued to Galligan, et al. on Mar. 30, 1937; U.S. Pat. No. 3,025,199 issued to Harwood on Mar. 13, 1962; U.S. Pat. No. 4,107,364 issued to Sisson on Aug. 15, 1978; U.S. Pat. No. 4,209,563 issued to Sisson on Jun. 24, 1980; and U.S. Pat. No. 4,834,741 issued to Sabee on May 30, 1989. Each of these patents are incorporated herein by reference.

Particularly preferred methods and apparatus used for making "zero strain" stretch laminates out of a topsheet, a backsheet, and an elastomeric member positioned between the same, use meshing corrugated rolls to mechanically stretch the components. A discussion of suitable apparatus and methods for mechanically stretching portions of a diaper is contained in the hereinbefore referenced U.S. Pat. No. 4,107,364 issued to Sisson on Aug. 15, 1978 and U.S. Pat. No. 4,834,741 issued to Sabee on May 30, 1989. Particularly preferred apparatus and methods are disclosed in co-pending, commonly assigned, U.S. patent application Ser. No. 07/662,536 entitled "Improved Method And Apparatus For Incrementally Stretching A Zero Strain Stretch Laminate Web To Impart Elasticity Thereto"; P&G Case 4339; filed by Gerald M. Weber et al. on Feb. 28, 1991; U.S. patent application Ser. No. 07/662,537 entitled "Improved Method And Apparatus For Incrementally Stretching Zero Strain Stretch Laminate Web In A Non-Uniform Manner To Impart A Varying Degree of Elasticity Thereto"; P&G Case 4340;

filed by Kenneth B. Buell et al. on Feb. 28, 1991; and U.S. patent application Ser. No. 07/662,543 entitled "Improved Method And Apparatus For Sequentially Stretching Zero Strain Stretch Laminate Web To Impart Elasticity Thereto Without Rupturing The Web"; P&G Case 4341; filed by Gerald M. Weber et al. on Feb. 28, 1991; the specifications and drawings of each one incorporated herein by reference.

Figure 8:
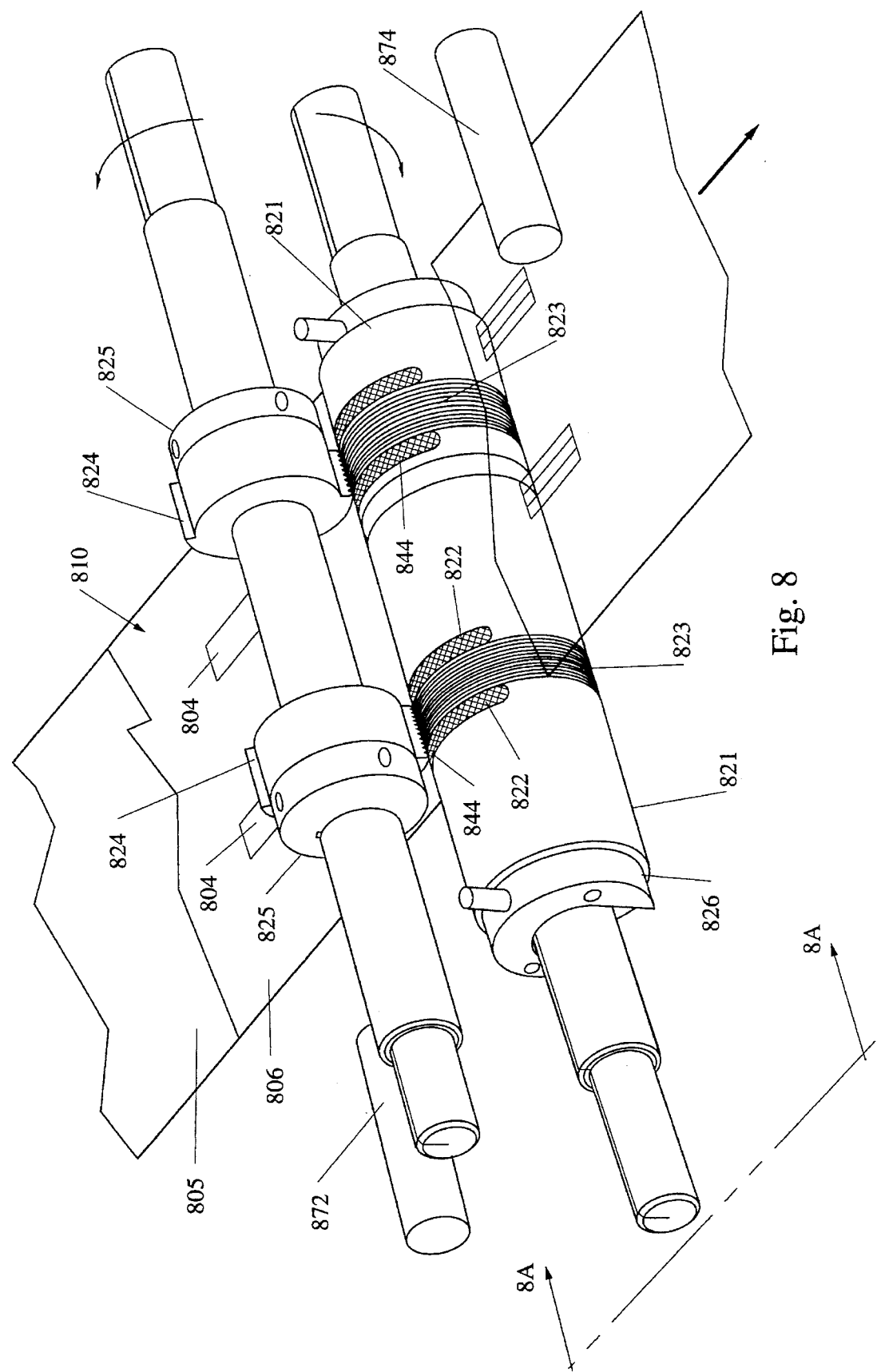
FIG. 8 is a simplified perspective view of an apparatus that employs a vacuum web restraint system for mechanically stretching a portion of a diaper web using meshing corrugated rolls.

Details of a particularly preferred incremental stretching system which can be employed in making "zero strain" stretch laminate elasticized side panels of the present invention are set forth in FIG. 8. The fully assembled diaper web 810 including the "zero strain" side panel web is directed through the incremental stretching system.

Referring to FIG. 8, the timing of the diaper web 810 containing the substantially untensioned elastic side panel members (elastomeric patches 804) is such that the substantially untensioned elastomeric patches 804 substantially coincide with the corrugated or grooved segments 824 contained on the uppermost corrugated rolls 825 as the diaper web 810 passes between the segments 824 of the uppermost corrugated rolls 825 and the continuously corrugated or grooved lowermost corrugated rolls 821. In a preferred embodiment of the method and apparatus, the grooved segments 824 are of greater overall length than the elastomeric patches 804, as measured in the machine direction, so as to impart a degree of extensibility to those portions of the topsheet 24 and the backsheet 26 which are adjacent the elastomeric patches 804 in the diaper 20 (i.e., an extension panel 110 is formed). In addition, the grooved segments 824 preferably are not of sufficient length to extend into the first waist region of the adjacent diaper, since it is preferable not to impart a degree of extensibility to the portion of the elastomeric patch 804 that will form the positioning patch 50 of the adjacent diaper.

While the exact configuration, spacing and depth of the complementary grooves on the uppermost and lowermost corrugated rolls will vary, depending upon such factors as the amount of elasticity desired in the "zero strain" stretch laminate portion, a peak-to-peak groove pitch of approximately 0.150 inches, an included angle of approximately 12 degrees as measured at the peak, and a peak-to-valley groove depth of approximately 0.300 inches have been employed in a particularly preferred embodiment of the present invention. The exterior peak of each corrugation on the aforementioned corrugated rolls typically exhibits a radius of approximately 0.010 inches, while the internal groove formed between adjacent corrugations typically exhibits a radius of approximately 0.040 inches. When the corrugated rolls are adjusted so that their opposing peaks overlap one another to a depth between about 0.150 and about 0.175 inches, good elastic characteristics have been produced in a laminate web of the present invention comprised of 80 mil thick elastomeric polyurethane foam patches substantially continuously bonded on their opposed surfaces to a one mil thick polymeric backsheet and a nonwoven topsheet having a basis weight in the range of about 18 to 20 grams per square yard and comprised of polypropylene fibers.

The degree of overlap of the opposing peaks on the aforementioned corrugated rolls may of course be adjusted, as desired, to produce more or less extensibility in the resultant "zero strain" stretch laminate web. For the aforementioned roll geometry and laminate web construction, peak-to-peak overlap depths ranging from as little as about 0.050 inches to as much as about 0.225 inches are feasible.

Figure 8A:
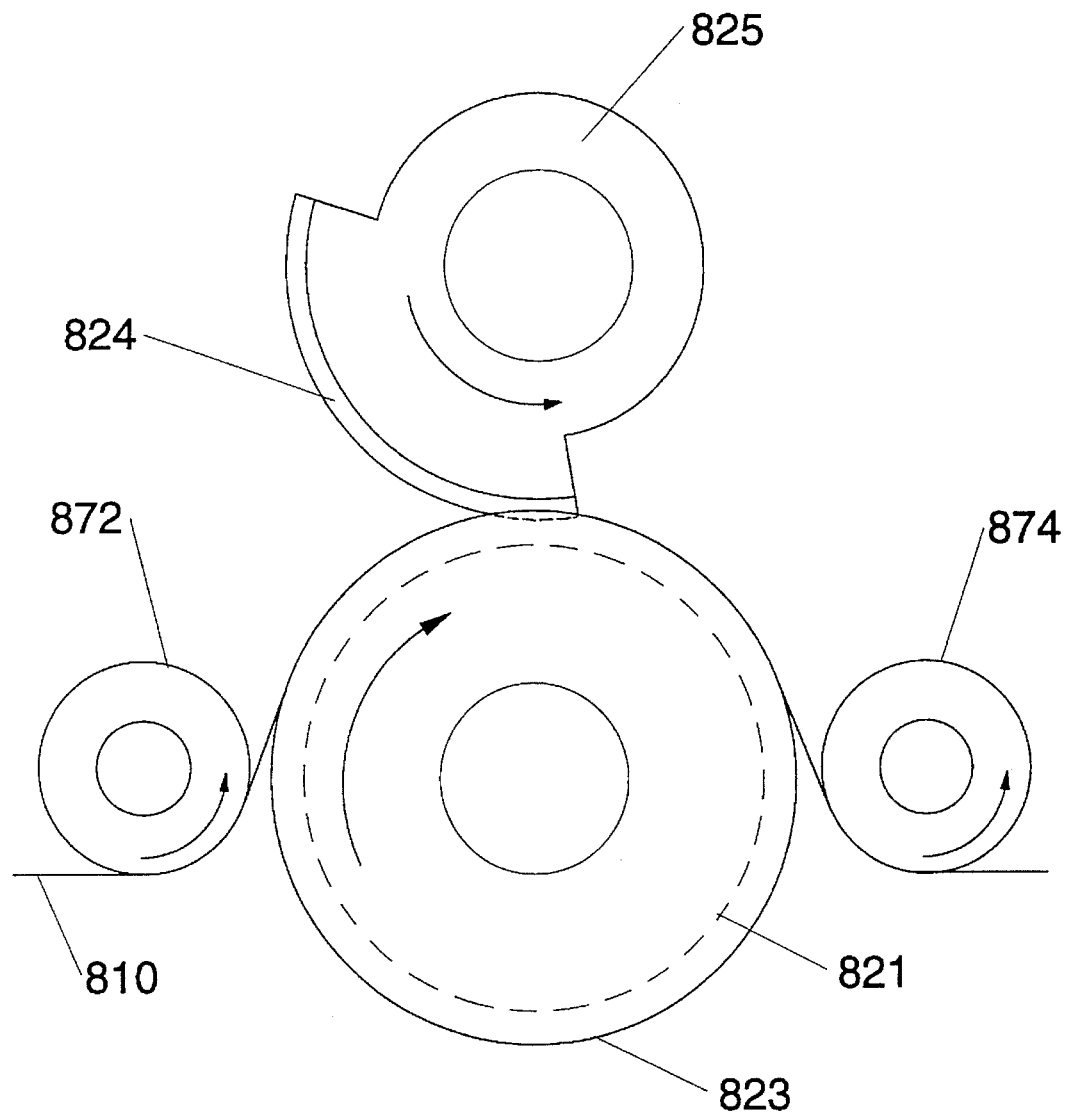
FIG. 8A is a simplified view taken along line 8A—8A in FIG. 8 showing the manner in which idler rolls are used to cause the diaper web to wrap the lowermost corrugated rolls.

As can be seen from FIG. 8A, the diaper web 810 is caused by the idler rolls 872, 874 to wrap the lowermost corrugated rolls 821 sufficiently to cover the active vacuum ports 822 (shown in FIG. 8) located immediately adjacent each continuous set of grooves 823 on the lowermost rolls 821. The vacuum ports 822, which are positioned so as to substantially coincide with the grooved segments 824 on the uppermost corrugated rolls 825, are internally connected through the rolls 821 to a pair of vacuum manifolds 826 which exert suction against the diaper web 810 as the diaper web is acted upon by the grooved segments 824 of the uppermost corrugated rolls 825.

To minimize the build up of either the adhesive used to secure the untensioned elastomeric patches 804 to the topsheet web 806 and the backsheet web 805 or the adhesive used to secure the coinciding portions of the topsheet web and the backsheet web to one another, the grooved segments 824 on the uppermost rolls 825 and the continuous grooves 823 on the lowermost rolls 821 may be either comprised of a low friction material, such as TEFLON, or coated with a self-lubricating low friction material such as Permalon No. 503 spray coating, as available from Nicro Surface Corporation of Morris, Ill.

The vacuum ports 822 on the lowermost rolls 821 are preferably covered by a porous material, such as 0.090 inch mesh honeycomb 844, to provide support to the portions of the diaper web 810 acted upon by the vacuum and to provide a good gripping surface against the web so as to substantially prevent lateral slippage or movement of the web across the honeycomb surface whenever the web is acted upon by the vacuum.

Under optimum circumstances, the maximum degree of incremental stretching which can be imparted to the "zero strain" portions of the side panel containing the elastomeric patches 804 is determined by the depth of engagement between the grooves on segments 824 of the uppermost corrugated rolls 825 and the continuous grooves 823 on the lowermost corrugated rolls 821. However, it has been discovered that unless the stretch laminate web is substantially prevented from slipping or contracting in a direction substantially parallel to the direction of web stretching as it passes between the meshing corrugated rolls, the optimum degree of incremental stretching is not realized. Therefore, in its most preferred form, the incremental web stretching operation is carried out while the outermost portions of all three layers comprising the "zero strain" stretch laminate are subjected to restraint, as generally shown in the cross-section of FIG. 8B, to substantially prevent the "zero strain" stretch laminate portions of the diaper web from slipping or contracting in a direction parallel to the desired direction of stretching as it passes between the sets of sequentially positioned meshing corrugated rolls.

However, the present invention may also, if desired, be practiced to advantage by restraining only the elongatable or drawable layer or layers of the composite, i.e., it is not an absolute requirement that the outermost portions of the elastomeric patches also be restrained during the incremental stretching operation. In the latter instance, the elongatable or drawable layer or layers are still permanently elongated during the incremental stretching process, but the z-direction bulking in the resultant "zero strain" stretch laminate web may be somewhat less pronounced when the stretching tension is removed. This is due to the fact that the elastomeric patch undergoes a lesser degree of initial stretching during such a process. Accordingly, it can only undergo this same amount of retraction when it returns to its undistorted configuration.

A "zero strain" stretch laminate embodiment of the aforementioned type may also exhibit some degree of disproportionate localized straining in the elongatable web or webs, particularly in the areas immediately adjacent the opposed edges of the elastomeric patches. In the case of an opaque polymeric backsheet web, these disproportionately strained portions can become sufficiently thinned that they may even appear transparent despite the fact that no rupture has taken place. In such instances the functionality, (e.g., the imperviousness) of the "zero strain" stretch laminate portions of the diaper web is not impaired. Embodiments of the latter type are normally employed in situations where the aesthetic appearance of the "zero strain" stretch laminate portions of the resultant diaper is either hidden from view by the design or configuration of the diaper or, if visible, is of no concern to the user of the diaper.

In still another embodiment of the present invention even rupture of one or more of the elongatable nonelastic webs may not render the resultant "zero strain" stretch laminate web unacceptable for its intended purpose (e.g., rupture of the backsheet web does not necessarily destroy the laminate web's functionality for its intended purpose as long as one of the other plies in the laminate web provides the desired function in the finished article). For example, some degree of rupturing in the elongatable backsheet web will not destroy the imperviousness of the resultant diaper web if the elastomeric patches also comprise a liquid-impervious material). This is particularly true with respect to those "zero strain" stretch laminate web embodiments employing substantially continuous bonding between the plies in question, since relatively close adherence of the plies to one another after incremental stretching renders such ply damage difficult to detect by the end user or the diaperer.

Figure 8B:
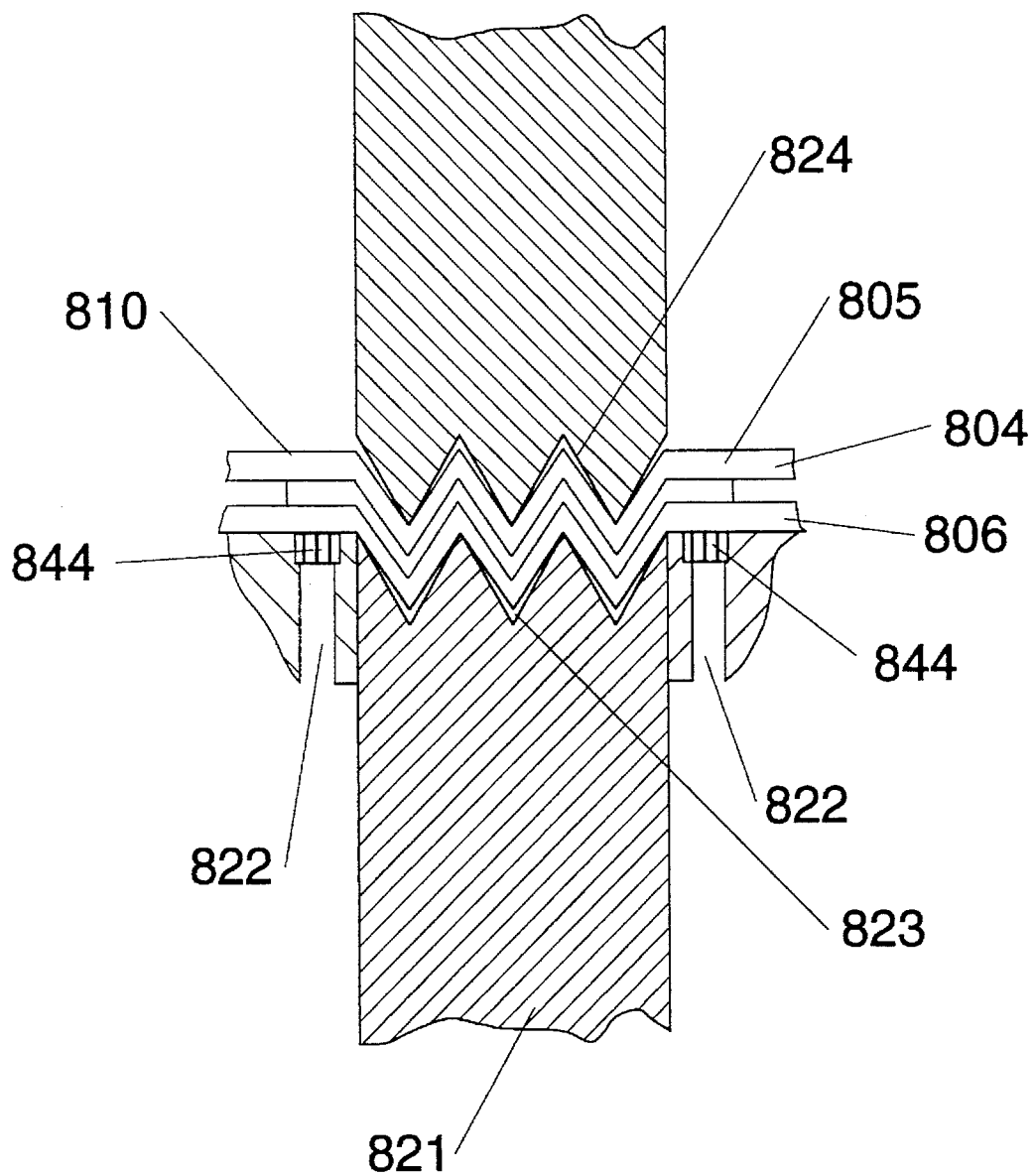
FIG. 8B is a highly enlarged view taken at the inset 8B shown in FIG. 8, showing the degree of meshing of the corrugated rolls with one another as the "zero strain" stretch laminate portion of the diaper web passes therebetween.

Because the diaper web 810 shown in FIGS. 8–8B is substantially impervious to the passage of air by virtue of the presence of the uppermost backsheet web 805, the vacuum ports 822 covered by the porous honeycomb material 844 can, if desired, be employed immediately adjacent each set of machine direction oriented grooves 823 in the lowermost corrugated rolls 821. If the elastomeric patches 804 are sufficiently pervious to the passage of air, the suction forces generated by the vacuum will pass through the topsheet web 806 and the elastomeric patches 804 so as to tightly grip the overlying portions of the backsheet 805. In this instance, all three layers comprising the "zero strain" stretch laminate portions of the diaper web will be restrained during the incremental stretching operation.

If the elastomeric patches were not substantially pervious to the passage of air, it would be necessary to either (a) position the vacuum ports 822 and the overlying honeycomb material 844 just outside the opposed edges of the elastomeric patches 804 so that suction forces could be exerted on the backsheet web 805 through the topsheet web 806; or (b) restrain all three layers comprising the "zero strain" stretch laminate portions of the diaper web by means of suitable clamping apparatus capable of acting upon the opposed surfaces of the diaper web.

The suction forces applied to the diaper web 810 shown in FIGS. 8–8B by the vacuum ports 822 acting through the porous honeycomb material 844 substantially prevent those portions of the diaper web 810 containing the substantially untensioned elastomeric patches 804 from slipping or contracting in laterally inward direction as they pass between the meshing portions of the continuous grooves 823 on the lowermost corrugated rolls 821 and the grooved segments 824 on the uppermost corrugated rolls 825.

Because the "zero strain" stretch laminate portions of the diaper web 810 containing the elastomeric patches 804 are laterally restrained throughout the sequential web stretching operation, all portions of the "zero strain" stretch laminate web located intermediate the points of restraint are subject to substantially uniform incremental stretching as the web passes between the continuous grooves 823 on the lowermost corrugated rolls 821 and the meshing portions of the grooved segments 824 on the uppermost corrugated rolls 825.

This not only maximizes the effectiveness of the incremental web stretching operation by forcing the elongatable topsheet and backsheet webs secured to the elastomeric patches to undergo the fullest possible degree of elongation during the stretching operation, but also substantially prevents disproportionately high straining of the topsheet and/or backsheet webs to which they are secured in the areas immediately adjacent the opposed peripheral edge portions of the elastomeric patches.

Figure 9:
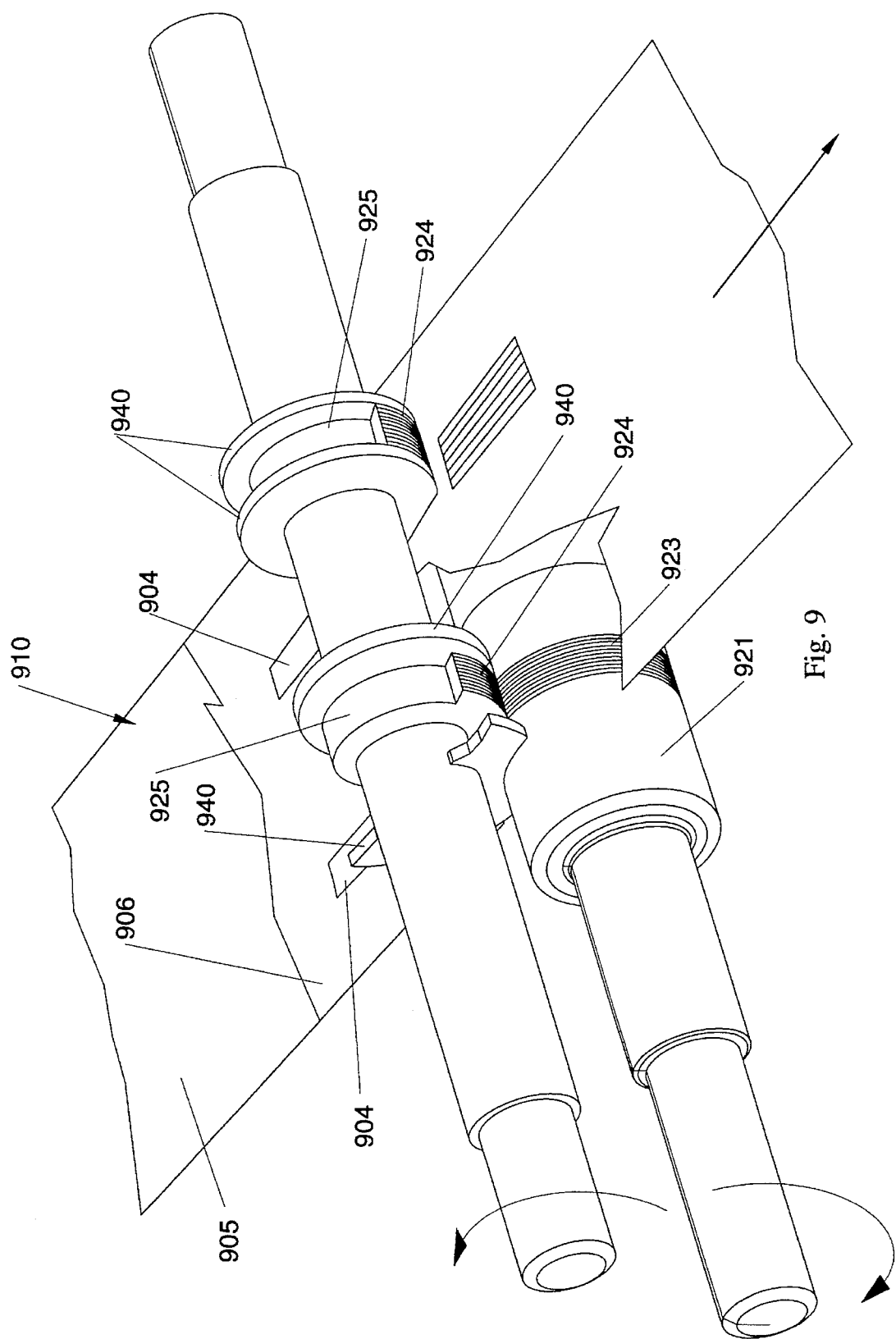
FIG. 9 is a simplified perspective view showing an alternative web restraint system of the present invention which may be used during the incremental stretching process disclosed herein.
Figure 9A:
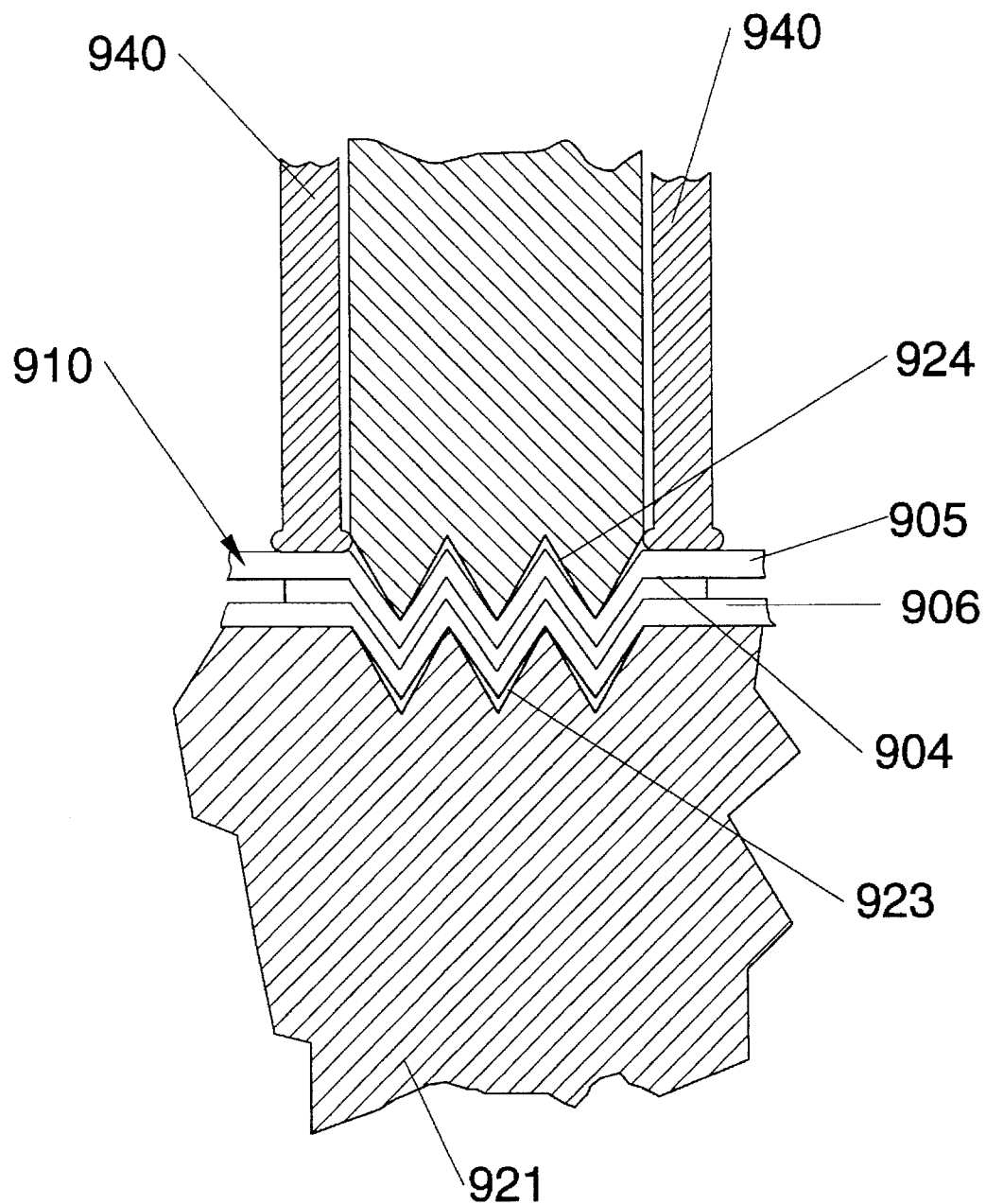
FIG. 9A is a highly enlarged simplified cross-sectional view taken at inset 9A shown in FIG. 9 along a centerline connecting the uppermost corrugated rolls and the lowermost corrugated rolls.

FIG. 9 discloses an alternative incremental web stretching system which can be employed. In the incremental web stretching system shown in FIG. 9, a pair of resiliently compressible disks 940 are mounted adjacent each side of the grooved segments 924 of the uppermost corrugated rolls 925. The compressible disks 940 are of a large enough diameter that they tightly grip the diaper web 910 and hold it securely against the coinciding non-grooved portions of the lowermost corrugated rolls 921 as generally shown in the cross-section of FIG. 9A. Like the vacuum ports and the porous honeycomb material in the embodiment of FIG. 8, the clamping effect created by the compressible disks 940 and the coinciding non-grooved portions of the lowermost rolls 921 substantially prevents the portion of the diaper web 910 containing the elastomeric patches 904 from contracting in a direction parallel to the direction of stretching as the web passes between the meshing corrugated rolls. The FIG. 9 embodiment can be used with equal facility on laminate structures comprised of webs which are either pervious or impervious to the passage of air.

As will be appreciated by those skilled in the art, the foregoing restraint methods may be employed either individually or in combination with one another to produce the benefits herein described in the resultant "zero strain" stretch laminate portions of the resultant diaper web.

From the description contained herein, it is clear that the improved method and apparatus may be employed to advantage to produce a wide range of diapers either comprised entirely of or including one or more discrete, isolated "zero strain" stretch laminate web portions.

It is also recognized that while a pair of meshing corrugated rolls having their corrugations aligned substantially parallel to one another are disclosed in the accompanying drawings, the present invention may be practiced with equal facility employing pairs of corrugated rolls wherein the corrugations are not all oriented parallel to one another. Furthermore, the corrugations on such pairs of corrugated rolls need not necessarily be aligned parallel to either the machine or the cross-machine direction. For example, if a curvilinear waistband or legband portion is desired in a single use diaper constructed using the "zero strain" stretch laminate technology herein disclosed, the meshing teeth on the pairs of corrugated rolls employed to incrementally stretch the "zero strain" laminate web portions of the diaper web may be arrayed in the desired curvilinear configuration to produce elasticity along the desired curvilinear contour rather than in a straight line.

It is further recognized that while the preferred processes herein disclosed employ meshing cylindrical corrugated rolls, the web restraint principles may also be carried out utilizing an intermittent stamping operation employing meshing platens to incrementally stretch the "zero strain" stretch laminate portions of the web or article in question. In the latter instance, the only requirement is that the portions of the "zero strain" stretch laminate web to be incrementally stretched be adequately restrained by suitable vacuum or clamping means before the meshing platens are able to exert enough force on the web to cause slippage or contraction in a direction parallel to the direction of stretching.

The elastic side panel members 90 can be joined to either the topsheet 24, the backsheet 26, or both using either an intermittent bonding configuration or a substantially continuous bonding configuration. As used herein, an "intermittently" bonded laminate web means a laminate web wherein the plies are initially bonded to one another at discrete spaced apart points or a laminate web wherein the plies are substantially unbonded to one another in discrete spaced apart areas. Conversely, a "substantially continuously" bonded laminate web means a laminate web wherein the plies are initially bonded substantially continuously to one another throughout the areas of interface. The intermittent bonding configuration is normally desirable for "zero strain" laminate webs in those situations where the substantially inelastic webs in the laminate are relatively elongatable or drawable without rupture and where a high degree of z-direction bulking is desired in the finished laminate. A continuous bonding configuration has generally been found desirable for "zero strain" laminate webs where the degree of z-direction bulking of the finished laminate is not of prime importance and one or more of the relatively inelastic webs in the laminate is difficult to elongate or draw without causing rupture. In the latter situation, a substantially continuous bonding configuration maintains all of the layers of the laminate in relatively close adherence to one another after the incremental stretching operation. Accordingly, even if one or more of the relatively inelastic webs is damaged to the point of rupture during the incremental stretching operation, the relatively close adherence of the damaged portions of the relatively inelastic web or webs to the elastomeric ply makes it difficult for the end user to perceive that any damage has occurred. Provided that the rupture of the relatively inelastic web or webs does not defeat the web's intended functionality, (e.g., imperviousness), the damage which does occur to the relatively inelastic web or webs during the incremental stretching operation is generally not perceived as a negative in the end product.

Thus, an unexpected benefit which results from the use of a continuous bonding configuration in particularly preferred "zero strain" stretch laminate webs is that it permits the manufacturer of the diaper to select from a much wider range of relatively inelastic webs which may be successfully employed in laminates of the present invention. In essence, it permits the use of relatively inelastic webs which would not normally be considered drawable to any appreciable extent in "zero strain" stretch laminate webs of the present invention. Accordingly, unless expressly stated otherwise, the term "drawable" as used herein, is not intended to exclude relatively inelastic webs which undergo a degree of thinning or damage during the incremental stretching operation.

In a preferred embodiment of the present invention, the elastic side panel member 90 is substantially continuously bonded to both the topsheet 24 and the backsheet 26 using an adhesive. A glue applicator may be used to apply a substantially uniform and continuous layer of adhesive to the backsheet 26 and/or the topsheet 24 in those predetermined areas where the substantially untensioned elastic side panel member 90 will be placed. In a particularly preferred embodiment, the adhesive selected is stretchable and the glue applicator comprises a melt blown applicating system.

One such melt blown adhesive applicating system which has been found to be particularly well suited for producing a substantially continuously bonded "zero strain" stretch laminate web is a melt blown spray applicator Model No. GM-50-2-1-GH, as available from J&M Laboratories of Gainesville, Ga. The latter system employs a nozzle having 20 orifices per lineal inch, as measured in the cross-machine direction, each orifice measuring approximately 0.020 inches in diameter. A Findley H-2176 Hot Melt Adhesive, as available from Findley Adhesives of Elm Grove, Wis. is preferably heated to a temperature of approximately 340° F. and applied to the backsheet and/or the topsheet at a rate of approximately 7.5–10 milligrams per square inch. Heated compressed air at a temperature of approximately 425° F. and a pressure of approximately 50 psig is issued through the secondary orifices in the adhesive nozzle to assist in uniformly distributing the adhesive fibrils during the laydown operation.

The intimate contact of the hot adhesive with the backsheet 26 for the time which passes prior to the incremental stretching of the resultant "zero strain" stretch laminate portion of the diaper provides softening of the backsheet 26. For some webs, such as conventional polyethylene backsheet material, this softening has been found beneficial in minimizing damage to the backsheet during the incremental web stretching process. This may be particularly important in situations where the web in question imparts some function, (e.g., impervious), to the diaper.

Alternatively, the elastic side panel member 90 and any other components comprising the "zero strain" portions of the diaper 20 may be intermittently or continuously bonded to one another using unheated adhesive, heat bonding, pressure bonding, ultrasonic bonding, dynamic mechanical bonding, or any other method as is known in the art.

The elastic side panel members 90 may take on a number of different sizes, shapes, configurations and materials. For example, the elasticized side panels 30 may be formed from one or a plurality of elastic side panel members 90 operatively associated in each ear flap 88; the elastic side panel members may have varying widths and lengths; or the elastic side panel members may comprise relatively narrow strands of elastomeric material or a larger area elastomeric patch. One elastomeric material which has been found to be especially suitable for use as the elastic side panel member 90 (especially for "zero strain" stretch laminates) is an elastomeric foam having an elongation to break of at least about 400% and an extension force of about 200 grams per inch of sample width at 50% extension of its unstrained length. Exemplary elastomeric foams which have been found suitable for use as an elastic side panel member include: (a) crosslinked natural rubber foams preferably having a caliper of approximately 50 mils and a density of 13.3 pounds per cubic foot (0.214 g/cm$^3$), such as is available from Fulflex Inc. of Middletown, R.I.; or as available from Ludlow Composites Corporation of Fremont, Ohio and marketed under the tradename Baby Foam; or (b) polyurethane foams having a caliper of approximately 80 mils and a density of approximately 2.06 pounds per cubic foot (0.033 g/cm$^3$) such as is available from Bridgestone of Yokohama, Japan and marketed under the tradename Bridgestone SG polyurethane foam; or as available from General Foam of Paramus, N.J. and marketed under the designation of Polyurethane Foam No. 40310. Other suitable elastomeric materials for use as the elastic side panel members 90 include "live" synthetic or natural rubber, other synthetic or natural rubber foams, elastomeric films (including heat shrinkable elastomeric films), elastomeric scrim, elastomeric woven or nonwoven webs, elastomeric composites such as elastomeric nonwoven laminates, or the like.

As shown in FIG. 1, the elastic side panel member 90 comprises a patch of elastomeric material (elastomeric patch) that preferably extends through a majority of the length of the ear flap 88 in the second waist region 58. When the diaper is manufactured, the elastomeric patch is preferably positioned so that it forms not only the elastic side panel member 90 of one diaper but also the positioning patch 50 in the first waist region 56 of the adjacent diaper. Thus, registry problems in securing the elastic side panel members to the diaper at high speed, such as disclosed in the previously referenced Wood, et al. patent, are eliminated. Thus, the elastic side panel member 90 preferably extends from the end edge 64 of the diaper 20 inward toward the leg edge 106 of the ear flap 88. The length and width of the elastic side panel members 90 are dictated by the diaper's functional design.

While the elastic side panel member 90 may longitudinally extend through the entire length of the ear flap 88, it is preferred that the elastic side panel member 90 extend through only a portion of the length of the ear flap 88 so as to form an extension panel 110. As shown in FIG. 1, the extension panel 110, the portion of the elasticized side panel longitudinally extending from the base edge 108 of the elastic side panel member 90 to the leg edge 106 of the ear flap 88, has also been mechanically stretched at least to a degree to be extensible (i.e., the materials that make up the extension panel 110 have been prestrained or permanently elongated). This "prestrained" extension panel allows this portion of the elasticized side panel to effectively elongate (yield) when the "zero strain" stretch laminate portion of the elasticized side panel is extended, without generating excessive tension forces near the leg regions of the wearer that could cause skin irritation or red marking in the legs. (i.e., Without the "prestrained" extension panel, tensional forces would be concentrated along a line through the extension panel 110 when the elasticized side panel is extended that could indent, rub, or chafe the skin of the wearer.) While there are a number of ways to prestrain the extension panel 110 of the elasticized side panels 30, the extension panel 110 is preferably prestrained in the same manner as the mechanical stretching performed on the "zero strain" stretch laminate portion. While the extension panel 110 of the elasticized side panels 30 may be formed from a number of different materials, in the preferred embodiment shown in FIG. 1, the extension panel 110 is formed from the portions of the topsheet 24 and the backsheet 26 forming the ear flap 88.

It has been found that the extension characteristics including the extension forces, extension modulus, and available stretch (extension); and the contractive forces; elastic creep; elastic hysteresis; and rate of contraction of the elasticized side panels 30 are important considerations in the performance of both the elasticized side panels 30 and the diaper 20. The extension characteristics give the diaperer and wearer the overall perceived "stretchiness" during use. They also effect the ability of the diaperer to achieve a suitable degree of application stretch (i.e., for a "normally" perceived tensioning of the diaper during application, the total amount of resultant stretch is that desired to achieve/maintain good conformity of fit). An elasticized side panel with a relatively high extension modulus can cause red marking on the wearer's skin while a relatively low extension modulus can cause sagging/slipping on the wearer. Elasticized side panels having too little available stretch may not achieve a suitable level of body conformity and may contribute in making the diaper uncomfortable to wear and hard to don. A diaper having elasticized side panels with very low contractive forces, or poor elastic creep or elastic hysteresis may not stay in place on the wearer and may tend to sag/slip on the wearer resulting in poor fit and containment.

For the elasticized side panels 30 of the present invention, it has been found that the extension characteristics of extension force and extension modulus are preferably within defined ranges. The extension force preferably is greater than or equal to about 250 grams$_f$. It is preferred that these extension forces be generated at extensions between about 0.25 inches (6.25 mm) and about 1.25 inches (31.25 mm). For the most preferred embodiments, the elasticized side panels preferably have an extensional force between about 250 grams$_f$ and about 500 grams$_f$ at an extension of between about 0.25 inches (6.25 mm) and about 0.75 inches (18.75 mm).

Available stretch measures the maximum amount of material available in the elasticized side panels to reversibly stretch to conform to the wearer's body during wear. Thus, the amount of available stretch relates to the maximum amount of extension that the diaperer has available to fit the diaper to the wearer. In addition, the maximum amount of recoverable extension available for the diaper to comply with wearer's body. The available stretch is calculated from the equation: ((stretched length—original length)—original length)×100. The minimum amount of available stretch required for a diaper application using elasticized side panels is preferably an available stretch of at least about 35% for medium sized diapers and at least about 50% for large sized diapers.

The amount of sustainable contractive force (tension) exerted by the elasticized side panel on the wearer is an important property of the elasticized side panel. An elasticized side panel with insufficient contractive forces may result in the diaper slipping down after being worn and loaded. Excessive contractive forces may reduce the comfort for the wearer and produce pressure markings on the wearer's skin. Contractive force is measured as the force per unit width produced while relaxing an elastomeric composite at a particular extension. In preferred embodiments of the present invention, the contractive force of the elasticized side panels is preferably at least about 90 grams/inch at 50% extension (a 50% extension would require the sample to be stretched to 1.5 times its original length).

Typical elastomeric materials show a hysteresis loop of force in their stress-strain property. That is, for a given extension, the force (extension force) required to uniaxally extend the elastomeric material is greater than the force (contractive force) the elastomeric material exerts when it is allowed to contract from its pre-extended condition. The former curve can be referred to as the "load curve" and the latter curve can be referred to as the "unload curve". The "load" extension force (extension force) is felt by the diaperer when the elasticized side panel is stretched to apply the diaper to the wearer. The wearer more nearly "feels" the "unload" contractive forces (contractive forces) once the diaper is on. Therefore, the hysteresis loss should not be so great that the contractive force is low enough to allow sagging/slipping of the diaper on the wearer.

All elastomeric materials undergoing sustained stress/strain have diminishing forces with time (i.e., elastic creep). Therefore, it is desired to make sure this reduction in wearing forces over time doesn't fall below a minimum for wearing stability. The elastic creep should therefore be kept at a minimum. In preferred embodiments of the present invention, the final length of the elastomeric material is not greater than about 1.2 times the original length under tension for 30 minutes.

The extension forces and available stretch of the elasticized waistband 35 can be important considerations in the performance of both the elasticized waistband 35 and the elasticized side panels 30. While the extension forces of the elasticized waistband 35 may be greater than the extension forces of the elasticized side panels 30, in a preferred embodiment of the present invention, the extension forces of the elasticized waistband 35 at its designed extensions is less than or equal to the extension forces of each elasticized side panel 30 at its designed extensions. An elasticized waistband 35 having lower extension forces than that of the elasticized side panels 30 provides for easy stomach movement without displacing the diaper on the child. The higher extension force elasticized side panels allow for small dimensional changes over the hip and under the stomach to keep the product comfortably in tension on the wearer. This design provides better fit, less leakage and improved comfort for the wearer through the reduction of sagging, gapping, rollover and roll-in at the front of the diaper and overall sliding/slipping of the diaper or diaper absorbent core on the wearer during use. As discussed herein, FIG. 6 discloses an alternative embodiment of the present invention wherein the shaped "expansive rummy panel" preferably has lower extension forces [and/or higher available stretch] than the elasticized side panels to provide the improved performance discussed herein.

The elasticized side panels 30 may also be provided with differential extensibility along the longitudinal axis when stretched in the lateral direction. As used herein, the term "differential extensibility" is used to mean a material having a nonuniform degree of elastic extensional properties, as measured in the direction of stretching at various points along an axis oriented substantially perpendicular to the direction of stretching. This may, for example, include varying the elastic modulus or available stretch or both of the elastomeric material(s). The differential extensibility is preferably designed into the elasticized side panels 30 so that the lateral extensibility varies longitudinally through at least a portion of the elasticized side panel as measured from the end edge 64 of the diaper 20 to the leg edge 106 of the ear flap 88. Without wishing to be bound by any theory, it is believed that differential extensibility along the longitudinal axis when stretched in the lateral direction allows the elasticized side panel to differentially stretch and conform to the wearer's waist during use while providing a secure anchor about the hip of the wearer so as to promote sustained fit and reduce leakage at the waist and legs. Such a configuration may allow more "expansion" in the hip area to accommodate changes in the wearers body size as the wearer moves and changes positions (standing, sitting, lying). In an alternative embodiment, a degree of reduced lateral extensibility in the portion of the elasticized side panel adjacent to the end edge 64 of the diaper 20 requires more of the total extension to be assumed by the elasticized waistband) thereby resulting in more localized stretching of the elasticized waistband 34 and a more compliant abdominal fit.

The differential extensibility can be achieved in a number of different ways. The elasticized side panels 30 can have multiple combined elastomeric materials, multiple configurations for the elastomeric materials, or the extension properties of the elastomeric or other material or materials making up the elasticized side panel may be nonuniform. For example, differential extensibility can be achieved in selected adjacent portions of the elasticized side panel by using elastomeric materials having varying extension or contractive forces, modulus, or other inherent properties such that more or less (varying) lateral extensibility is achieved in one portion of the elasticized side panel than the adjacent portion. The elastomeric materials may also have varying lengths, sizes, and shapes that provide differential extensibility. Other ways of varying the properties of materials that form the elasticized side panels as are known in the art may also be used.

A particularly preferred method and apparatus for imparting a varying degree of extensibility to a "zero strain" stretch laminate is to pass the "zero strain" stretch laminate through at least one set of meshing corrugated rolls, at least one of the corrugated rolls having corrugations of nonuniform profile along its point or points of contact with the "zero strain" stretch laminate web. As a result, the portions of the laminate web passing between the set of rolls are nonuniformly stretched. This, in turn, produces a "zero strain" stretch laminate which is nonuniformly elasticized in a direction substantially perpendicular to the nonuniformly profiled corrugations.

The diaper 20 is preferably applied to a wearer by positioning one of the waist regions, preferably the second waist region 58, under the wearer's back and drawing the remainder of the diaper between the wearer's legs so that the other waist region, preferably the first waist region 56, is positioned across the front of the wearer. The tab portions 94 of the tape tabs 92 are then released from the release portion 95. The diaperer then wraps the elasticized side panel 30 around the wearer, while still grasping the tab portion 94. The elasticized side panel 30 will typically be extended and tensioned during this operation so as to conform to the size and shape of the wearer. The first fastening component 112, the adhesive attachment layer 96, is secured to the second fastening component 114 of the landing member 44 to effect a side closure. In the preferred embodiment of the present invention, when the side closure is formed, the waist closure is also "automatically" formed, i.e., the waist closure is passively activated. The waist closure is formed by the engagement of the first attachment components 46 with the second attachment component 48. With the formation of the waist closure, the elasticized waistband 35 is pretensioned so as to provide the fit and containment benefits described herein.

Figures 4A, 4B, 4C, 4D:
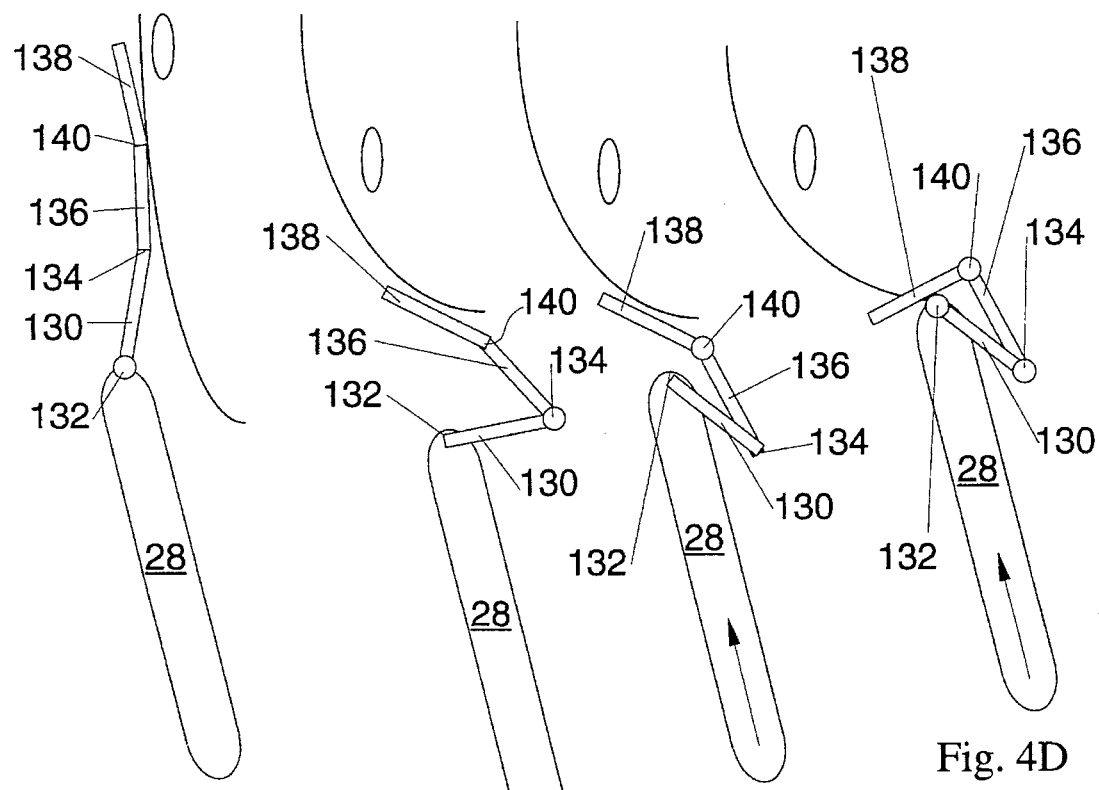
FIGS. 4A–4D are simplified kinematic representations of the functioning of the elastic waist feature during use as the wearer (shown in the drawings) moves from a standing position to a sitting position.

As shown in FIGS. 4A–4D, the elastic waist feature 34 of the present invention moves with and conforms to the waist of the wearer as the wearer sits, stands, or moves such that the end edge is in the same general relation with respect to the navel of the wearer when the wearer stands, sits, or stands after sitting. Therefore, the discussion that follows relates the relative motions in relation to the navel. As shown in FIG. 4A, the waistline panel zone 138 contacts the waist of the wearer and snugly fits against the waist as a result of the tension induced in the elasticized waistband by the closure system as initially applied. As shown in FIG. 4B, as the wearer begins to sit down, the interconnecting panel zone 130 pivots about the first flexural hinge zone 132 and about the second flexural hinge zone 134 to move the elasticized waistband out of the plane that it was originally in. The waist edge of the absorbent core tends to move toward the navel. As shown in FIG. 4C, as the wearer continues to sit down, the absorbent core is pushed further toward the navel while the interconnecting panel zone 130 tends to flex and fold about the absorbent core. The stomach of the wearer also begins to push outwardly to flexurally deflect the waistline panel zone 138 in relation to the shaping panel zone 136 about the predisposed waistband flexural hinge zone 140. As shown in FIG. 4D with the wearer completely sitting down, the absorbent core has pushed to its furthest extent against the belly with the interconnecting panel zone 130 totally flexed against the inner portion of the absorbent core. The shaping panel zone 136 is flexurally deflected to be in contact with the inner portion of the stomach while the waistline panel zone 138 has been completely pushed and flexurally deflected about the predisposed resilient waistband flexural hinge zone 140 to conform to the protruding waist of the wearer. Thus, a snug fit between the elasticized waistband and the wearer's waist is maintained. As the wearer stands up from sitting down, the process is repeated in reverse order with the resiliency of the waistband flexural hinge zone 140 providing a restoring force/moment that allows the waistline panel zone 138 to maintain contact with the waist of the wearer as the wearer continues to stand up, and to return the shaping panel zone 136 and the waistline panel zone 138 to their previous in-use (pretensioned) configuration against the waist with friction finally pulling the interconnecting panel zone 130 up into generally its original position with intimate contact between the elasticized waistband and the waist of the wearer. After several wearing cycles, a condition similar to that shown in FIG. 4B becomes the "neutral" position during standing, then all further movements of the wearer resemble the cycle shown in FIGS. 4B through 4D.

Figure 5:
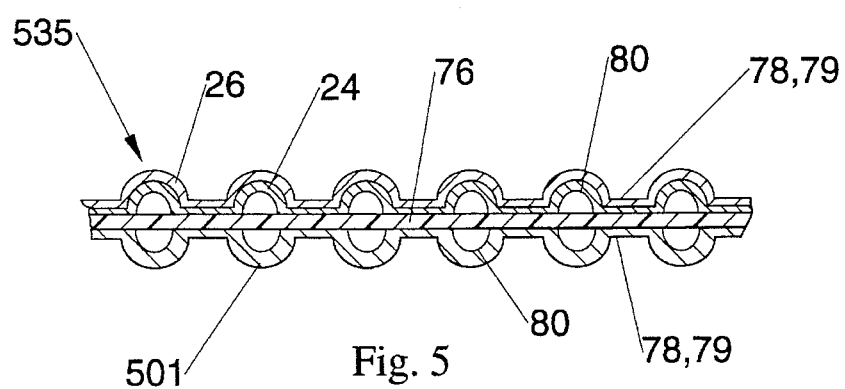
FIG. 5 is a fragmentary sectional view of an alternative disposable diaper embodiment of the present invention showing an alternative construction of the elasticized waistband.

FIG. 5 shows an alternative construction for the elasticized waistband of the present invention. The elasticized waistband 535 comprises a portion of the backsheet 26, preferably prestrained; a portion of the topsheet 24; and an elastic laminate comprising an elastomeric member 76 and a facing member 501. The elastomeric member 76 is positioned between the backsheet 26 and the facing member 501 with the topsheet 24 being positioned between the backsheet 26 and the elastomeric member 76. The elasticized waistband 635 is preferably formed by manufacturing the diaper with the topsheet 24 and the backsheet 26 joined together, forming a bi-laminate of the elastomeric member 76 and the facing member 501 in a separate step, and subsequently joining the bi-laminate material to the topsheet 24 of the combination topsheet/backsheet with the elastomeric member 76 facing the topsheet 24 so that the facing member 501 contacts the skin of the wearer. In this embodiment, the elastomeric member 76 is preferably a heat-shrinkable elastomeric material as previously described herein. The facing member 501 is preferably a soft, non-irritating material such as the materials previously described with respect to the materials suitable for use as the topsheet 24. The facing member 501 is preferably a nonwoven material similar to the nonwoven material preferred for use as the topsheet FIG. 5A shows a further alternative construction of the elasticized waistband of the present invention. The elasticized waistband 535 is formed from a portion of the backsheet 26, preferably prestrained; a facing member 501; an elastomeric member 76 positioned between the backsheet 26 and the facing member 501; a portion of the topsheet 24 positioned between the backsheet 26 and the elastomeric member 76; and a resilient member positioned between the topsheet 24 and the elastomeric member 76. The elasticized waistband 535 is preferably formed from the same materials as previously discussed and in the same manner as discussed with respect to the embodiment shown in FIG. 5, except that a tri-laminate of the facing member 501, the elastomeric member 76, and the resilient member 77 is formed and then secured to the topsheet 24.

FIG. 6 shows an alternative embodiment of the diaper and the elastic waist feature of the present invention. The elastic waist feature 634 comprises a relatively high edge compression stiffness interconnecting panel zone 130 flexurally joined to the containment assembly 22; an "expansive tummy panel" elasticized waistband 635 flexurally joined to the interconnecting panel zone 130; a first flexural hinge zone 132 flexurally joining the interconnecting panel zone 130 with the containment assembly 22; and a second flexural hinge zone 134 flexurally joining the elasticized waistband 635 with the interconnecting panel zone 130. As shown in FIG. 6, the elasticized waistband 635 has a deep "pentagon" shape to form an "expansive tummy panel". The elasticized waistband is longer (longitudinal dimension) to provide for the primary side closure to be formed below the area of stomach movement. The longest dimension of the elasticized waistband 635 (as measured from the end edge 64 longitudinally inward) is preferably between about 38 mm (1.5 inches) and about 88 mm (3.5 inches), more preferably between about 50 mm (2.0 inches) and about 57 mm (2.25 inches) for medium-sized diapers. This shape provides a waistband that moves and expands with the wearer's stomach as well as differential lateral extensibility such that portions of the elasticized waistband adjacent the end edge 64 are more extensible than adjacent portions farther from the end edge 64. The elasticized waistband 635 comprises a shaping panel zone 136; a waistline panel zone 138; and m predisposed, resilient, waistband flexural hinge zone 140. The waist edge 83 of the absorbent core 28 is generally parallel to the end edge 64 of the diaper (a straight line) and is moved longitudinally farther away from the end edge 64 to provide for the deeper "expansive tummy panel". (In medium-sized diapers, the waist edge 83 of the absorbent core 28 is preferably positioned between about 50 mm (2 inches) and 57 mm (about 2.25 inches) longitudinally away from the end edge 64.) The diaper embodiment shown in FIG. 6 additionally comprises a modified shape landing member 644 of the primary fastening system, longitudinally longer first attachment components 646 disposed on the backsheet 26, and a laterally wider positioning patch 650 positioned subjacent each of the first attachment components 646.

The elasticized waistband 635 is preferably constructed of a portion of the backsheet 26, a portion of the topsheet 24, an elastomeric member 76 positioned between the topsheet 24 and the backsheet 26, and a resilient member 77 positioned between the backsheet 26 and the elastomeric member 76. The elastomeric member 76 preferably comprises an elastomeric foam while the resilient member 77 comprises a nonwoven layer such as has been previously described herein. The bi-laminate elastomeric material of the elastomeric member 76 and the resilient member preferably extends beyond the mechanically stretched edges of the elasticized waistband 635 and forms a portion of the interconnecting panel zone 130 and a portion of the containment assembly 22 since it preferably extends longitudinally inwardly beyond the waist edge 83 of the absorbent core 28. The overlap of the bi-laminate elastomeric material with the absorbent core 28 is designed to stiffen the interconnecting panel zone 130 and to reduce the potential for roll-over of the elasticized waistband 635 in this embodiment. (In a preferred medium-sized diaper, the overlap between the elastomeric material and the absorbent core between 0 mm to about 6 mm (¼ inch)). The elasticized waistband 635 preferably comprises a stretch laminate so that the elasticized waistband is capable of expanding beyond the original planar state of the diaper. The elasticized waistband 635 is preferably manufactured by securing the elastomeric material between the topsheet and the backsheet (most preferably in m tensioned condition), and mechanically stretching (as hereinbefore described with respect to the elasticized side panels) the portion of the elastic waist feature in the shape desired to form the elasticized waistband. (i.e., the grooves and lands of the corrugated rolls correspond to the desired pentagon shape of the elasticized waistband.) This stretch laminate (preferably the mechanically stretched, pretensioned, stretch laminate) allows for expansion of the elasticized waistband well beyond the dimensions of the circumference of the diaper formed by the primary closure system and beyond the initial dimension of the end edge 64 (beyond the planar state of the diaper itself). (i.e., The elasticized waistband is capable of expanding well beyond the dimension of the circumference of the fixed dimension of the side closure (even beyond the dimension of the materials initially forming the diaper) so as to follow the wearer's stomach movements.) This expansion can also be accomplished by or enhanced (for stretch laminates) by "windowing" the elastic waist feature.

In this embodiment, the interconnecting panel zone 130 is relatively stiff and has a higher edge compression stiffness than the shaping panel zone 136 and the waistline panel zone 138. (Thus, this elastic waist feature functions differently than as shown in FIG. 4A–4D.) This relative stiffness of the Interconnecting panel zone 130 further enhances the ability of the elasticized waistband 635 to expand beyond the dimensions of the primary side closure. The interconnecting panel zone 130 preferably comprises a portion of the topsheet 24, a portion of the backsheet 26, a portion of the elastomeric material comprising the elastomeric member 76 and the resilient member 77, and a portion of the landing member 644 since the shape of the landing member 644 has been modified so as to conform to the shape of the elasticized waistband 635. The landing member also extends beyond the waist edge 83 of the absorbent core 28 to form a portion of the containment assembly 22. The landing member 644 preferably extends well beyond the waist edge 83 of the absorbent core 28 to allow lower taping of the primary closure system so as to position the primary side closure (the primary tension line) below the tree of stomach movement (i.e., below the lowermost point of the elasticized waistband). The top edge (the edge closest to the end edge) of the tape tab has also been longitudinally positioned farther from the end edge to accomplish this lower taping. The tape tab is preferably longitudinally positioned about 39 mm (about 1.56 inch) from the end edge in a preferred medium-sized diaper.

The shaping panel zone 136 of the elasticized waistband 635 comprises a portion of the backsheet 26, a portion of the topsheet 24, a portion of the elastomeric member 76, and a portion of the resilient member 77. The waistline panel zone 138 comprises a portion of the topsheet 24, a portion of the elastomeric member 76, and a portion of the resilient member 77. The waistline panel zone 138 does not comprise a portion of the backsheet 26 since it has been removed in this region. The predisposed, resilient, waistband flexural hinge zone 140 is formed by the structural discontinuity caused by the removal of the backsheet in the waistline panel zone 138 (a "windowed" elasticized waistband). The window is at least about 4.5 mm (about 3/16 inch), preferably from about 9 mm (about 3/8 inch) to about 16 mm (about 5/8 inch), long and about 125 mm (about 5 inches) wide for preferred medium-sized diapers. The waistline panel zone 138 is thus able to flexurally bend and deflect about the area where the backsheet has been removed. (In an alternative embodiment, the backsheet need not be removed but the pattern of bonding of the materials together would create the predisposed, resilient, waistband flexural hinge zone.) Thus, with the removal of the backsheet, the edge compression stiffness (and the extension forces) of the waistline panel zone is less than the edge compression stiffness (and the extension forces) of the shaping panel zone. As previously discussed, the edge compression stiffness of the shaping panel zone is less than the edge compression stiffness of the interconnecting panel zone. It has been found that the edge compression stiffness of the waistline panel zone is preferably less than about 100 grams$_f$, more preferably between about 20 grams$_f$ and about 50 grams$_f$, most preferably about 35 grams$_f$ with the edge compression stiffness of the shaping panel zone being preferably greater than that of the waistline panel zone, most preferably about 50 grams$_f$. The bending flexure restoring force of the waistband flexural hinge zone, and preferably the entire elasticized waistband, is greater than about 20 grams$_f$, more preferably between about 40 grams$_f$ and about 80 grams$_f$, most preferably about 60 grams$_f$.

Based upon the materials used and the manner of constructing the elasticized waistband, the extension forces at its designed "in-use" extensions are less than or equal to the extension forces of each elasticized side panel at their designed "in-use" extensions. The extension forces of the elasticized waistband are less than the extension forces of the elasticized side panels to allow the stomach to move more with the elasticized waistband as previously discussed herein. Further, the available stretch of the elasticized waistband is typically greater than the available stretch of the elasticized side panels. For preferred diapers, the extension forces of the elasticized waistband are preferably less than or equal to about 250 grams$_f$ at extensions of between about 25 mm (1 inch) and about 76 mm (3 inches), more preferably between about 25 mm (1 inch) and about 50 mm (2 inches). Most preferably, the extension forces for the elasticized waistband are between about 75 grams$_f$ and about 250 grams$_f$ at 25 mm (1 inch) to about 76 mm (3.0 inches) extensions, more preferably between about 25 mm (1 inch) and about 50 mm (2 inches). Since in a preferred embodiment of the elastic waist feature, a segment of the backsheet has been removed to form the waistline panel zone, the extension forces of the waistline panel zone are less than the extension forces of the shaping panel zone. (The edge compression stiffness is also changed by this windowing.) The extension forces of the waistline panel zone are preferably between about 75 grams$_f$ and about 175 grams$_f$ at these designed "in-use" extensions for the elasticized waistband while the extension forces of the shaping panel zone are preferably between about 175 grams$_f$ and about 225 grams$_f$ at these extensions. Most preferably, the extension force of the elasticized waistband in the waistline panel zone is about 150 grams$_f$ at a 50 mm (2 inch) extension and in the shaping panel zone is about 200 gram$_f$ at a 50 mm (2 inch) extension. This is in contrast to the extension forces of the elasticized side panels wherein it is desired that the elasticized side panels have an extension force window of greater than or equal to about 250 grams$_f$ at extensions of between about 6 mm (0.25 inches) and about 76 mm (3 inches), more preferably between about 250 grams$_f$ to about 500 grams$_f$ at extensions of between about 6 mm (0.25 inches) to about 19 mm (0.75 inches).

The positioning patch 650 is disposed in the diaper so as to abut with or extend beyond the side edge 75 of the elastomeric member 76 of the elasticized waistband 635.

The positioning patch 650 preferably comprises the same elastomeric foam material as is used for the elastomeric member 76. In fact, the positioning patch 650 can comprise a portion of the elastomeric member 76 if desired. This disposition for the positioning patch adds additional stiffness in the first side panels 70 to provide a more secure and stiffer panel that decreases the folding of the first side panel 70 at the crease between the elastomeric member 76 and the positioning patch 650. In a preferred embodiment of a medium-sized diaper, the positioning patch overlaps the elastomeric member from 0 mm to about 3.1 mm (⅛ inch).

The first attachment components 46 of the embodiment shown in FIG. 6 are preferably longer in the longitudinal direction because of the preferred shape of the elasticized waistband, because of the desire to pretension a greater area of the deeper elasticized waistband, and because of the preferred lower securement of the primary fastening system. In a preferred embodiment for medium-sized diapers, the first attachment components are preferably about 25 mm (about 1 inch) long.

FIG. 7 shows an alternative embodiment of the elastic waist feature shown in FIG. 6. As shown in FIG. 7, the shape of the waist edge 783 of the absorbent core 28 has an arcuate shape. The arcuate shape absorbent core has ears 700 which extend upwardly beyond the elasticized waistband 735 to bound a portion of the elasticized waistband and to further stiffen the areas adjacent the elasticized waistband 735 and provide additional containment.

In a further alternative embodiment, the elasticized waistband is formed similarly to that shown in FIG. 2 except that the resilient member comprising a nonwoven material interposed between the topsheet and the elastomeric member rather than between the backsheet and the elastomeric member as shown in FIG. 2.

An alternative embodiment of an elastic waist feature additionally comprises a waistcap feature. Such a waistcap feature is disclosed in U.S. Pat. No. 4,734,246 issued to Lawson on May 10, 1988 and in U.S. patent application Ser. No. 07/571,000, allowed, Robertson, filed on Aug. 21, 1990; each of which are incorporated herein by reference. The waistcap would be formed as an extension of the elastomeric material or elastomeric laminate forming the elasticized waistband. The elastic waist feature would thus additionally comprise a waistcap zone extending longitudinally inward from the waist edge of the absorbent core. The waistcap zone would comprise a barrier member having a proximal edge joined to the containment assembly (preferably the topsheet) adjacent the waist edge and a distal edge capable of being spaced away from (Z direction) the absorbent core to provide a channel to contain body exudates.

FLEXURE BENDING TEST

Figure 11:
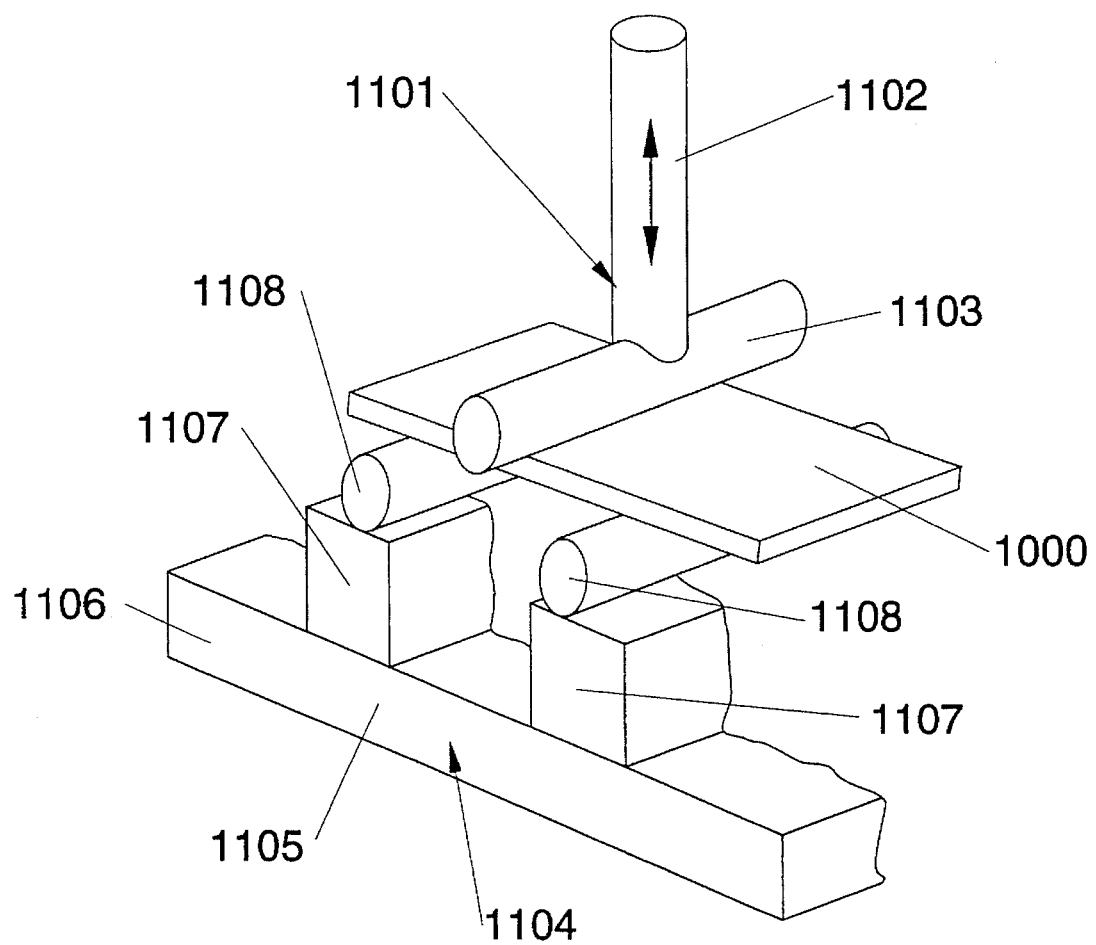
FIG. 11 is a perspective view of a test apparatus for measuring the bending flexure recovery force of the waistband flexural hinge zone of the elastic waist feature.

The flexure bending test uses an INSTRON Model 4502 as available from Instron Corporation of Canton, Mass., a special displacement "T-rod", and a special test sample holder. As shown in FIG. 11, the "T-rod" 1101 comprises a pair of ¼ inch (6.35 mm) diameter metal rods perpendicularly mounted together. Preferably, the end of the drive rod 1102 (the longer of the rods, being about 125 mm (about 5.25 inches)) is tapered to fit the circumference of the push rod 1103 (the shorter of the rods, being about 75 mm (about 3 inches)) and the two are glued, welded and/or screwed to each other. The opposite end of the drive rod 1102 is mounted to the crosshead unit of the INSTRON. The test sample holder 1104 comprises a fixture base 1105 to position and support the supporting rods 1108. The fixture base 1105 comprises a base 1106 and two rectangular supports 1107 mounted in parallel on the base 1106. The base 1106 and the supports 1107 are each preferably made of LEXAN (plexiglas) plate of about ½" to ⅜" thickness. A supporting rod 1108 (same material as the "T-bar" and about 150 mm (about 6 inches) long) is mounted on each support 1107 of the fixture base 1105. The supporting rods 1108 are mounted so as to be spaced 16 mm apart, center-to-center. As shown in FIG. 11, the "T-rod" 1101 is centered between the supporting rods 1108.

The INSTRON is set for a crosshead speed of 20 mm/min, a chart speed of 400 mm/min, and with full scale at 500 grams$_f$. The INSTRON is set up so that the crosshead unit will travel 6 mm down and back, with the chart to follow the crosshead unit down and back.

Figure 10:
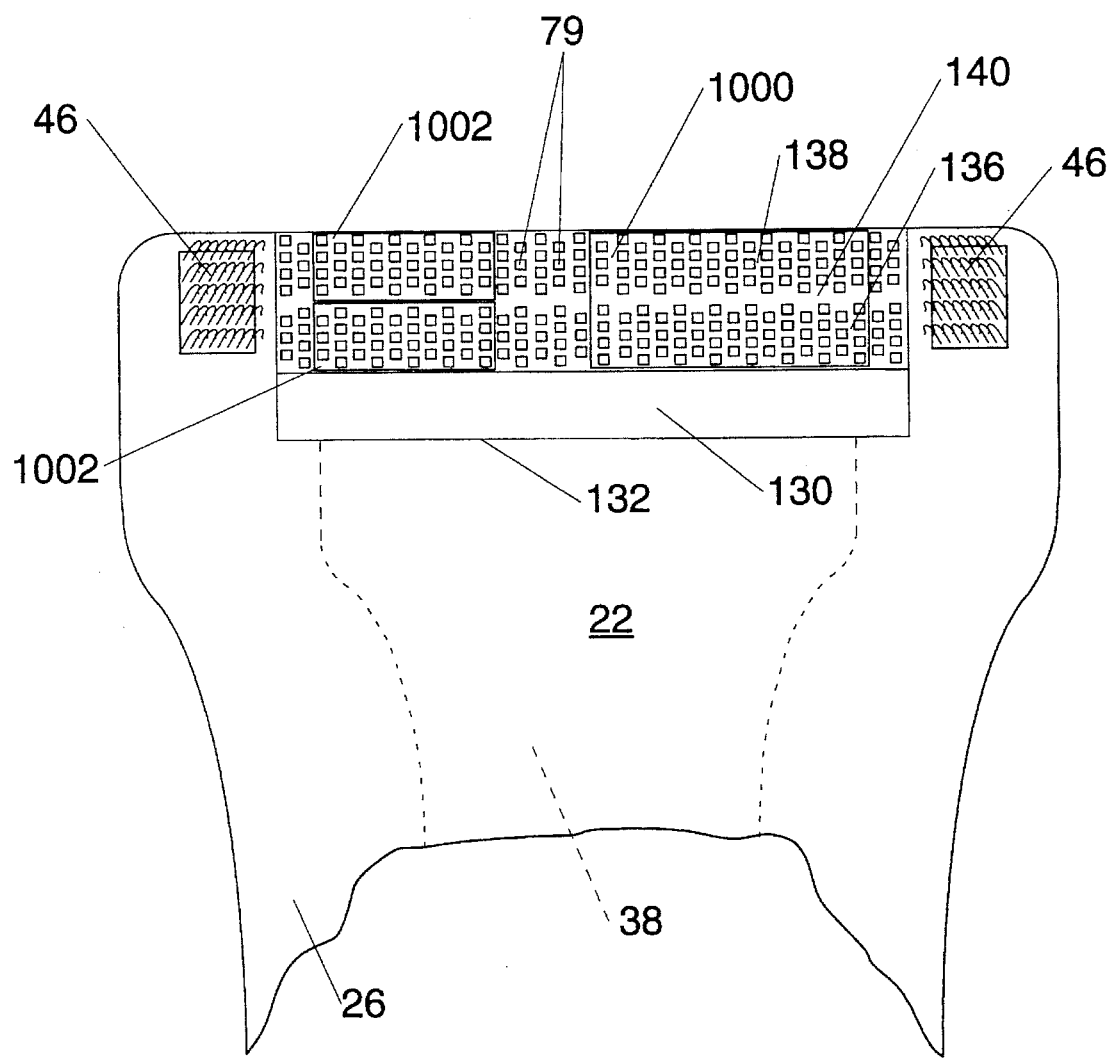
FIG. 10 is a simplified, fragmentary, enlarged plan view of the disposable diaper of the present invention in the first waist region showing the location for taking test samples from the elastic waist feature.

As shown in FIG. 10, the sample 1000 to be tested is taken from the elastic waist feature 34 so that the waistband flexural hinge zone 140 is preferably centered within the sample although some samples may not have the waistband flexural hinge zone centered. The sample 1000 is at a minimum 16 mm long (longitudinal direction), preferably 25 mm or any length available, and 50 mm wide (lateral direction.) As shown in FIG. 11, the sample 1000 is centered on the supporting rods 1108 so that the waistband flexural hinge zone 140 will be directly under the T-rod 1101. The outer surface of the sample 1000 (typically the backsheet side) is placed toward the T-rod 1101.

The T-rod 1101 is "zeroed" on top of the sample 1000 with a light preload of a few grams (1 to 4 grams$_f$). This takes out any bowing of the sample and insures good contact of the T-rod with the sample. Each sample is run through the 6 mm travel cycle twice, with a 30 second stop between cycles. A total of ten samples are run.

Figure 12:
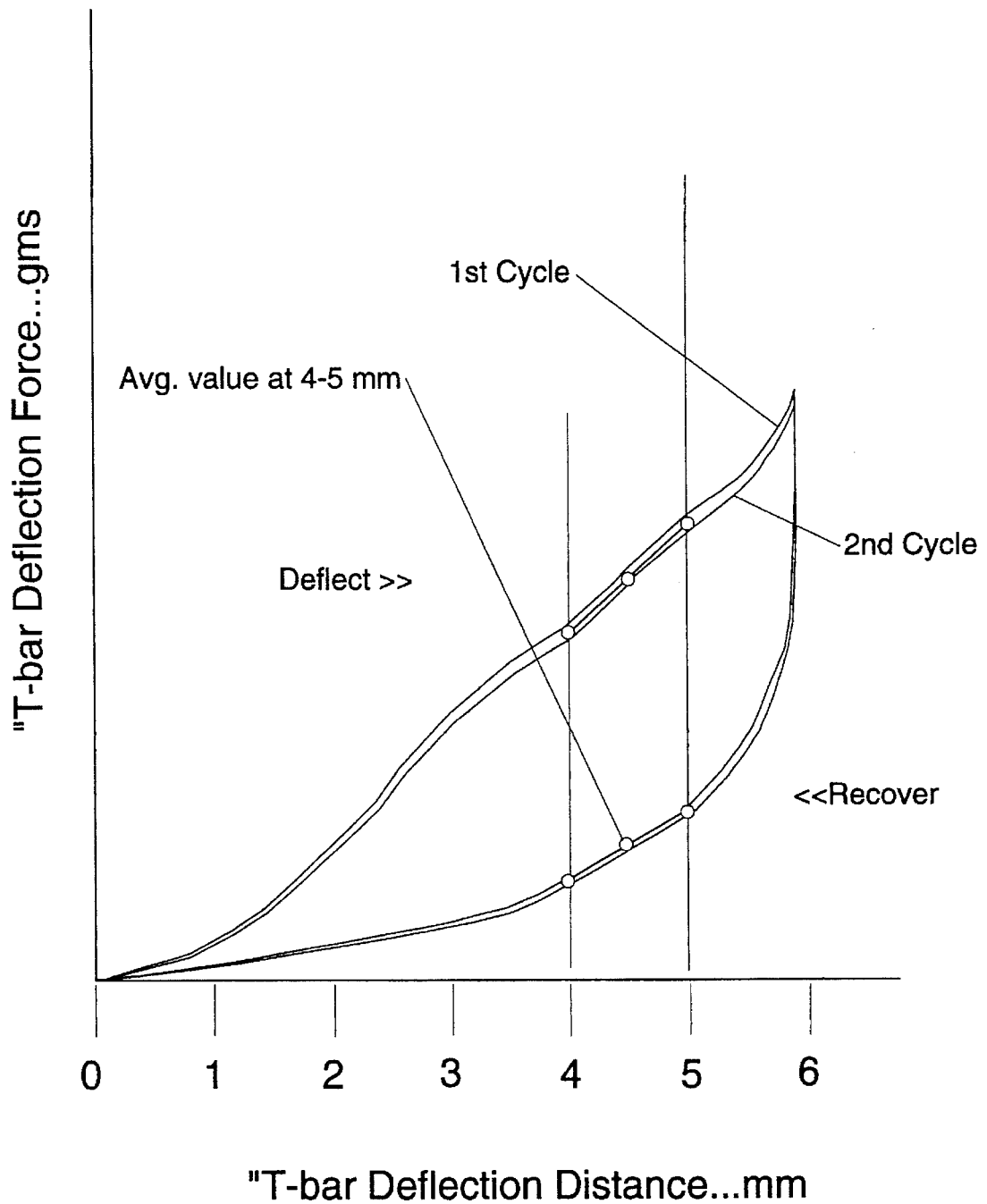
FIG. 12 is a representative graph of deflection force versus deflection distance of two cycles of the flexure bending test.

A graph of T-bar deflection force (grams$_f$) versus T-bar deflection distance (mm) will be generated. A representative run of a sample showing the two cycles is shown in FIG. 12. The deflection force at 4 mm and 5 mm, for each cycle, is determined on the recovery force curve. The recovery deflection force at 4 mm and 5 mm are averaged to calculate a cycle recovery deflection force. The average of both cycle recovery deflection forces for each sample determines the sample recovery deflection force. The bending flexure recovery force for the structure is the average of the value of the sample recovery deflection force for the 10 samples.

EDGE COMPRESSION STIFFNESS TEST

Figure 13:
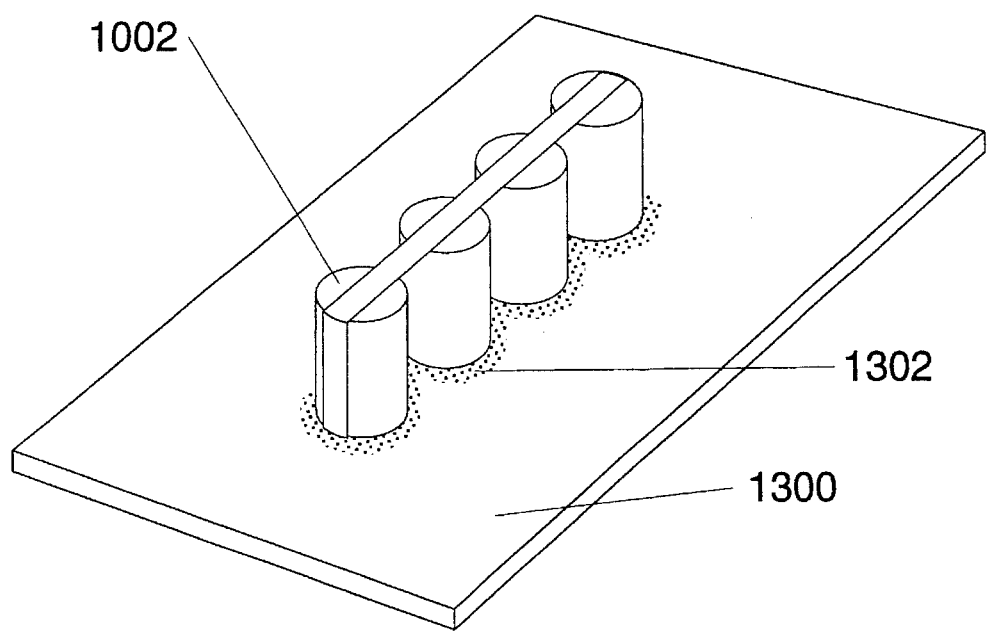
FIG. 13 is a perspective view of the test sample created according to the test procedures for determining the edge compression stiffness of a panel zone of the elastic waist feature.

The edge compression stiffness test uses an INSTRON Model 4502 as available from Instron Corporation of Canton, Mass., a special test sample holder, and mounting adhesive. As shown in FIG. 13, the samples 1002 are mounted to a 1 inch (25 mm) by 2 inch (50 mm) by 1/16 inch (1.56 mm) aluminum flat plate 1300 by the mounting adhesive 1302. The mounting adhesive 1302 is a quick set epoxy as available from Hartman Adhesives of Belleville, N.J. and marketed as Red-04001 double bubble packs.

The INSTRON is provided with a compression load cell. (The load cell and the INSTRON jaw flat plate should be checked for flatness and squareness.) The INSTRON is set for a crosshead speed of 5 mm/min., a chart speed of 250 mm/min., and full scale of 100 or 500 grams (as needed). The cycle length is 3.5 mm down and back, with the chart to follow the crosshead unit down and back.

As shown in FIG. 10, the sample 1002 to be tested is taken from the elastic waist feature 34 in preferably the waistline panel zone 138 or the shaping panel zone 136 or the interconnecting panel zone 130 depending upon which zone is to be tested. The sample 1002 is 9 mm in length by 25 mm wide.

The mounting adhesive 1302 is spaced on the plate 1300 using a doctor blade to make a footprint approximately ⅜ inch (8.5 mm) wide and a height of 0.020 inch to about 0.030 inch (0.5 to 0.75 mm). The sample 1002 is placed in the mounting adhesive 1302 and held perpendicular to the plate 1300 with blocks on either side of the sample. These blocks are relieved at the base so that they will not get into the mounting adhesive. After the mounting adhesive has been given some time to set (approximately 1 minute or more), the mounted samples are placed in a 73° F./50% relative humidity room for about 24 hours or overnight so that the mounting adhesive can fully set.

Figure 14:
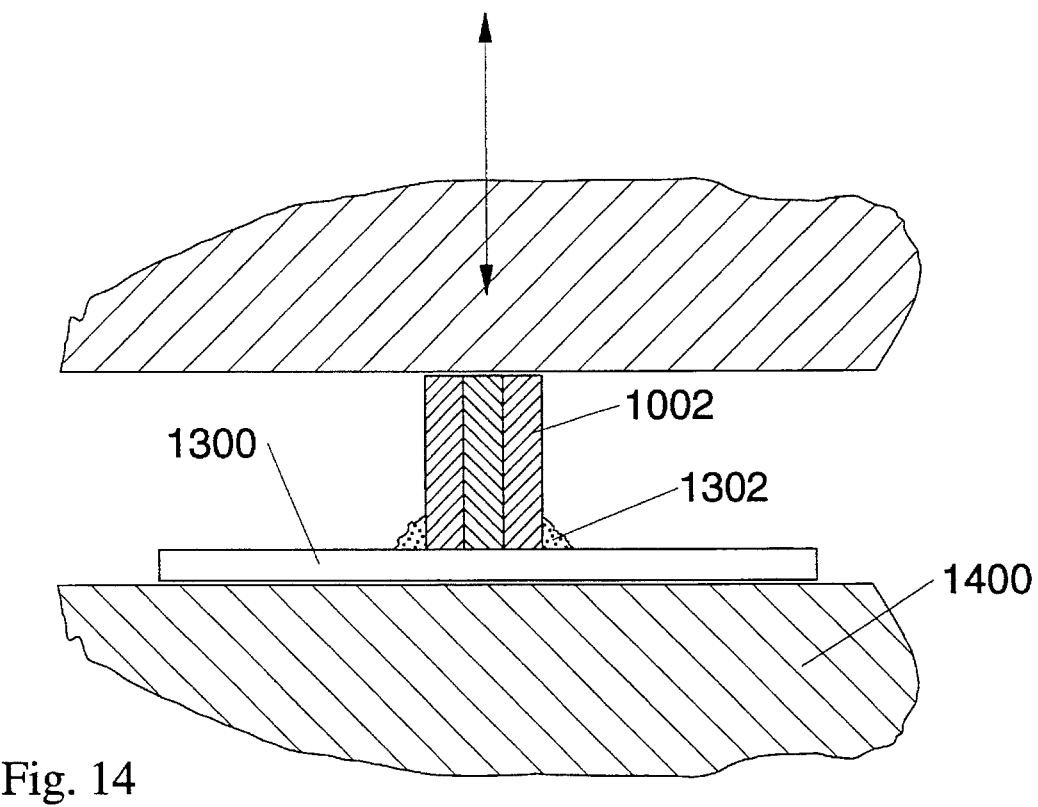
FIG. 14 is a simplified side view of the apparatus and test sample "set up" for determining the edge compression stiffness of a panel zone of the elastic waist feature.

The mounted samples are placed on the lower jaw 1400 of the INSTRON as shown in FIG. 14. The samples are preloaded with a 1 to 4 grams$_f$ preload to zero the INSTRON. Each sample is run through a 3.0 mm deflection cycle twice, with 30 seconds allowed between the cycles. Five samples are tested.

Figure 15:
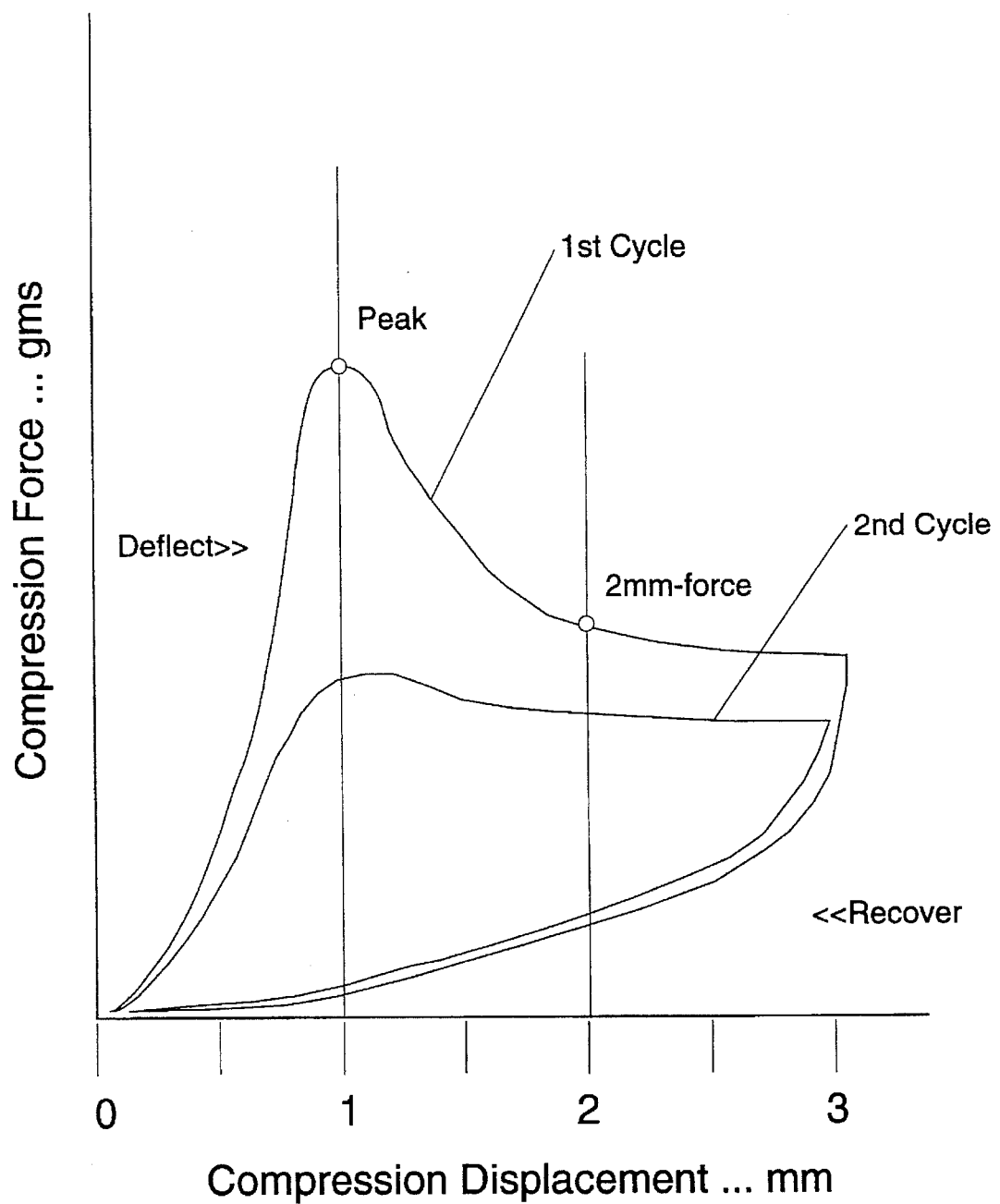
FIG. 15 is a representative graph of compression force versus compression displacement of two cycles of the edge compression stiffness test.

A graph of compression force (grams$_f$) versus compression displacement (mm) will be generated. A representation run of a sample showing the two cycles is shown in FIG. 15. The peak force for the run is measured as the highest force generated during both cycles. The average of the peak compression forces for the five samples is the edge compression stiffness of the zone.

EXTENSION FORCE TEST

The extension force test for both the elasticized side panels 30 and the elasticized waistband 35 uses an INSTRON Model 4502 as available from Insiron Corporation of Canton, Mass.

A. ELASTICIZED SIDE PANELS

The INSTRON is set for a crosshead speed of 100 mm/min, a chart speed of 500 mm/min, and with full scale at 1000 grams$_f$. The INSTRON will be allowed to travel the desired, claimed, or full elastic extension of the side panel. (If the full extension of the side panel is less than the upper limit claimed, then the test is stopped at this extension since the extension forces at nonextensible areas should not be taken into account; i.e., the designed in-use extension limit has been reached.)

The sample to be tested is determined on the actual diaper itself. A standard 3 inch (75 mm) clamp is attached to the elasticized side panel 30 adjacent the edge of the activated stretch portion of the side panel laterally closest to the longitudinal centerline 67. In most situations, this edge corresponds to the side edge 93 of the elastic side panel member 90. A standard 1 inch (25 mm) clamp is attached to the opposite edge of the activated stretch portion of the elasticized side panel 30 (typically the side edge 91' of the elastic side panel member 90). The 1 inch clamp is positioned so as to be within the area of the 3 inch clamp and longitudinally aligned with the component of the primary fastening system 38 positioned adjacent the elasticized side panel 30. Thus, in a preferred embodiment, the 1 inch clamp is longitudinally aligned with the securement member 42, tape tab 92, so that the force applied by the INSTRON is similar to the force applied by the user when applying the diaper.

Each sample is run through a travel cycle to the designed, claimed, or full extension of the activated elastic portion of the elasticized side panel. (The sample may be allowed to contract to also measure contractive force.) A graph of extension force (grams$_f$) versus extension (mm) will be generated. A total of ten samples are run. The extension force at a given extension is the average of the values for the 10 samples.

B. ELASTICIZED WAISTBAND

The INSTRON is set for a crosshead speed of 500 mm/min, a chart speed of 500 mm/min, and with full scale at 500 grams$_f$. The INSTRON will be allowed to travel the desired, claimed, or full elastic extension of the waistband. (If the full extension of the waistband is less than the upper limit claimed, then the test is stopped at this extension since the extension forces at nonextensible areas should not be taken into account; i.e., the designed in-use extension limit has been reached.)

The sample to be tested is taken from the elasticized waistband 35, preferably adjacent the upper edge of the elasticized waistband (except where specific panel zones are to be tested). The sample is preferably 25 mm (1 inch) long (longitudinal direction) and about 125 mm to about 150 mm wide (lateral direction) so that a sample width of 100 mm (4 inches) is tested. If the elasticized waistband 35 or the panel zone to be tested is less than 25 mm (1 inch) long (longitudinal direction) so that a 25 mm (1 inch) sample cannot be obtained, the test may be carried out using this modified size sample although this is not a preferred situation. The ends of the sample are clamped using standard 1 inch (25 mm) clamps with 4 inches (100 mm) between the clamps. (No zones or areas of the sample should be nonextensible excluding bond sites).

Each sample is run through a travel cycle to the desired, claimed, or full extension of the elasticized waistband sample. (The sample may be allowed to contract to also measure contractive force.) A graph of extension force (grams$_f$) versus extension (mm) will be generated. A total of ten samples are run. The extension force at a given extension is the average of the values for the 10 samples.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A unitary disposable absorbent article comprising:
   a containment assembly having end edges, longitudinal edges having leg edges, a longitudinal axis, a first waist region, and a second waist region, said containment assembly comprising:
   a topsheet,
   a backsheet joined with said topsheet, and
   an absorbent core positioned between said topsheet and said backsheet; and
   an elasticized side panel disposed on said containment assembly adjacent each longitudinal edge in said second waist region, each said elasticized side panel being elastically extensible in at least the lateral direction, each said elasticized side panel having differential extensibility, a non uniform degree of elastic extensional properties as measured in the direction of stretching at various points along an axis oriented substantially perpendicular to the direction of stretching, along the longitudinal axis when stretched in the lateral direction such that the lateral extensibility varies longitudinally from one portion of said elasticized side panel to an adjacent portion.

2. The absorbent article of claim 1 wherein the lateral elastic extensibility of each said elasticized side panel varies longitudinally through at least a portion of said elasticized side panel as measured from said end edge to said leg edge.

3. The absorbent article of claim 2 wherein said elasticized side panel comprises an ear flap and an elastic side panel member joined to said ear flap, said ear flap comprising a portion of said topsheet and said backsheet.

4. The absorbent article of claim 3 wherein each said elasticized side panel comprises a zero strain stretch laminate that has been nonuniformly stretched.

5. The absorbent article of claim 2 wherein each said elasticized side panel has a degree of reduced lateral elastic extensibility adjacent said end edge.

6. The absorbent article of claim 5 additionally comprising an elasticized waistband disposed in said second waist region.

7. The absorbent article of claim 1 wherein said elastic side panel member comprises multiple elastomeric materials.

8. The absorbent article of claim 7 wherein said elastomeric materials having varying extension properties.

9. The absorbent article of claim 2 wherein said elastic side panel member comprises multiple elastomeric materials.

10. The absorbent article of claim 9 wherein said elastomeric materials having varying extension properties.

11. The absorbent article of claim 5 wherein said elastic side panel member comprises multiple elastomeric materials.

12. The absorbent article of claim 11 wherein said elastomeric materials having varying extension properties.

* * * * *

UNITED STATES PATENT AND TRADEMARK OFFICE
CERTIFICATE OF CORRECTION

PATENT NO. : 5,591,152  
DATED : January 7, 1997  
INVENTOR(S) : Kenneth B. Buell et al.

page 1 of 3

It is certified that error appears in the above-indentified patent and that said Letters Patent is hereby corrected as shown below:

| | |
|---|---|
| Column 5, line 66 | delete "m" and insert --a--. |
| Column 7, line 25 | after "35" insert --is--. |
| Column 7, line 41 | after "region " insert --56.--. |
| Column 8, line 59 | after "zones, " insert --a--. |
| Column 11, line 22 | delete "denter" and insert --denier--. |
| Column 13, line 58 | delete "m" and insert --a--. |
| Column 15, line 11 | delete "110" and insert --170--. |
| Column 16, lines 31 & 41 | delete "28" and insert --2B--. |
| Column 18, line 65 | delete "17" and insert --77--. |
| Column 19, line 4 | delete "Are " and insert --are--. |
| Column 19, line 9 | delete "At" and insert --at--. |
| Column 19, line 14 | delete "1s" and insert --is--. |
| Column 19, line 15 | delete "denter " and insert --denier--. |
| Column 19, line 47 | after "6" insert --mm--. |
| Column 19, line 54 | delete "Incremental" and insert --incremental--. |
| Column 19, line 60 | delete "Interrupted" and insert --interrupted--. |
| Column 20, line 9 | delete "1s" and insert --is--. |
| Column 22, line 9 | delete "Well" and insert --Weil--. |

UNITED STATES PATENT AND TRADEMARK OFFICE
CERTIFICATE OF CORRECTION

PATENT NO. : 5,591,152

DATED : January 7, 1997

INVENTOR(S) : Kenneth B. Buell et al.

It is certified that error appears in the above-indentified patent and that said Letters Patent is hereby corrected as shown below:

| | |
|---|---|
| Column 22, line 47 | delete "Westgard" insert --Nestegard--. |
| Column 24, line 25 | after "layer " insert --96.--. |
| Column 24, line 26 | after "surface " insert --a--. |
| Column 24, line 30 | delete "$8" and insert --58--. |
| Column 24, line 34 | delete "Ferris" and insert --Farris--. |
| Column 30, line 8 | delete "Hills" and insert --Mills--. |
| Column 30, line 28 | delete "is" and insert --as--. |
| Column 30, line 30 | delete "tactfiers" and insert --tacifiers--. |
| Column 33, line 53 | delete "map " and insert --flap--. |
| Column 34, line 26 | delete "it" and insert --at--. |
| Column 36, line 19 | delete "Nicro" and insert --Micro--. |
| Column 42, line 52 | delete "uniaxtally " and insert --uniaxially--. |
| Column 43, line 29 | delete "rummy" insert --tummy--. |
| Column 43, line 61 | delete ")" and insert --34--. |
| Column 45, line 62 | after "member" insert --77--. |
| Column 46, line 29 | delete "m" and insert --a--. |
| Column 46, line 54 | after "member" insert --77--. |
| Column 46, line 65 | after "core" insert --is--. |

UNITED STATES PATENT AND TRADEMARK OFFICE
CERTIFICATE OF CORRECTION

PATENT NO. : 5,591,152
DATED : January 7, 1997
INVENTOR(S) : Kenneth B. Buell et al.

It is certified that error appears in the above-indentified patent and that said Letters Patent is hereby corrected as shown below:

| | |
|---|---|
| Column 47, line 5 | delete "m" and insert --a--. |
| Column 47, line 29 | delete "Interconnecting" and insert --interconnecting--. |
| Column 47, line 44 | delete "tree" and insert --area--. |
| Column 49, line 32 | after "material" insert --is--. |
| Column 50, line 20 | after "sample" insert --1000--. |
| Column 51, line 35 | delete "Insiron" and insert --Instron--. |
| Column 51, line 52 | delete "93" and insert --91--. |

Signed and Sealed this

Eighth Day of July, 1997

Attest:

BRUCE LEHMAN

Attesting Officer      Commissioner of Patents and Trademarks